(12) United States Patent
Cohen et al.

(10) Patent No.: US 10,500,226 B2
(45) Date of Patent: Dec. 10, 2019

(54) ALGINATE COMPOSITIONS AND USES THEREOF

(71) Applicants: Hadasit Medical Research Services and Development Ltd., Jerusalem (IL); B.G. Negev Technologies & Applications Ltd., at Ben-Gurion University, Beer-Sheva (IL)

(72) Inventors: Smadar Cohen, Beer-Sheva (IL); Yaron Ilan, Kfar-Tavor (IL); Eyal Shteyer, Mevaseret Zion (IL); Ami Ben-Ya'Acov, Jerusalem (IL)

(73) Assignees: Hadasit Medical Research Services and Development Ltd., Jerusalem (IL); B.G. Negev Technologies & Applications Ltd., at Ben-Gurion University, Beer-Sheva (IL)

( * ) Notice: Subject to any disclaimer, the term of this patent is extended or adjusted under 35 U.S.C. 154(b) by 0 days.

(21) Appl. No.: 14/758,589

(22) PCT Filed: Dec. 30, 2013

(86) PCT No.: PCT/IL2013/051089
§ 371 (c)(1),
(2) Date: Jun. 30, 2015

(87) PCT Pub. No.: WO2014/102802
PCT Pub. Date: Jul. 3, 2014

(65) Prior Publication Data
US 2015/0335675 A1    Nov. 26, 2015

Related U.S. Application Data

(60) Provisional application No. 61/747,325, filed on Dec. 30, 2012, provisional application No. 61/747,328, filed on Dec. 30, 2012.

(51) Int. Cl.
*A61K 31/734* (2006.01)
*A61K 31/167* (2006.01)
*A61K 9/00* (2006.01)
*A61K 45/06* (2006.01)

(52) U.S. Cl.
CPC .......... *A61K 31/734* (2013.01); *A61K 9/0053* (2013.01); *A61K 31/167* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2,405,861 A | 8/1946 | Tod | |
| 5,266,326 A * | 11/1993 | Barry | A61L 31/042 424/423 |
| 5,384,400 A * | 1/1995 | Crescenzi | A61K 8/73 127/29 |
| 5,658,329 A * | 8/1997 | Purkait | A61F 2/12 623/23.72 |
| 5,888,987 A * | 3/1999 | Haynes | C08J 9/26 424/443 |
| 5,955,107 A | 9/1999 | Augello et al. | |
| 6,425,918 B1 * | 7/2002 | Shapiro | A61F 2/105 424/426 |
| 9,993,497 B2 | 6/2018 | Cohen et al. | |
| 2003/0195179 A1 * | 10/2003 | Sawa | A61K 9/0014 514/174 |
| 2005/0008572 A1 * | 1/2005 | Prokop | A61K 9/5161 424/9.6 |
| 2005/0089577 A1 | 4/2005 | Yokoyama et al. | |
| 2005/0142207 A1 * | 6/2005 | Wang | A61K 9/1635 424/490 |
| 2005/0226968 A1 | 10/2005 | Holzschuh et al. | |
| 2006/0083721 A1 * | 4/2006 | Cohen | A61K 9/0024 424/93.7 |
| 2006/0173004 A1 * | 8/2006 | Bollbuck | C07D 207/14 514/235.5 |

(Continued)

FOREIGN PATENT DOCUMENTS

| | | |
|---|---|---|
| DE | 19723155 | 12/1998 |
| EP | 1842544 | 10/2007 |

(Continued)

OTHER PUBLICATIONS

ProNova VLVG sodium alginate description retrieved om Aug. 14, 2017 from http://www.novamatrix.biz/store/pronova-up-vlvg/.*
Warring Torq 2.0 blender specification sheet, waringcommercialproducts.com, retrieved on Aug. 11, 2017 (Year: 2017).*
"Saline" definition from Miller-Keane Encyclopedia and Dictionary of Medicine, Nursing, and Allied Health, Seventh Edition.2003 (Year: 2003).*
Ruvinov, E., Leor, J., & Cohen, S. (2011). The promotion of myocardial repair by the sequential delivery of IGF-1 and HGF from an injectable alginate biomaterial in a model of acute myocardial infarction. Biomaterials, 32(2), 565-578. (Year: 2011).*

(Continued)

*Primary Examiner* — Dale R Miller

(57) ABSTRACT

Compositions comprising an alginate, a source of sodium ions and a carrier (e.g., a pharmaceutically acceptable carrier), which are characterized by reduced association of the alginate chains and hence by at least one of: (i) a zeta potential weaker than −25 mV, at a concentration of 0.5% (w/v) alginate in the carrier; and (ii) a diffusion coefficient of at least $10^{-8}$ $cm^2$/second, at a concentration of 0.5% (w/v) alginate in the carrier, are disclosed. Also disclosed are uses of the composition and methods utilizing the composition for treating inflammatory bowel disease; liver damage, diseases and disorders, for treating a medical condition treatable by a hepatotoxic agent and for reducing or preventing liver damage, including liver damage caused by a hepatotoxic agent.

14 Claims, 27 Drawing Sheets
(8 of 27 Drawing Sheet(s) Filed in Color)

(56) References Cited

U.S. PATENT DOCUMENTS

| | | | |
|---|---|---|---|
| 2008/0029116 A1* | 2/2008 | Robinson | A24B 13/00 131/352 |
| 2009/0304811 A1 | 12/2009 | Xia et al. | |
| 2010/0247652 A1* | 9/2010 | Ilan | A61K 31/734 424/488 |
| 2011/0053886 A1 | 3/2011 | Melvik et al. | |
| 2012/0122768 A1 | 5/2012 | Onsoyen et al. | |
| 2012/0128734 A1 | 5/2012 | Hibinette et al. | |
| 2012/0213708 A1* | 8/2012 | Anderson | A61K 9/0019 424/9.2 |
| 2014/0113347 A1* | 4/2014 | Lisboa | A61K 35/12 435/178 |
| 2015/0352144 A1 | 12/2015 | Cohen et al. | |
| 2018/0099006 A1 | 4/2018 | Cohen et al. | |

FOREIGN PATENT DOCUMENTS

| | | | |
|---|---|---|---|
| GB | 555940 | 9/1943 | |
| IN | 1248/MUM/2010 | 2/2013 | |
| JP | 10-114683 | 5/1998 | |
| KR | 10-2010-0008683 | 1/2010 | |
| RU | 2019981 | 9/1994 | |
| WO | WO 95/19743 | 7/1995 | |
| WO | WO 97/44070 | 11/1997 | |
| WO | WO 98/12228 | 3/1998 | |
| WO | WO 03/037299 | 5/2003 | |
| WO | WO 2004/082594 | 9/2004 | |
| WO | WO 2004/098669 | 11/2004 | |
| WO | WO 2007/113454 | 10/2007 | |
| WO | WO-2009064617 A1 * | 5/2009 | A61K 31/728 |
| WO | WO 2009/069131 | 6/2009 | |
| WO | WO 2009/083759 | 7/2009 | |
| WO | WO 2010/104464 | 9/2010 | |
| WO | WO 2014/102801 | 7/2014 | |
| WO | WO 2014/102802 | 7/2014 | |

OTHER PUBLICATIONS

FMC Corporation, ProNova alginates product specification sheets, from http://www.novamatrix.biz/store, retrieved on May 10, 2018 (Year: 2018).*

Supplementary European Search Report and the European Search Opinion dated Jul. 12, 2016 From the European Patent Office Re. Application No. 13869473.2.

Supplementary European Search Report and the European Search Opinion dated Jun. 27, 2016 From the European Patent Office Re. Application No. 13869503.6.

Aoki et al. "Diffusion Coefficients in Viscous Sodium Alginate Solutions", Electrochimica Acta, XP028945079, 83: 348-353, Available Online Aug. 10, 2012. Described Alginate Compositions and Their Properties.

FAO "Compendium of Food Additive Specifications: Sodium Alginate", FAO, Food and Agriculture Organisation, 49th JEFCA, XP055280173, p. 1-3, Jan. 1, 1997. Process in Section 'Microbiological Citeria': Sodium Alginate Prepared by Dispersing Alginate Sodium in Saline Solution and Homogenizing at High Speed, Descripted Alginate Compositions and Their Properties.

Liu et al. "[Pharmacokinetics of Doxorubicin Alginate Microspheres and Evaluation of Its Hepatic Arterial Emboliziation In Vivo]", Database Medline [Online], XP002758841, Dataase Accession No. NLM17039787, Aug. 2006. Abstract.

Nagarwal et al. "Chilosan Coated Sodium Alginate-Chitosan Nanoparticles Loaded With 5-FU for Ocular Delivery: In Vitro Characterization and In Vivo Study in Rabbit Eye", European Journal of Pharmaceutical Sciences, XP002758840, 47(4): 678-685, Available Online Aug. 16, 2012. Pharmaceutical Compositions Comprising Sodium Alginate (Which Is Also a Carrier) and 5FU (Which Is an Hepatotoxic Agent).

International Preliminary Report on Patentability dated Jul. 9, 2015 From the International Bureau of WIPO Re. Application No. PCT/IL2013/051088.

International Preliminary Report on Patentability dated Jul. 9, 2015 From the International Bureau of WIPO Re. Application No. PCT/IL2013/051089.

International Search Report and the Written Opinion dated Apr. 1, 2014 From the International Searching Authority Re. Application No. PCT/IL2013/051089.

International Search Report and the Written Opinion dated Apr. 9, 2014 From the International Searching Authority Re. Application No. PCT/IL2013/051088.

Aoki et al. "Diffusion Coefficients in Viscous Sodium Alginate Solutions", Department of Applied Physics, University of Fukui, Japan, p. 1-23, Aug. 10, 2012.

Balkrishnan et al. "Self-Cross-Linking Biopolymers as injectable In Situ Forming Biodegradable Scaffolds", Biomaterials, 26: 3941-3951, 2005.

De Abajo et al. "Acute and Clinically Relevant Drug-Induced Liver Injury: A Population Based Case-Control Study", British Journal of Clinical Pharmacology, 58(1): 71-80, 2004.

Dvir-Ginzberg et al. "Liver Tissue Engineering Within Alginate Scaffolds: Effects of Cell-Seeding Density on Hepacyte Viability, Morphology, and Function", Tissue Engineering, 9(4): 757-766, 2003.

Earle et al. "Hepatectomy Enables Prolonged Survival in Select Patients With Isolated Noncolorectal Liver Metastasis", Journal of the American College of Surgeons, 203: 436-446, 2006.

Geller et al. "Outcome of 1000 Liver Cancer Patients Evaluated at the UPMC Liver Cancer Center", Presented at the 2005 American Hepato-Pancreato-Biliary Association Congress, Hollywood, Florida, USA, Apr. 14-17, 2005, 2005 AHPBA Annual Meeting, Journal of Gastrointestinal Surgery, 10(1): 63-68, Jan. 2006.

Ichi et al. "Increase of Ceramide in the Liver and Plasma After Carbon Tetrachloride Intoxication in the Rat", Journal of Nutritional Science and Vitaminology, 53(1): 53-56, Feb. 2007.

Kaplowitz "Drug-Induced Liver Injury", Clinical Infectious Diseases, CID, 38(Suppl.2): S44-S48, 2004.

Khotimchenko et al. "Healing and Preventive Effects of Calcium Alginate on Carbon Tetrachloride Induced Liver Injury in Rats", Marine Drugs, 2: 108-122, 2004. Abstract, p. 113, 115-116.

Kubota et al. "Measurement of Liver Volume and Hepatic Functional Reserve as a Guide to Decision-Making in Resectional Surgery for Hepatic Tumors", Hepatology, 26: 1176-1181, 1997.

Landa et al. "Effect of Injectable Alginate Implant on Cardiac Remodeling and Function After Recent and Old Infarcts in Rat", Circulation, 117: 1388-1396, Mar. 3, 2008.

Madoff et al. "Portal Vein Embolization on Preparation for Major Hepatic Resection: Evolution of A New Standard of Care", Journal of Vascular and Interventional Radiology, 16(6): 779-790, Jun. 2005.

Maruyama et al. "Duration of Liver Ischemia and Hepatic Regeneration After Hepatectomy in Rats", Journal of Surgical Research, 58: 290-294, 1995.

Mirshafiey et al. "Sodium Alginate as a Novel Therapeutic Option in Experimental Colitis", Scandinavian Journal of Immunology, 61: 316-321, 2005.

Razavi et al. "Therapeutic Effect of Sodium Alginate in Experimental Chronic Ulcerative Colitis", Iranian Journal of Allergy, Asthma and Immunology, 7(1): 13-18, Mar. 2008.

Seifert et al. "Production of Small, Monodispersed Alginate Beads for Cell Immobilization", Biotechnology Progress, 13: 582-568, 1997.

Tajiri et al. "Practical Guidelines for Diagnosis and Early Management of Drug Induced Liver Injury", World Journal of Gastroenterology, 14(44): 6774-6785, Nov. 28, 2008.

Tsur-Gang et al. "The Effects of Peptide-Based Modification of Alginate on Left Ventricular Remodeling and Function After Myocardial Infarction", Biomaterials, 30: 189-195, 2009.

Official Action dated Dec. 16, 2016 From the US Patent and Trademark Office Re. U.S. Appl. No. 14/758,603. (31 pages).

Chang et al. "Review Article: Drug Hepatotoxicity", Alimentary Pharmacology and Therapeutics, 25(10): 1135-1151, 2007.

Wojtczak "Glossary of Medical Education Terms", Institute for International Medical Education, 5 Pages, Dec. 2000.

(56) References Cited

OTHER PUBLICATIONS

Official Action dated Jun. 9, 2017 From the US Patent and Trademark Office Re. U.S. Appl. No. 14/758,603. (21 pages).
Wilkinson "Pharmacokinetics: The Dynamics of Drug Absorption, Distribution, and Elimination", In: Goodman and Gilman's The Pharmacological Basis of Therapeutics. 10th edition, Mc Grow Hill, 2001: pp. 23-26.
Communication Pursuant to Article 94(3) EPC dated Jun. 14, 2017 From the European Patent Office Re. Application No. 13869503.6. (6 Pages).
Communication Pursuant to Article 94(3) EPC dated Jun. 19, 2017 From the European Patent Office Re. Application No. 13869473.2. (7 Pages).
Communication Pursuant to Article 94(3) EPC dated Mar. 13, 2018 From the European Patent Office Re. Application No. 13869473.2. (5 Pages).
Communication Pursuant to Article 94(3) EPC dated Mar. 20, 2018 From the European Patent Office Re. Application No. 13869503.6. (6 Pages).
Liu et al. "Pharmacokinetics of Doxorubicin Alginate Microspheres and Evaluation of Its Hepatic Arterial Embolization In Vivo", Yao Xue Xue Bao = Acta Pharmaceutica Sinica, 41(8): 778-783, Aug. 2006. Abstract.
Remel "Phosphate Buffer (Butterfield's Buffer)", Remel, XP055457533, Retrieved From the Internet, Product Description, 1 P., Jun. 10, 2010.
Villay et al. "Comparison of Polysccharide Degradations by Dynamic High-Pressue Homogenization", Food Hydrocolloids, XP028352071, 27(2): 278-286, Jun. 2012.
Official Action dated Aug. 24, 2017 From the US Patent and Trademark Office Re. U.S. Appl. No. 14/758,603. (23 pages).
Office Action dated Nov. 27, 2017 From the Israel Patent Office Re. Application No. 239705 and Its Translation Into English. (9 Pages).
Office Action dated Nov. 27, 2017 From the Israel Patent Office Re. Application No. 239706 and Its Translation Into English. (11 Pages).
Restriction Official Action dated Nov. 2, 2018 From the US Patent and Trademark Office Re. U.S. Appl. No. 15/837,004. (8 pages).
Communication Pursuant to Article 94(3) EPC dated May 6, 2019 From the European Patent Office Re. Application No. 13869503.6. (4 Pages).
Office Action dated Apr. 8, 2019 From the Israel Patent Office Re. Application No. 239706. (5 Pages).
Official Action dated May 14, 2019 From the US Patent and Trademark Office Re. U.S. Appl. No. 15/837,004. (31 pages).

* cited by examiner

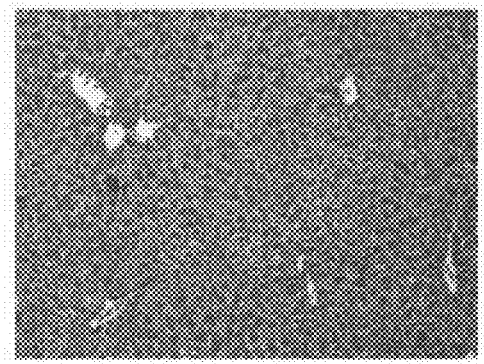 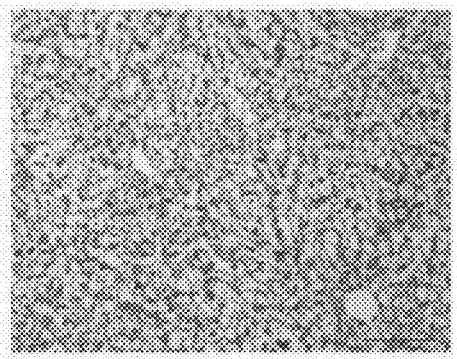
FIG. 17A  FIG. 17B
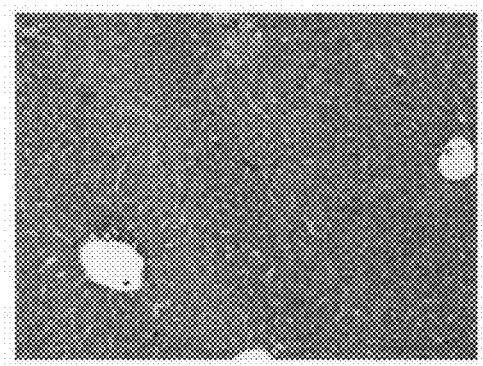 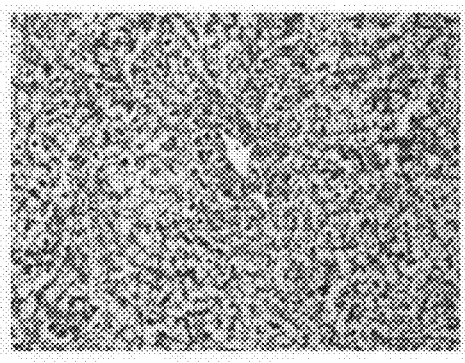
FIG. 17C  FIG. 17D

ALGINATE COMPOSITIONS AND USES THEREOF

RELATED APPLICATIONS

This application is a National Phase of PCT Patent Application No. PCT/IL2013/051089 having International filing date of Dec. 30, 2013, which claims the benefit of priority under 35 USC § 119(e) of U.S. Provisional Patent Application Nos. 61/747,328 filed on Dec. 30, 2012 and 61/747,325 filed on Dec. 30, 2012. The contents of the above applications are all incorporated by reference as if fully set forth herein in their entirety.

FIELD AND BACKGROUND OF THE INVENTION

The present invention, in some embodiments thereof, relates to biomaterials and, more particularly, but not exclusively, to novel alginate-based compositions, processes of preparing same and therapeutic uses thereof.

Alginate is an anionic polysaccharide derived from brown algae. Alginate is a linear block co-polymer of (1-4)-linked β-D-mannuronic acid (M) and α-L-guluronic acid (G). The monomers can appear in homopolymeric blocks of consecutive G-residues (G-blocks), consecutive M-residues (M-blocks), or alternating M- and G-residues (MG-blocks).

Sodium alginate is soluble in water, and, in the presence of divalent cations, such as calcium ions, alginate forms a hydrogel. In nature, alginate exists in both the soluble form and as a hydrogel. The hydrogel protects brown algae from stress caused by the hydrostatic pressure of water and by waves.

The ratio of mannuronic acid to guluronic acid (M/G) in alginate differs according to the type of algae, and according to environmental conditions. The G residues in alginate have a particularly high affinity to calcium ions. Consequently, the amount of G and length of G-sequences influences the extent of alginate crosslinking and the mechanical properties of the formed hydrogel.

In addition to diversity in M/G ratio, alginate may vary in molecular weight. In nature, alginate usually has a molecular weight in a range of 100-200 kDa. Using different treatment protocols, such as heat and γ-radiation, the molecular weight of alginate can be reduced. Alginates with molecular weights of approximately 50 kDa are commercially available.

International Patent Application PCT/IL97/00191 (published as WO 97/44070) describes implantable polysaccharide (e.g. alginate) sponges for use as a matrix, substrate or scaffold for the cultivation of mammalian cells in vitro prior to their implantation to replace damaged or removed tissue.

International Patent Application PCT/IL2004/000371 (published as WO 2004/098669) describes injectable cross-linked alginate, which forms a hydrogel in vivo, for use in the repair of cardiac tissue damage and ablation of cardiac arrhythmias, when locally applied onto the cardiac tissue.

International Patent Application PCT/IL2008/001552 (published as WO 2009/069131) describes treatment of hepatic disorders via administration of cross-linked or non-cross-linked alginate biomaterial. Local administration to the liver of alginate in solid, hydrogel or liquid form is described, as well as systemic administration by injection of alginate in liquid form.

Landa, N. et al. [*Circulation* 117:1388-1396 (2008)] describes calcium-crosslinked alginate in an injectable low-viscosity solution, which can undergo phase to transition into a hydrogel after injection. Injection of the alginate solution into a cardiac infarct was reported to prevent adverse cardiac remodeling and dysfunction.

Low-viscosity sodium alginate has been reported to reduce colonic damage and levels of the cytokines IL-6, TNF-α and the eicosanoids LTB4 and PGE2 in a rat model of acute ulcerative colitis induced by intracolonic administration of acetic acid [Mirshafiey et al., *Scand J Immunol*, 61:316-321 (2005)].

Orally administered calcium alginate (403 kDa) has been reported to reduce liver damage caused by ingestion of $CCl_4$ for one week in mice [Khotimchenko & Khotimchenko, *Mar Drugs* 2:108-122 (2004)].

Tsur-Gang et al. [*Biomaterials* 30:189-195 (2009)] describes modification of alginate with the adhesion peptide RGD in order to cause alginate to better interdigitate with the host. RGD-modified alginate is also described in International Patent Application PCT/IL2004/000371 (published as WO 2009/069131).

Liver disease represents a worldwide health problem in humans, which can be managed pharmacologically in only a few cases. Development of new drugs depends primarily on the availability of suitable animal models. The pathophysiology of liver disease includes complex phenomena such as interrelationships on humoral basis, the highly sophisticated morphological organization of the organ itself, and the integrity of metabolic and immunologic pathways and their regulation in the individual cell types of the liver.

The liver is responsible for the synthesis of serum proteins; intermediary metabolism of amino acids, lipids, and carbohydrates; and detoxification of foreign compounds. These functions are usually seriously hampered in the various animal models of liver diseases.

Partial hepatectomy in humans is often needed and well tolerated in the setting of primary of secondary liver tumors [Geller et al. *J Gastrointest Surg* 10:63-68 (2006)]. Nevertheless, there are cases in which extended partial hepatectomy is warranted due to large hepatic mass and pose a high risk for fulminant hepatic failure [Kubota et al. *Hepatology* 26:1176-81 (1997)]. To avoid a need for liver transplantation, innovative therapies such as portal vein embolization and staged liver resections have been both used, but have been shown to be associated with considerable morbidity and mortality [Madoff et al. *J Vasc Interv Radiol* 16:779-790 (2005); Earle et al. *J Am Coll Surg* 203:436-446 (2006)].

Autoimmune hepatitis is commonly treated by immune suppression, using steroids and immune-modulators for long periods of time (e.g., 3 years). This treatment has significant potential side effects.

Liver damage induced by hepatitis C virus (HCV) is immune-mediated, as HCV is a non-cytopathic virus.

More than 900 drugs have been implicated in causing liver injury [Friedman et al. (2003), *Current Diagnosis & Treatment in Gastroenterology*, New York: Lang Medical Books/McGraw-Hill. pp. 664-679]. Hepatotoxicity is the most common reason for a drug to be withdrawn from the market, and also accounts for a substantial number of compound failures during drug development. Drug-induced liver injury (DILI) is responsible for 5% of all hospital admissions and 50% of all acute liver failures. Liver function tests are routinely used to monitor subjects taking any of a variety of drugs (e.g., methotrexate, carbamazepine).

Paracetamol (acetaminophen; APAP) intoxication, which may be intentional or unintentional, is one of the major causes of death from drug overdose and may lead to acute liver failure, sometimes irreversibly. Paracetamol-induced liver toxicity is the most prevalent cause of acute liver failure in the Western world. Currently, an accepted treatment is N-acetylcysteine administration, which has several drawbacks, mainly due to its limited therapeutic window.

Knowledge of the mechanisms of paracetamol hepatotoxicity derives to a large extent from studies performed in mice treated with paracetamol. In mice, covalent binding of APAP metabolites to liver proteins begins within 15 minutes of the overdose, concurrently with the beginning of glutathione depletion, and peaks within 1-2 hours. This is followed by other pathogenetic events such as disturbance of intracellular calcium homeostasis, oxidative and nitrosative stress, massive hepatic congestion, and activation of the innate immunity including natural-killer and natural-killer cells with T-cell receptors, macrophages and neutrophils. Oncotic necrosis is the main mode of hepatocyte cell death.

Alcoholic liver disease is the major cause of liver disease in Western countries. Chronic consumption of alcohol results in the secretion of pro-inflammatory cytokines (TNF-α, IL-6 and IL-8), oxidative stress, lipid peroxidation, and acetaldehyde toxicity. These factors cause inflammation, apoptosis and eventually fibrosis of liver cells.

Additional art includes International Patent Application Publication WO 95/19743; International Patent Application Publication WO 98/12228; International Patent Application Publication WO 2004/082594; German Patent Application Publication DE 19723155 A1; Ichi et al. [*J Nutr Sci Vitaminol* 53:53-56 (2007)]; Seifert & Phillips [Biotechnol Prog 13:562-568 (1997)]; Balakrishnan & Jayakrishnan [Biomaterials 26:3941-3951 (2005)]; Maruyama et al. [*J Surg Res* 58:29-294 (1995)]; and Dvir-Ginzberg et al. [*Tissue Engineering* 9:757-766 (2003)].

SUMMARY OF THE INVENTION

According to an aspect of some embodiments of the invention, there is provided a composition comprising an alginate, a source of sodium ions and a carrier, the alginate in the composition being characterized by at least one of:

(i) a zeta potential weaker than −25 mV, at a concentration of 0.5% (w/v) alginate in the carrier; and (ii) a diffusion coefficient of at least $10^{-8}$ cm$^2$/second, at a concentration of 0.5% (w/v) alginate in the carrier.

According to an aspect of some embodiments of the invention, there is provided a method of treating a hepatic disease or disorder, the method comprising administering to a subject in need thereof a therapeutically effective amount of the composition described herein, thereby treating the disease or disorder.

According to an aspect of some embodiments of the invention, there is provided a method of preventing or reducing liver damage caused by a hepatotoxic agent, the method comprising administering to a subject in need thereof an effective amount (e.g., a therapeutically effective amount) of the composition described herein, thereby preventing or reducing liver damage.

According to an aspect of some embodiments of the invention, there is provided a method of treating a medical condition treatable by a hepatotoxic agent in a subject in need thereof, the method comprising co-administering to the subject the hepatotoxic agent and an effective amount (e.g., a therapeutically effective amount) of the to composition described herein, thereby treating the medical condition.

According to an aspect of some embodiments of the invention, there is provided a method of treating a medical condition selected from the group consisting of the medical conditions listed in Table 1 (right column) herein in a subject in need thereof, the method comprising co-administering to the subject a hepatotoxic agent selected from the group consisting of the hepatotoxic drugs listed in Table 1 (left column) herein, the aforementioned hepatotoxic drug being respective to the aforementioned condition, and an effective amount (e.g., a therapeutically effective amount) of the composition described herein, thereby treating the medical condition.

According to an aspect of some embodiments of the invention, there is provided a use of the composition described herein in the manufacture of a medicament for treating a hepatic disease or disorder.

According to an aspect of some embodiments of the invention, there is provided a use of the composition described herein in the manufacture of a medicament for preventing or reducing liver damage caused by a hepatotoxic agent.

According to an aspect of some embodiments of the invention, there is provided a use of the composition described herein in the manufacture of a medicament for treating a medical condition treatable by a hepatotoxic agent, the treating comprising co-administering the hepatotoxic agent and an effective amount (e.g., a therapeutically effective amount) of the alginate.

According to an aspect of some embodiments of the invention, there is provided a use of the composition described herein in the manufacture of a medicament for treating a medical condition selected from the group consisting of the medical conditions listed in Table 1 (right column) herein, the treating comprising co-administering a therapeutically effective amount of a hepatotoxic agent selected from the group consisting of the hepatotoxic drugs listed in Table 1 (left column) herein, the aforementioned hepatotoxic drug being respective to the aforementioned condition, and an effective amount (e.g., a therapeutically effective amount) of the alginate.

According to an aspect of some embodiments of the invention, there is provided a process for preparing the composition described herein, the process comprising contacting the alginate and a carrier comprising a source of sodium ions, and homogenizing the alginate and the carrier.

According to an aspect of some embodiments of the invention, there is provided a process for preparing an alginate composition, the process comprising contacting an alginate and a carrier comprising a source of sodium ions, and homogenizing the alginate and the carrier using a mixing frequency of at least 10,000 per minute for at least 20 seconds.

According to an aspect of some embodiments of the invention, there is provided an alginate composition formed by a process described herein.

According to an aspect of some embodiments of the invention, there is provided a method of treating an inflammatory bowel disease, the method comprising administering to a subject in need thereof a therapeutically effective amount of the composition described herein, thereby treating the inflammatory bowel disease.

According to an aspect of some embodiments of the invention, there is provided a use of the composition described herein in the manufacture of a medicament for treating an inflammatory bowel disease.

According to some embodiments of the invention, the carrier is a pharmaceutically acceptable carrier.

According to some embodiments of the invention, the composition is a pharmaceutical composition, wherein the carrier is a pharmaceutically acceptable carrier.

According to some embodiments of the invention, the alginate has a molecular weight in a range of from 10 to 75 kDa.

According to some embodiments of the invention, the molecular weight is in a range of from 30 to 50 kDa.

According to some embodiments of the invention, a concentration of the alginate is in a range of from 0.4% to 10% (w/v).

According to some embodiments of the invention, the composition is further characterized by a solution viscosity in a range of from 3 to 20 mPa*seconds, at a shear rate of 1 second$^{-1}$ and at a concentration of 2% (w/v) alginate in the carrier.

According to some embodiments of the invention, the solution viscosity is in a range of from 10 to 20 mPa*seconds.

According to some embodiments of the invention, the solution viscosity is in a range of from 10 to 20 mPa*seconds, and the molecular weight is in a range of from 30 to 50 kDa.

According to some embodiments of the invention, the zeta potential is weaker than −20 mV, at a concentration of 0.5% (w/v) alginate in the carrier.

According to some embodiments of the invention, the diffusion coefficient is at least $10^{-7}$ cm$^2$/second, at a concentration of 0.5% (w/v) alginate in the carrier.

According to some embodiments of the invention, the composition is for use in treating a hepatic disease or disorder.

According to some embodiments of the invention, the composition is for use in preventing or reducing liver damage caused by a hepatotoxic agent.

According to some embodiments of the invention, the composition is for use in treating a medical condition treatable by a hepatotoxic agent, the treating comprising co-administering a therapeutically effective amount of the hepatotoxic agent and an effective amount (e.g., a therapeutically effective amount) of the alginate.

According to some embodiments of the invention, the composition is for use in treating a medical condition selected from the group consisting of the medical conditions listed in Table 1 (right column) herein, the treating comprising co-administering a therapeutically effective amount a hepatotoxic agent selected from the group consisting of the hepatotoxic drugs listed in Table 1 (left column) herein, the aforementioned hepatotoxic drug being respective to the aforementioned condition, and an effective amount (e.g., a therapeutically effective amount) of the alginate.

According to some embodiments of the invention, the disease or disorder is selected from the group consisting of non-alcoholic steatohepatitis (NASH), non-alcoholic fatty liver disease (NAFLD), alcoholic liver disease, a hepatectomy-related disease or disorder, liver damage induced by a hepatotoxic agent, a viral hepatitis, an immune-mediated liver disease, a graft-versus-host disease (GVHD) of the liver, a metabolic liver disease, a liver cancer, and an acute hepatic failure.

According to some embodiments of the invention, the liver damage induced by a hepatotoxic agent is a drug-induced liver injury (DILI).

According to some embodiments of the invention, administration of the composition is effected during a time period ranging from 100 minutes prior to exposure to the hepatotoxic agent to 50 minutes subsequent to exposure to the hepatotoxic agent.

According to some embodiments of the invention, the composition is co-administered with the hepatotoxic agent.

According to some embodiments of the invention, the composition further comprises a therapeutically effective amount of the hepatotoxic agent.

According to some embodiments of the invention, the composition is a unit dosage form.

According to some embodiments of the invention, administration of the composition is effected by systemic administration.

According to some embodiments of the invention, administration of the composition is effected by intraperitoneal administration.

According to some embodiments of the invention, administration of the composition is effected by oral administration.

According to some embodiments of the invention, the hepatotoxic agent is selected from the group consisting of ethanol, paracetamol, acarbose, amiodarone, bosentan, bromfenac, dantrolene, diclofenac, dihydralazine, disulfiram, felbamate, fluoxetine, halothane, isoniazid, kava, ketoconazole, labetalol, leflunomide, methotrexate, methyldopa, nefazodone, nicotinic acid, paroxetine, pemoline, propylthiouracil, pyrazinamide, rifampin, ritonavir, sertraline, statins, tacrine, tetracycline antibiotics, tolcapone, troglitazone, trovafloxacin, valproic acid, ximelagatran, zafirlukast, zileuton, anabolic steroids, azathioprine, azithromycin, captopril, cimetidine, ciprofloxacin, clopidogrel, dicloxacillin, erythromycin, estrogens, flucloxacillin, naproxen, phenobarbital, phenothiazine antipsychotics, phenytoin, sulindac, terbinafine, tricyclic antidepressants, amoxicillin-clavulanic acid, carbamazepine, cyclosporine, enalapril, flutamide, methimazole, nitrofurantoin, sulfonamides, trazodone, trimethoprim, verapamil, allopurinol, aspirin, betahistine, busulfan, cephalosporins, chlorpheniramine, clarithromycin, codeine, corticosteroids, cyclophosphamide, cytarabine, danazol, dihydrocodeine, fluconazole, hydralazine, indinavir, mahuang, mebeverine, metoclopramide, oxycodone, penicillamine, phenylbutazone, procainamide, quinidine, retinol, reverse transcriptase inhibitors, sulpiride, tamoxifen and telithromycin.

According to some embodiments of the invention, the hepatotoxic agent is paracetamol.

According to some embodiments of the invention, the composition is for use in to treating an inflammatory bowel disease.

According to some embodiments of the invention, the inflammatory bowel disease is selected from the group consisting of Crohn's disease, ulcerative colitis, microscopic colitis, idiopathic inflammation of the small and/or proximal intestine, irritable bowel syndrome, collagenous colitis, lymphocytic colitis, ischaemic colitis, diversion colitis, Behcet's disease and indeterminate colitis.

According to some embodiments of the invention, administration of the composition is effected by rectal administration.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a graph showing the intensity of small angle X-ray scattering (SAXS) as a function of the scattering vector (q), for 2% (w/v) VLVG alginate homogenized in saline (0.15 M NaCl) (circles) or dissolved in double distilled water without homogenization (triangles);

FIG. 2 is a cryogenic transmission electron microscopy image of a 2% solution of VLVG alginate non-homogenized in double-distilled water, showing multi-molecular alginate structures;

FIG. 3 is a bar graph showing serum ALT (alanine aminotransferase) activity in mice 6, 24 and 48 hours after administration of concanavalin A, following treatment with dexamethasone (Dex), 2% solutions of VLVG alginate, LVG150 alginate or LVG54 alginate homogenized in saline, or with saline control (cont) (*$p<0.05$, $p<0.005$, *$p<0.00005$ relative to control);

FIG. 4 is a bar graph showing serum albumin levels in mice 48 hours after administration of concanavalin A, following treatment with dexamethasone (Dex), 2% solutions of VLVG alginate, LVG150 alginate or LVG54 alginate homogenized in saline, or with saline control (cont) (*$p<0.01$, $p<0.002$, *$p<0.00007$ relative to control);

FIG. 5 is a bar graph showing serum interleukin-6 levels in mice 48 hours after administration of concanavalin A, following treatment with dexamethasone (Dex), 2% solutions of VLVG alginate, LVG150 alginate or LVG54 alginate homogenized in saline, or with saline control (*$p<0.02$ relative to control);

FIG. 6 is a bar graph showing serum interferon-γ (IFN-g) levels in mice 48 hours after administration of concanavalin A, following treatment with dexamethasone (Dex), 2% solutions of VLVG alginate, LVG150 alginate or LVG54 alginate homogenized in saline, or with saline control (*$p<0.002$ relative to control);

FIG. 7 is a bar graph showing serum ALT activity in mice 6, 24 and 48 hours after administration of concanavalin A, following treatment with dexamethasone (Dex), a 0.3% solution of hyaluronan (HA), a 2% solution of VLVG alginate homogenized in saline, or with saline control (saline, cont) (*$p<0.05$, $p<0.005$, *$p<0.001$ relative to control);

FIG. 8 is a bar graph showing serum albumin levels in mice 48 hours after administration of concanavalin A, following treatment with dexamethasone (Dex), a 0.3% solution of hyaluronan (HA), a 2% solution of VLVG alginate homogenized in saline, or with saline control (*$p<0.01$, **$p<0.001$ relative to control);

FIG. 9 is a bar graph showing serum ALT activity in mice 6, 24 and 48 hours after administration of concanavalin A, following treatment with dexamethasone (Dex), a 2% solution of biotinylated VLVG alginate homogenized in saline, or with saline control (*$p<0.03$, $p<0.001$, *$p<0.00005$ relative to control);

FIG. 10 is a bar graph showing serum albumin levels in mice 48 hours after administration of concanavalin A, following treatment with dexamethasone (Dex), a 2% solution of biotinylated VLVG alginate homogenized in saline, or with saline control (*$p=0.008$, **$p<0.005$ relative to control);

FIG. 11 is a bar graph showing serum ALT (alanine aminotransferase) activity in mice 6, 24 and 48 hours after administration of concanavalin A, following treatment with dexamethasone (Dex), 2% solutions of VLVG alginate or γ-irradiated LVG150 alginate (2% LVG (gamma radiation)) homogenized in saline, or with saline control (saline, cont) (*$p<0.05$, $p<0.0009$, *$p<0.0003$ relative to control);

Figure 12:
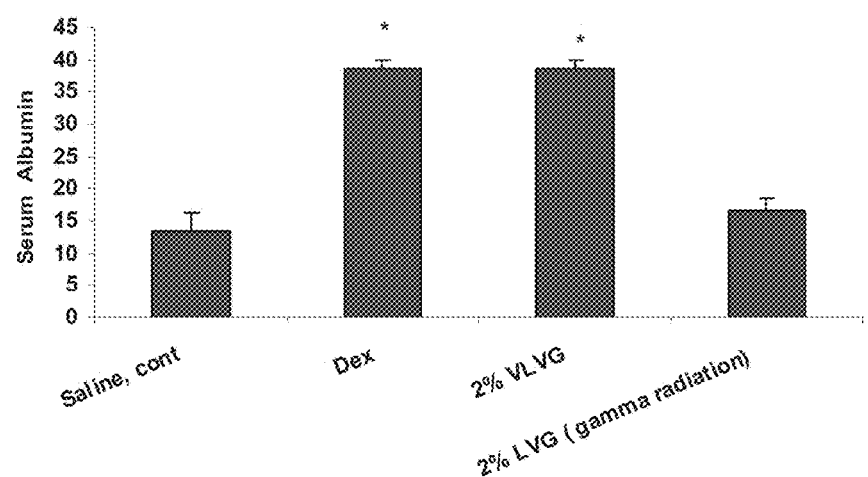
Figure 13:
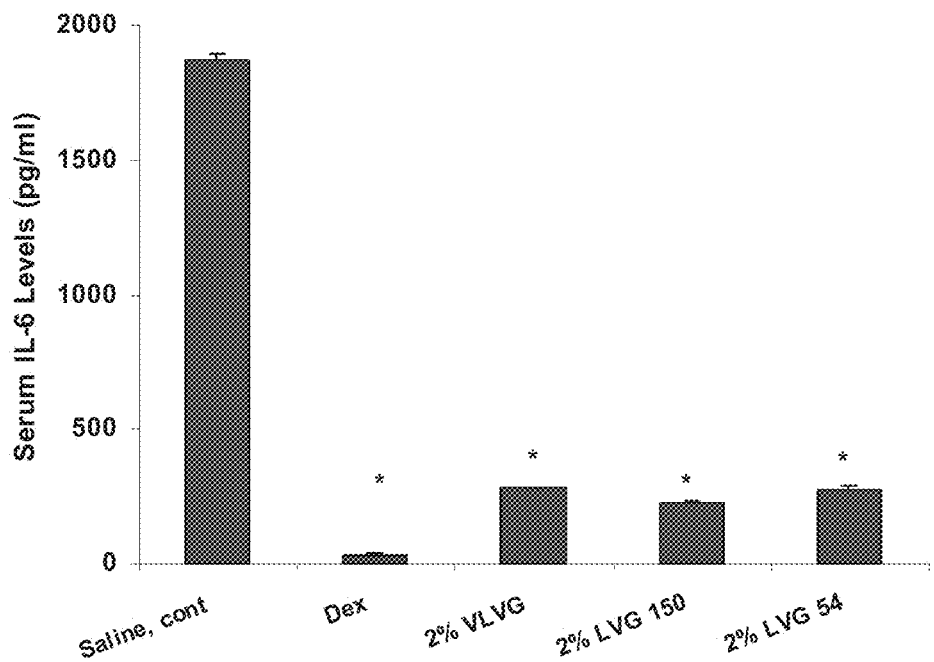
Figure 14:
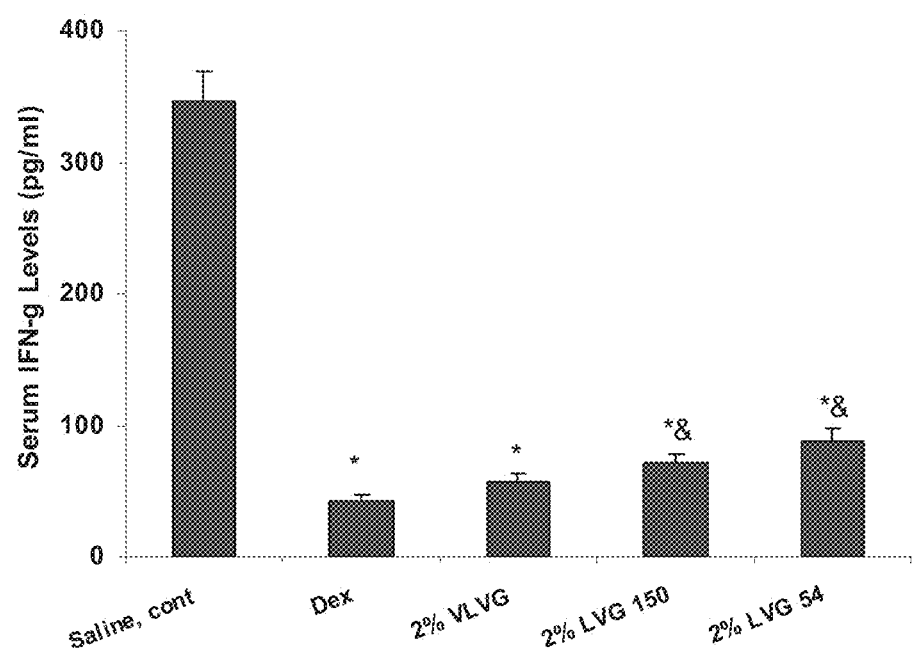
Figure 15:
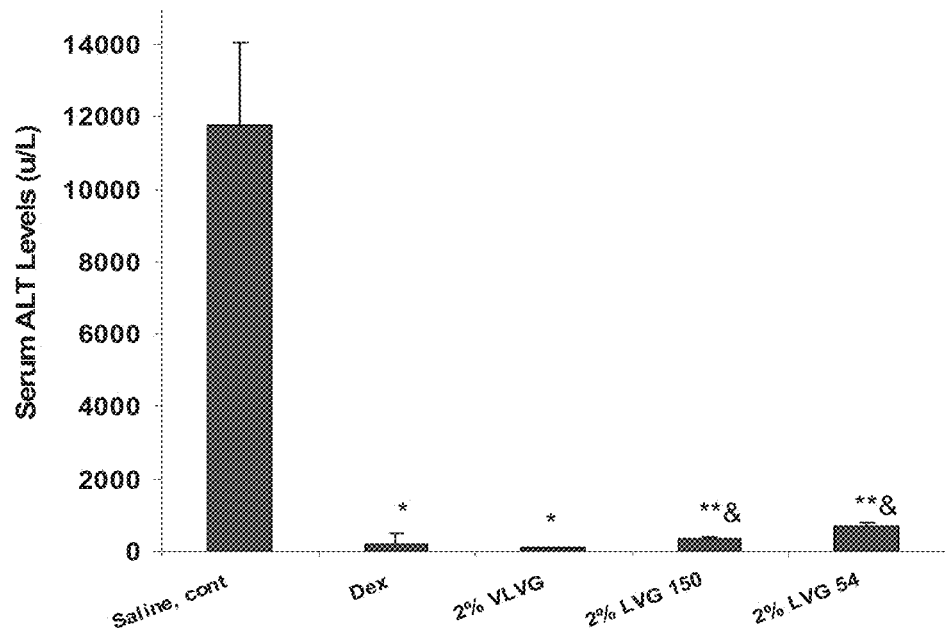
Figure 16:
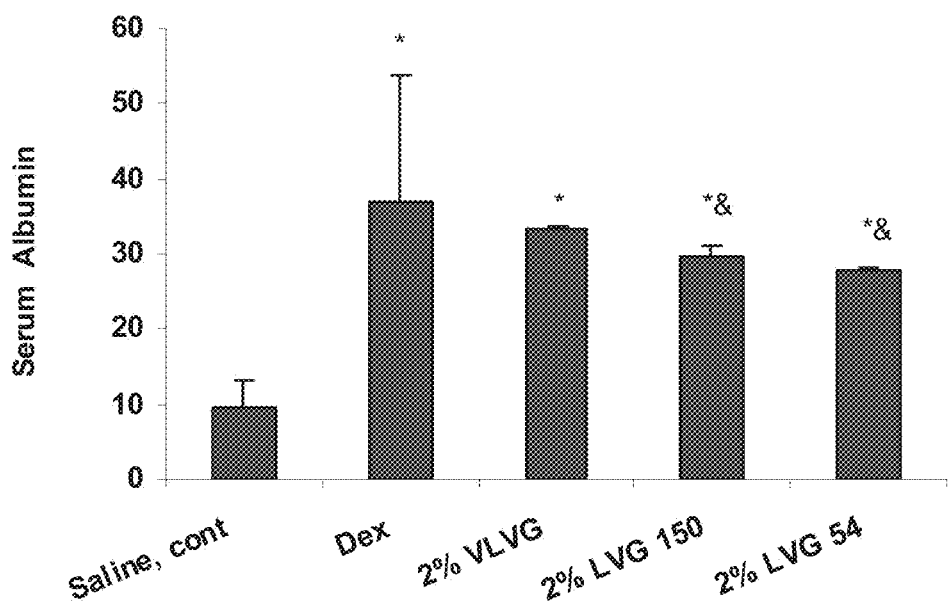
Figure 18:
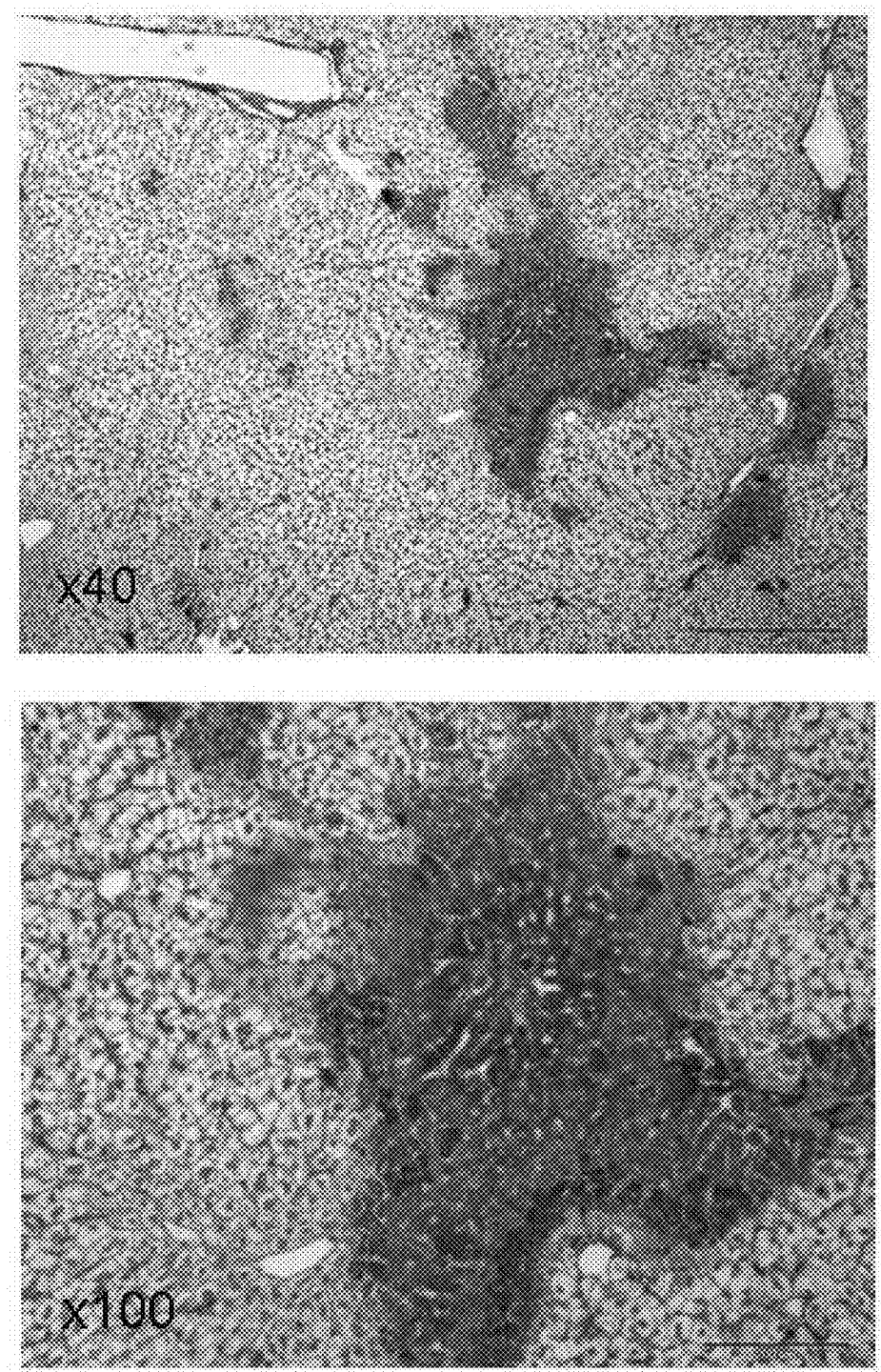
Figure 19A:
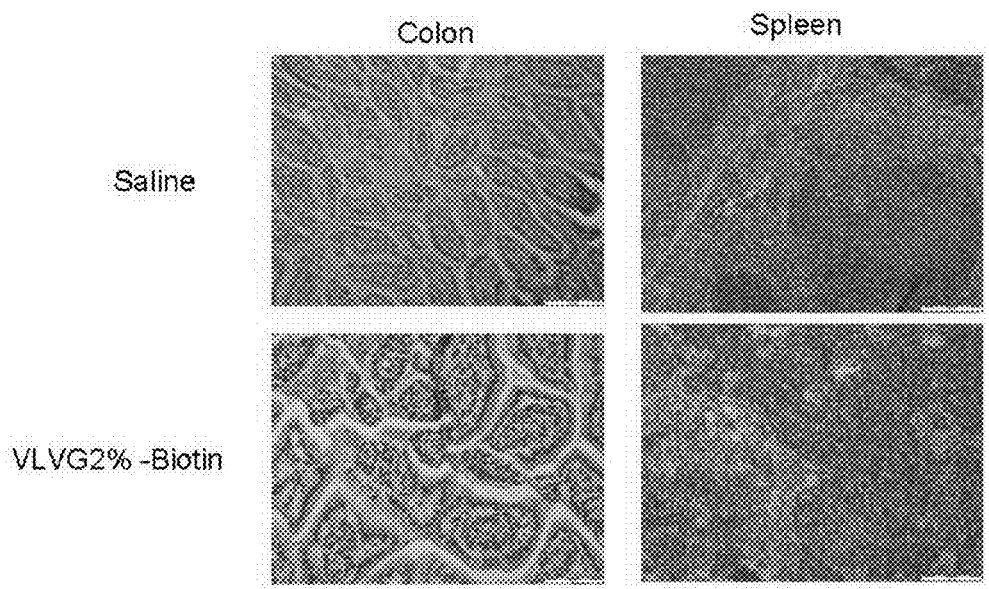
Figure 19B:
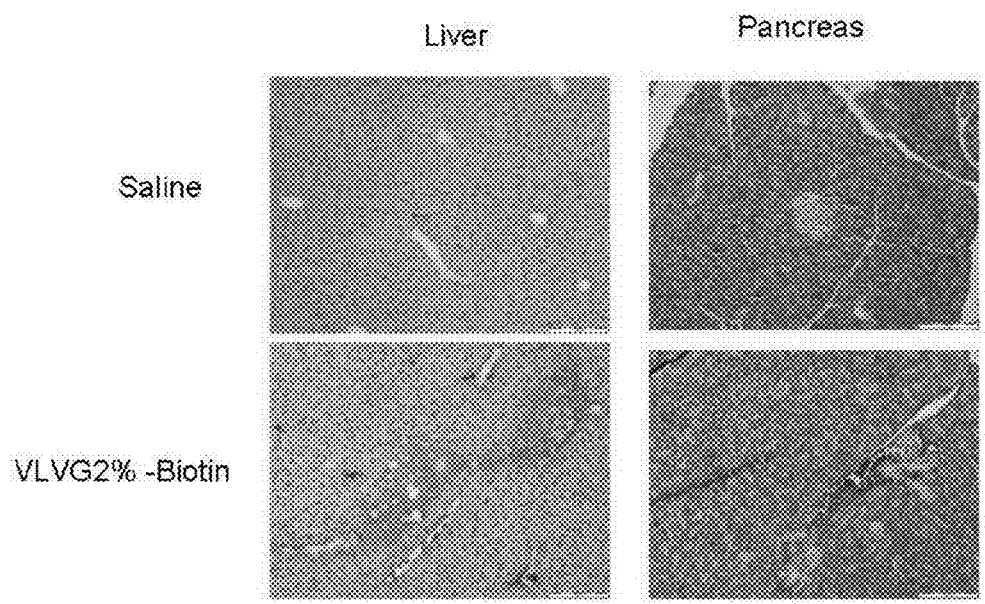
Figure 20:
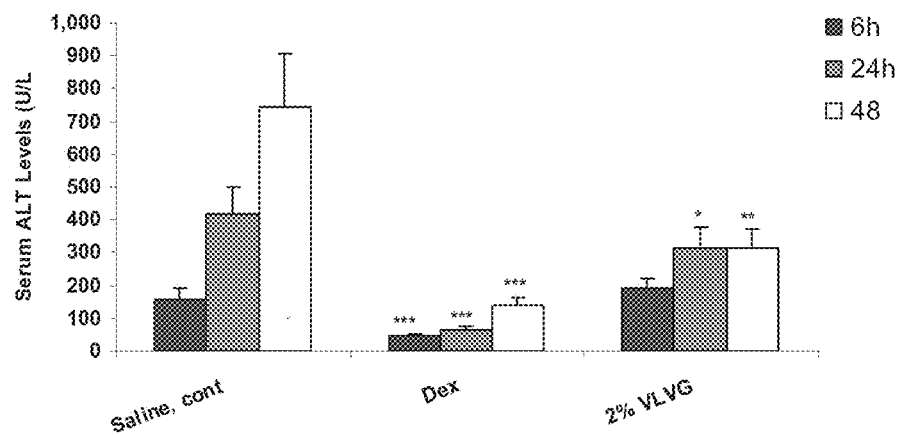
Figure 21:
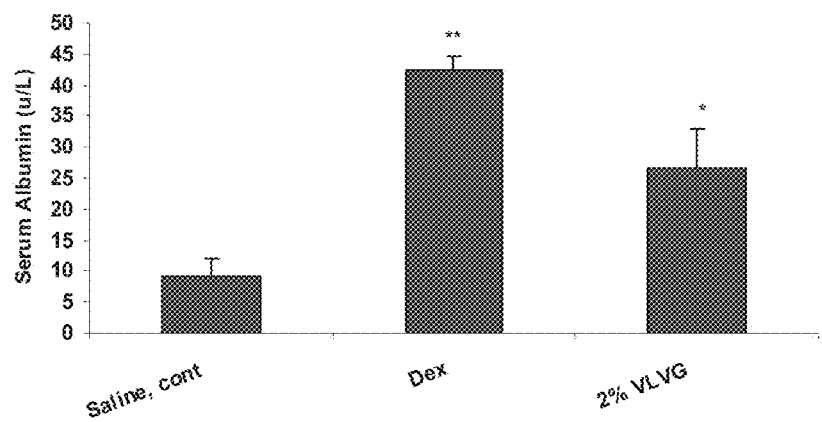
Figure 22:
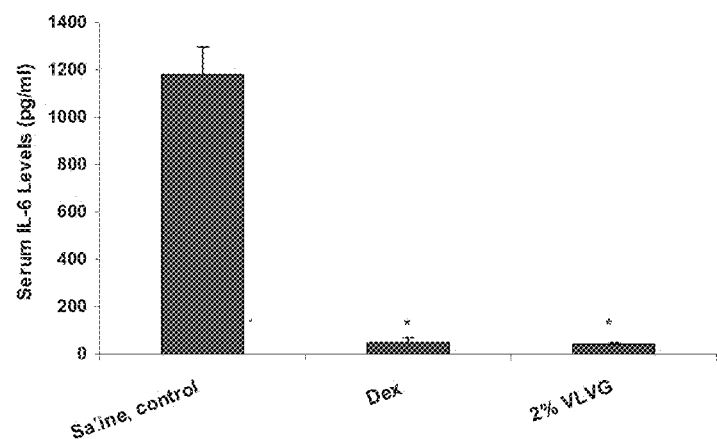
Figure 23:
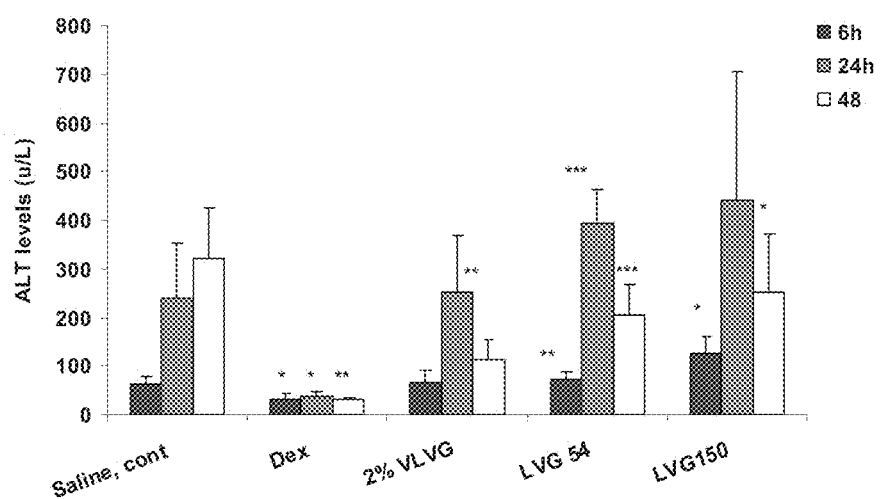
Figure 24:
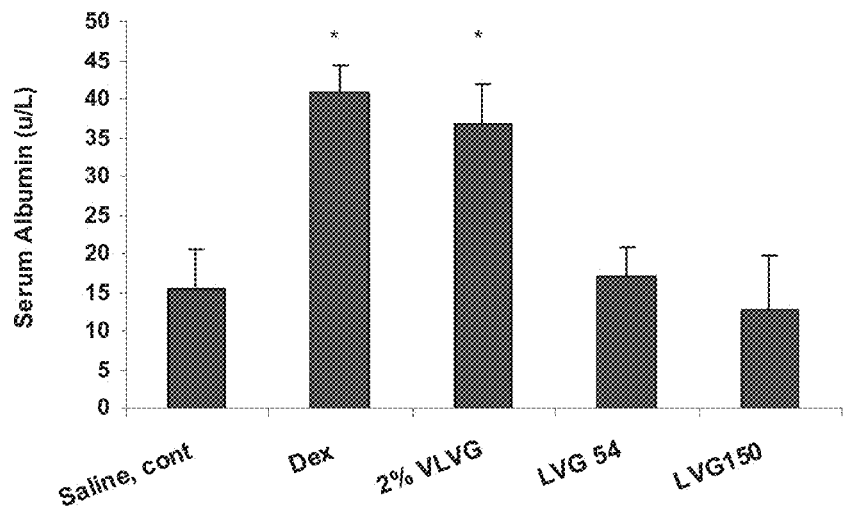
Figure 25:
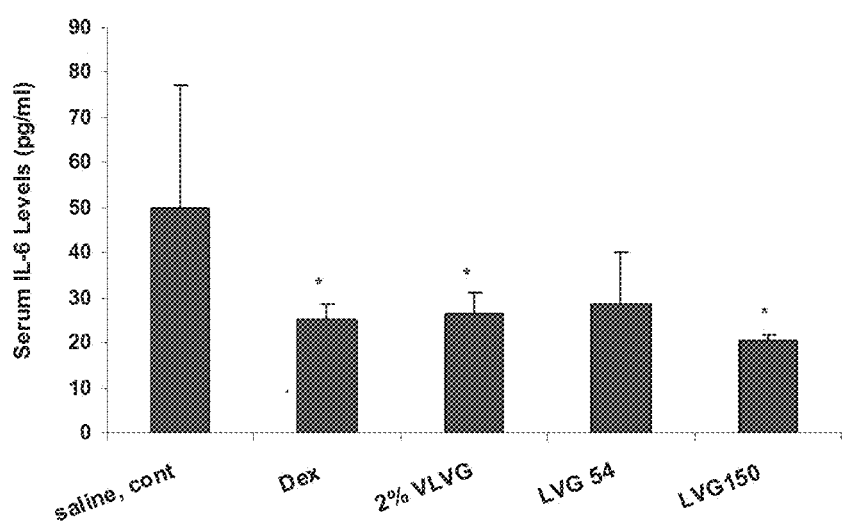
Figure 26:
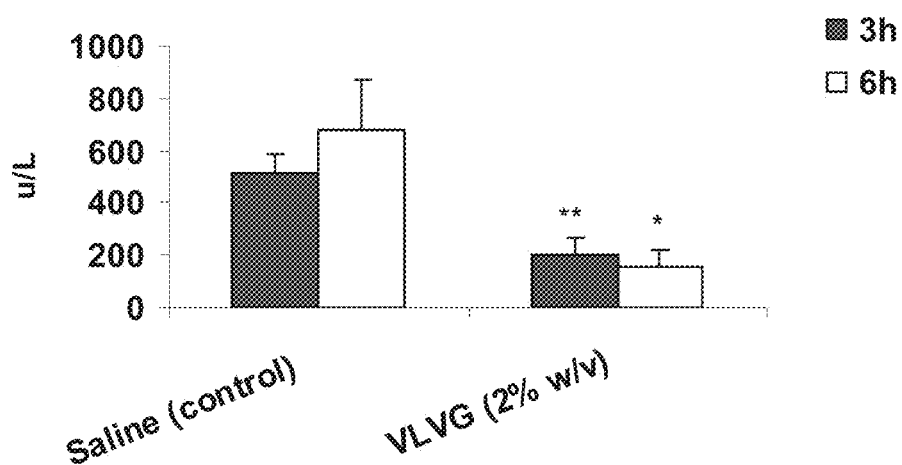
Figure 27:
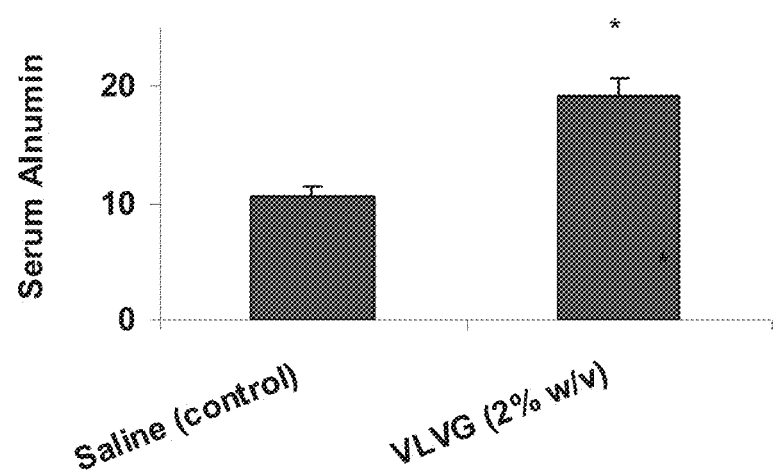
Figure 28:
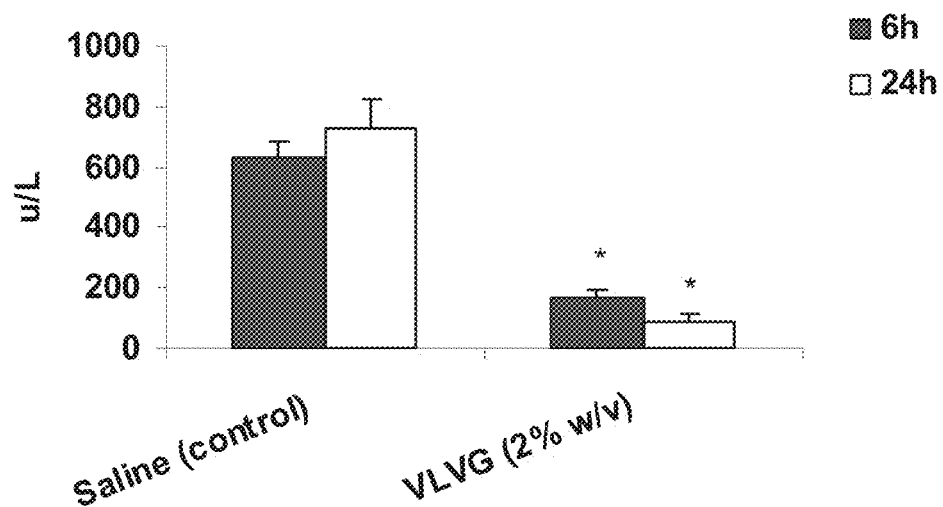
Figure 29:
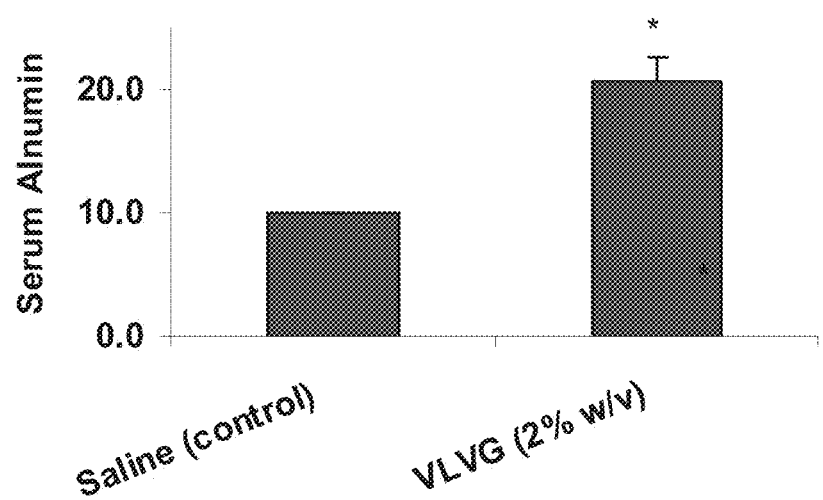
Figure 30:
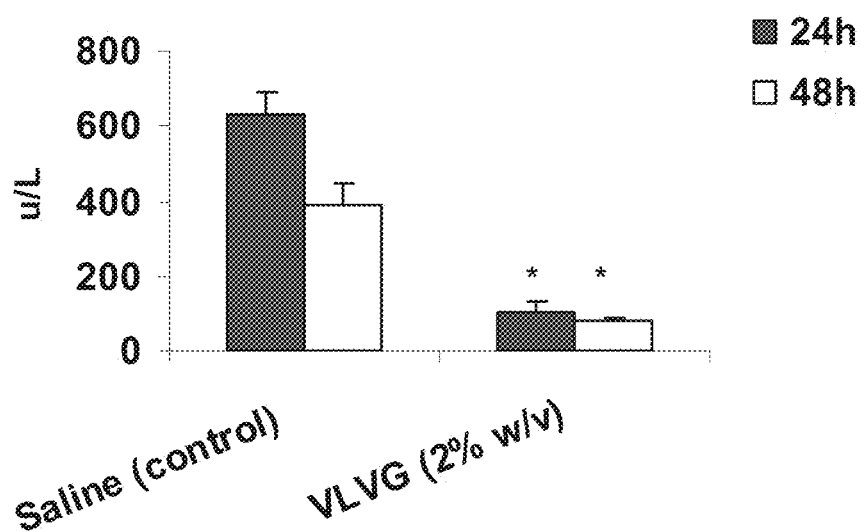
Figure 31:
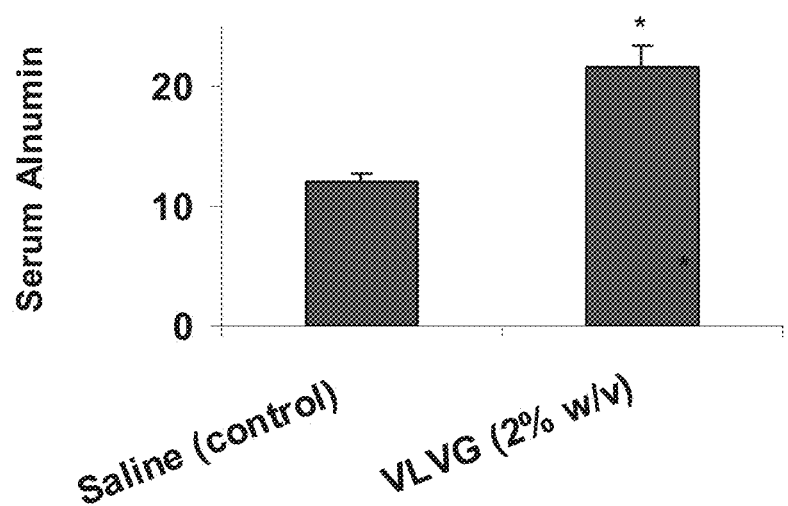
Figure 32:
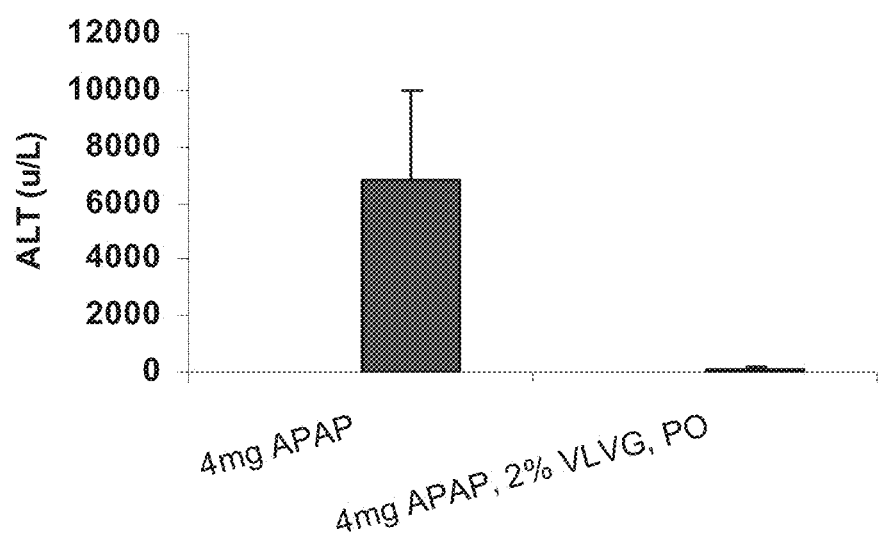
Figure 33A:
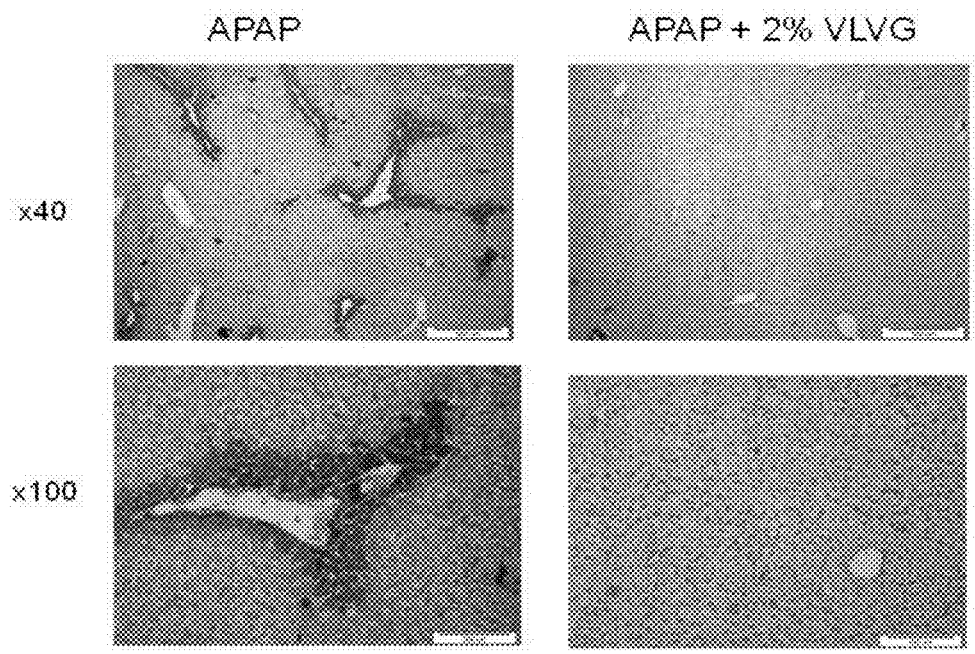
Figure 33B:
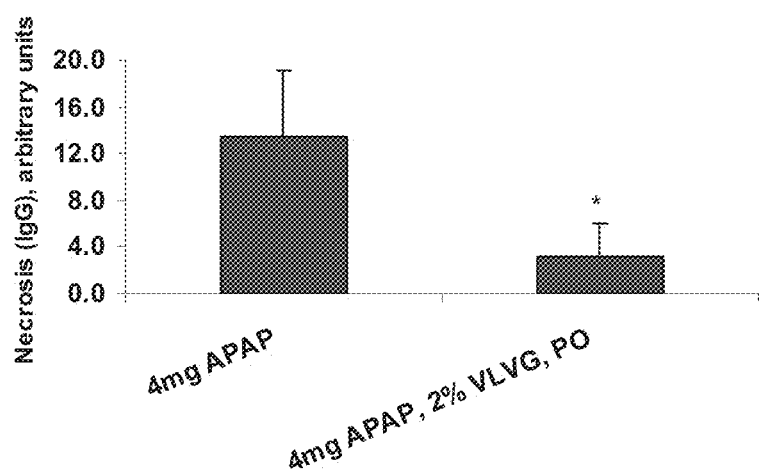
Figure 34:
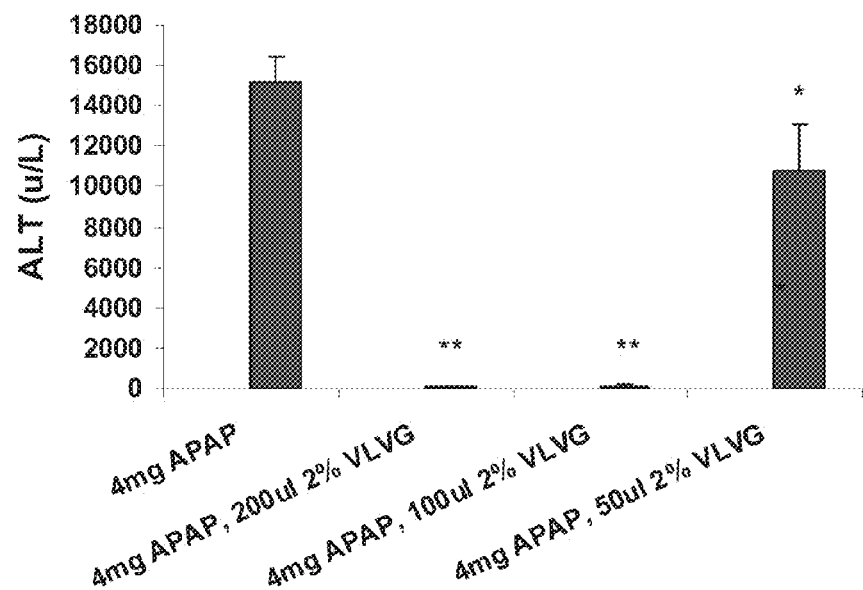
Figure 35:
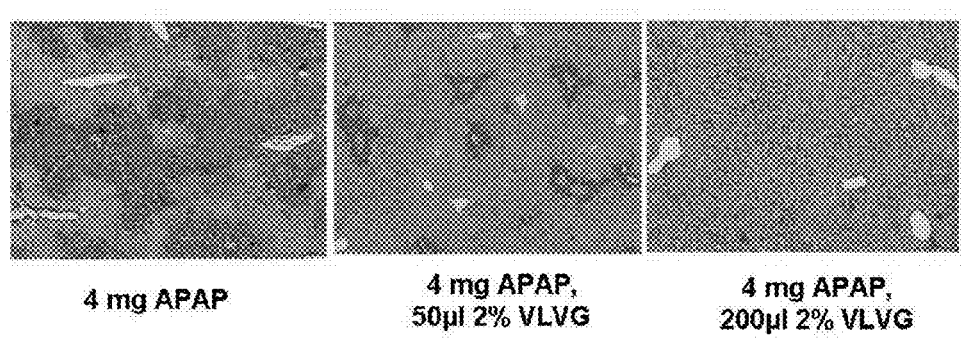
Figure 36:
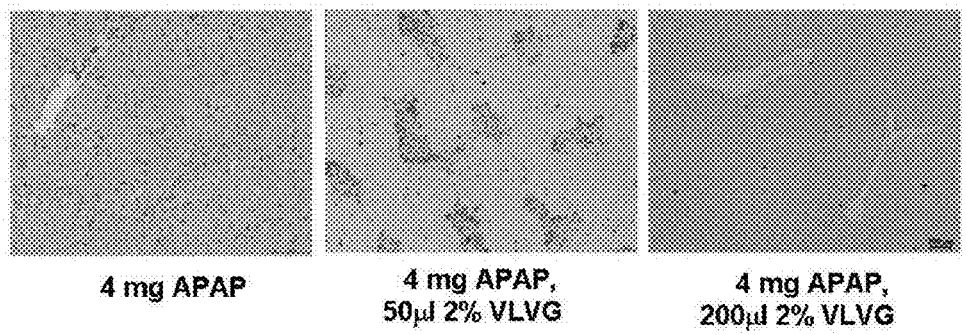
Figure 37:
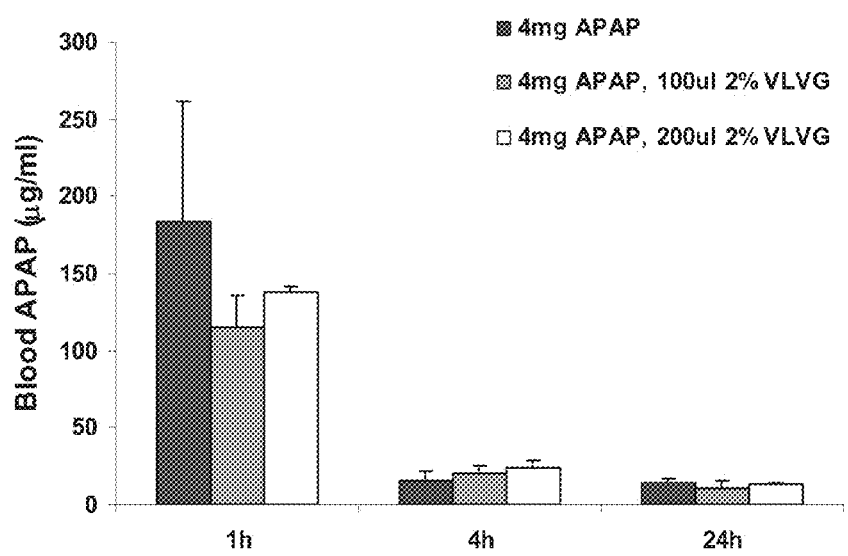
Figure 38:
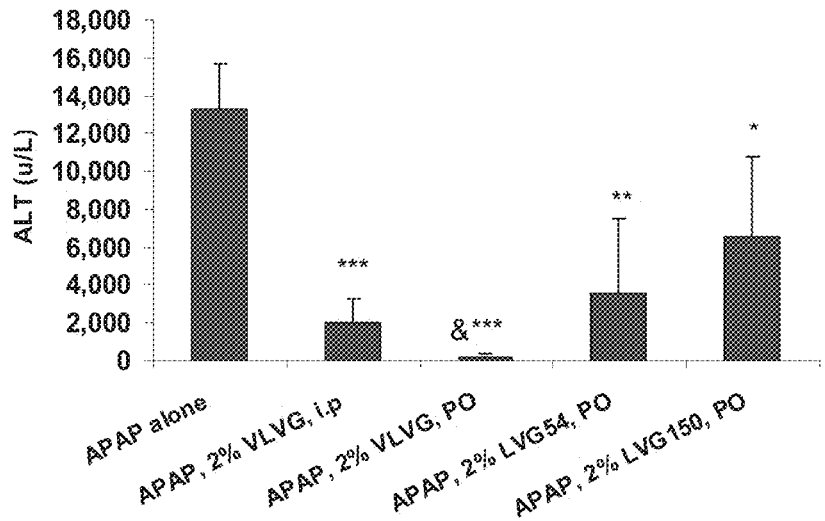
Figure 39:
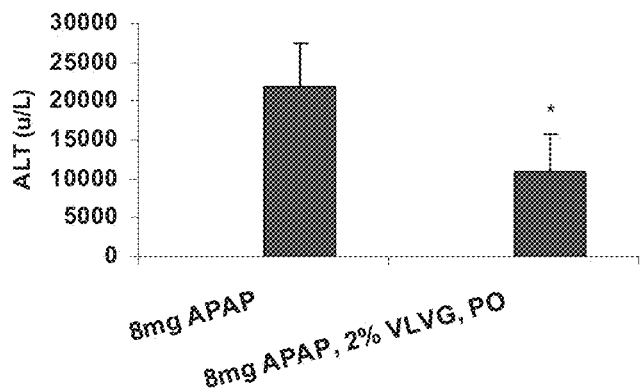
Figure 40:
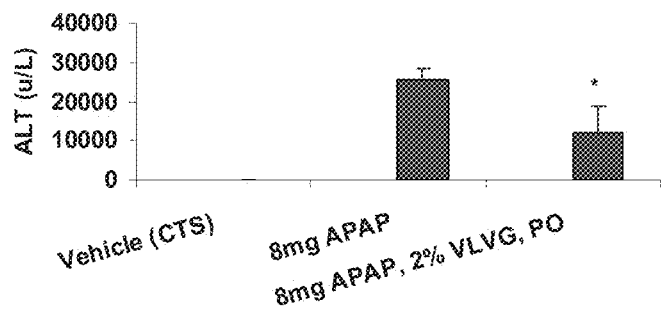
Figure 41:
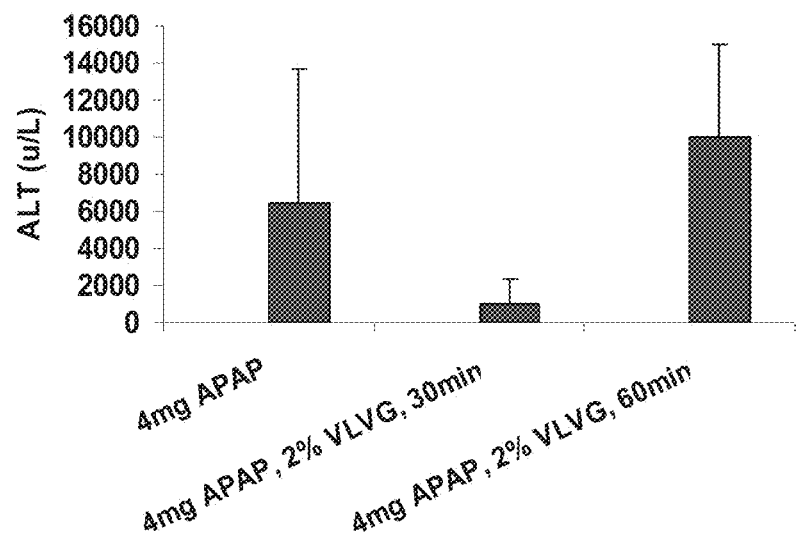
Figure 42:
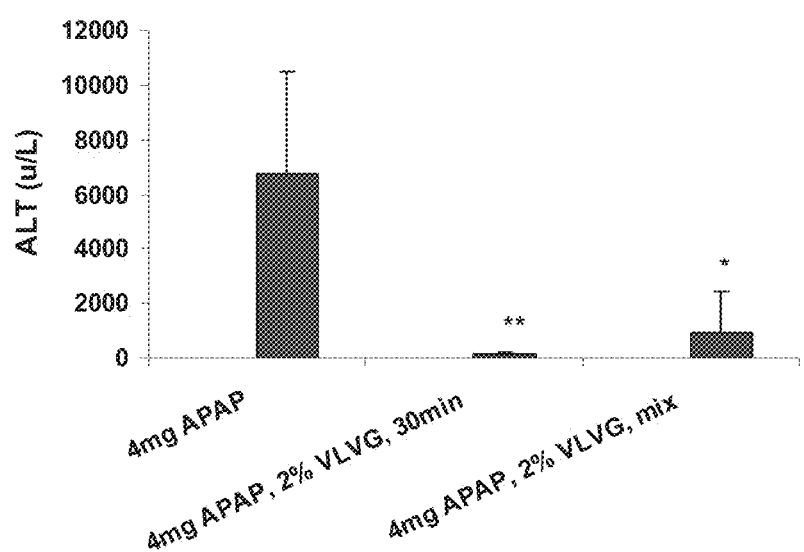
Figure 43:
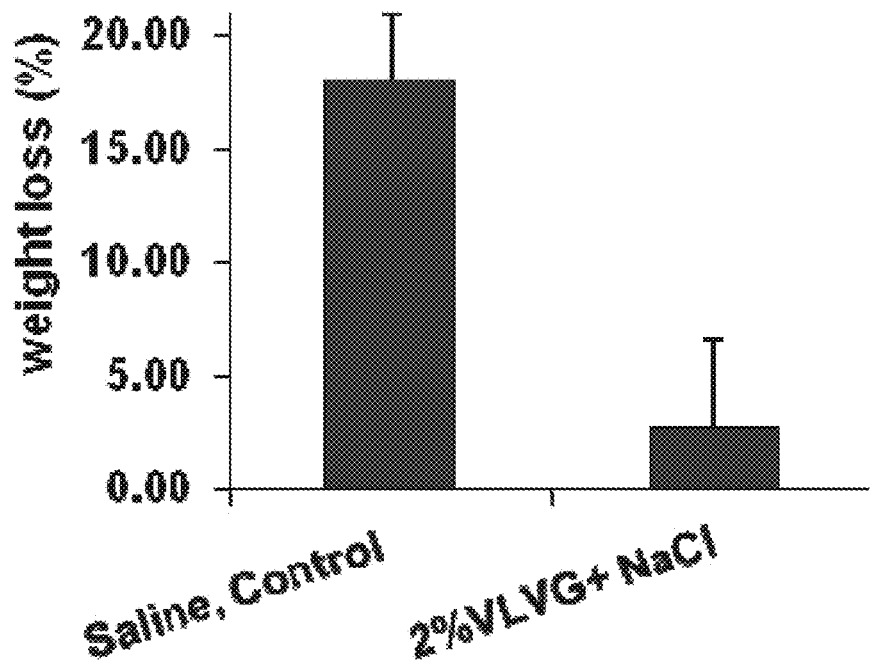
Figure 44:
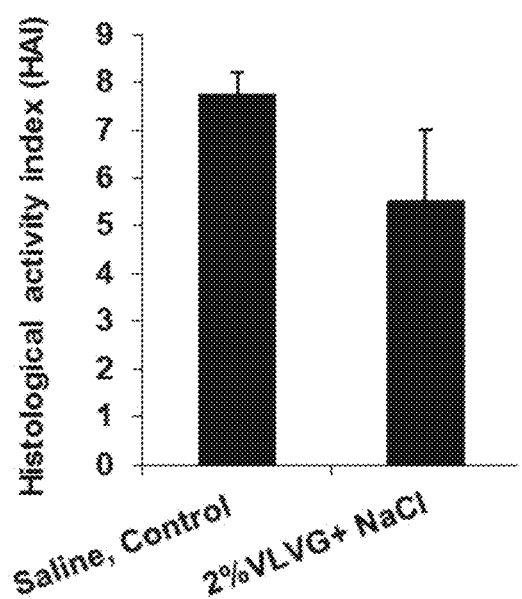
Figure 45A:
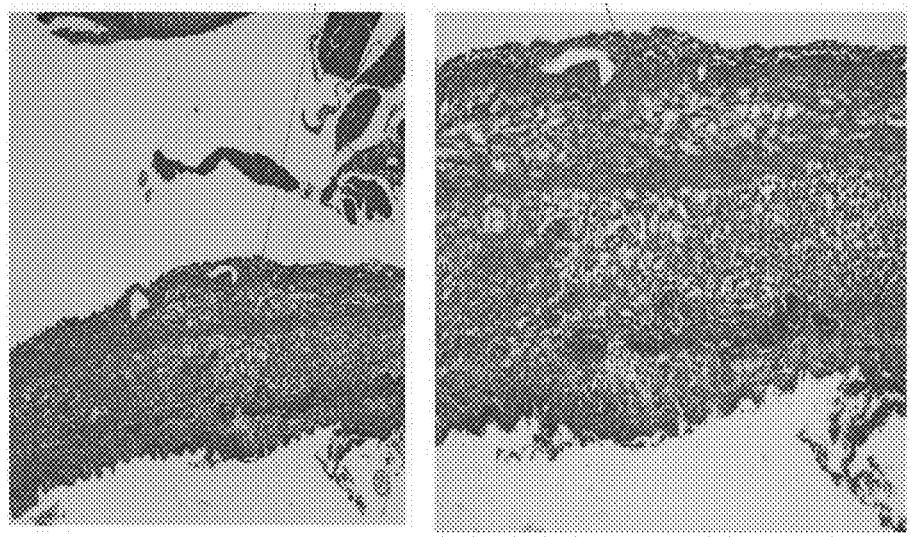
Figure 45B:
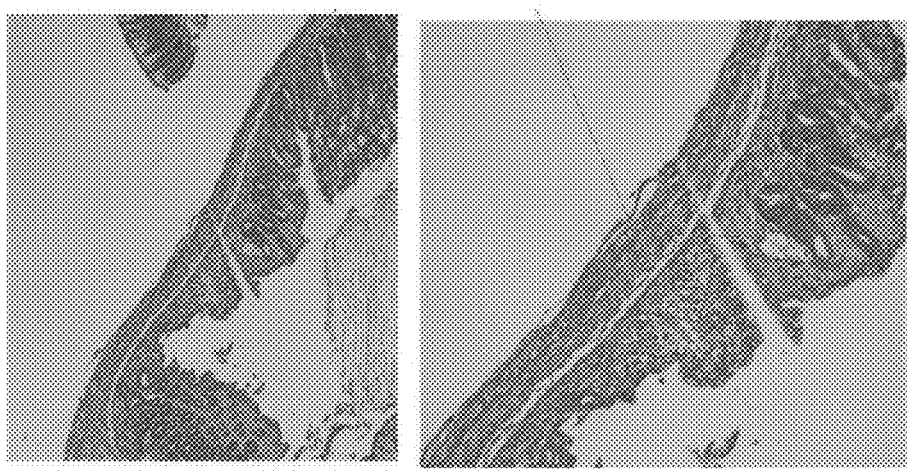
Figure 46:
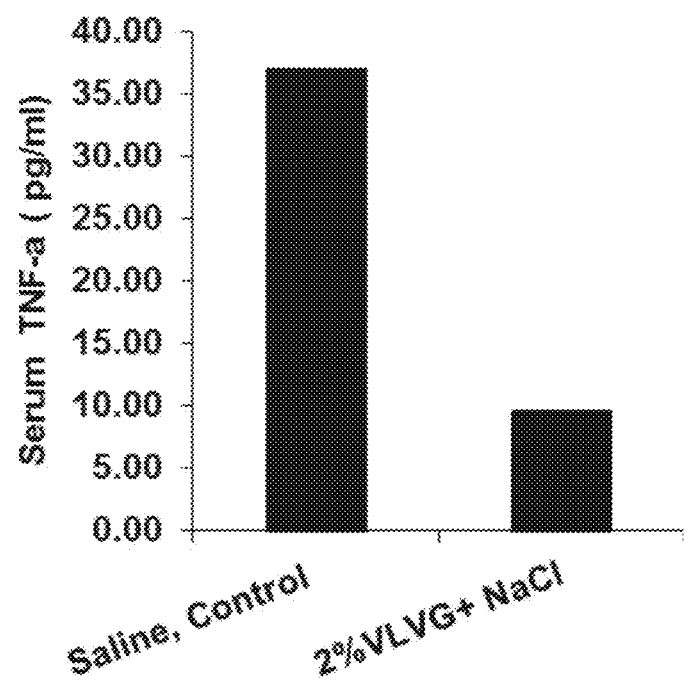

FIG. 12 is a bar graph showing serum albumin levels in mice 48 hours after administration of concanavalin A, following treatment with dexamethasone (Dex), 2% solutions of VLVG alginate or γ-irradiated LVG150 alginate (2% LVG (gamma radiation)) homogenized in saline, or with saline control (saline, cont) (*$p=0.000002$ relative to control);

FIG. 13 is a bar graph showing serum interleukin-6 levels in concanavalin A-challenged mice 14 hours after administration of concanavalin A, following treatment with dexamethasone (Dex), 2% solutions of VLVG alginate, LVG150 alginate or LVG54 alginate homogenized in saline, or with saline control (saline, cont) (*$p<0.00000001$ relative to control);

FIG. 14 is a bar graph showing serum interferon-γ (IFN-g) levels in concanavalin A-challenged mice 14 hours after administration of concanavalin A, following treatment with dexamethasone (Dex), 2% solutions of VLVG alginate, LVG150 alginate or LVG54 alginate homogenized in saline, or with saline control (saline, cont) (*$p<1.08 \cdot 10^{-8}$ relative to control, &$p<0.009$ relative to 2% VLVG);

FIG. 15 is a bar graph showing serum ALT activity in mice 14 hours after administration of concanavalin A, following treatment with dexamethasone (Dex), 2% solutions of VLVG alginate, LVG150 alginate or LVG54 alginate homogenized in saline, or with saline control (*$p<0.00001$, **$p<0.0000001$ relative to control, &$p<0.00000002$ relative to 2% VLVG);

FIG. 16 is a bar graph showing serum albumin levels in mice 14 hours after administration of concanavalin A, following treatment with dexamethasone (Dex), 2% solutions of VLVG alginate, LVG150 alginate or LVG54 alginate homogenized in saline, or with saline control (*$p<0.0000001$ relative to control, &$p<0.0006$ relative to 2% VLVG);

FIGS. 17A-17D present images (at ×100 magnification) of histological staining (hematoxylin & eosin) of liver from concanavalin A-challenged mice following treatment with dexamethasone (FIG. 17B), 2% solutions of VLVG alginate (FIG. 17D), or LVG54 alginate (FIG. 17C), or with saline (FIG. 17A) (scale bars represent 200 μm);

FIG. 18 presents images of immunohistochemical staining of biotin-labeled VLVG alginate in liver parenchyma (at magnifications of ×40 and ×100, scale bar represents 500 μm for magnification of ×40 and 200 μm for magnification of ×100);

FIGS. 19A and 19B present images showing presence of stained biotin in liver and pancreas (FIG. 19B) and absence of stained biotin in colon and spleen (FIG. 19A), following administration of a 2% solution of biotin-labeled VLVG alginate (no staining is visible after administration of saline as control, scale bars represent 200 μm);

FIG. 20 is a bar graph showing serum ALT activity in mice 6, 24 and 48 hours after administration of concanavalin A, following oral administration of dexamethasone (Dex), 2% solution of VLVG alginate homogenized in saline, or saline control (*$p=0.03$, $p<0.0002$, *$p<0.00005$ relative to control);

FIG. 21 is a bar graph showing serum albumin levels in mice 48 hours after administration of concanavalin A, following oral administration of dexamethasone (Dex), 2% solution of VLVG alginate homogenized in saline, or saline control (*p<0.0001, **p<2.62.10$^{-10}$ relative to control);

FIG. 22 is a bar graph showing serum interleukin-6 levels in mice 48 hours after administration of concanavalin A, following oral administration of dexamethasone (Dex), 2% solution of VLVG alginate homogenized in saline, or saline control (*p<3.3·10$^{-10}$ relative to control);

FIG. 23 is a bar graph showing serum ALT activity in mice 6, 24 and 48 hours after administration of concanavalin A, following oral administration of dexamethasone (Dex), 2% solutions of VLVG alginate, LVG54 alginate or LVG150 alginate homogenized in saline, or saline control (*p<0.05, p<0.005, *p<0.0002 relative to control);

FIG. 24 is a bar graph showing serum albumin levels in mice 48 hours after administration of concanavalin A, following oral administration of dexamethasone to (Dex), 2% solutions of VLVG alginate, LVG54 alginate or LVG150 alginate homogenized in saline, or saline control (*p<0.0001 relative to control);

FIG. 25 is a bar graph showing serum interleukin-6 levels in mice 48 hours after administration of concanavalin A, 2% solutions of VLVG alginate, LVG54 alginate or LVG150 alginate homogenized in saline, or saline control (*p<0.05 relative to control);

FIG. 26 is a bar graph showing serum ALT activity in mice 3 and 6 hours after partial hepatectomy, following treatment with a 2% solution of VLVG alginate homogenized in saline, or saline control (*p<0.0008, **p<0.02 relative to control);

FIG. 27 is a bar graph showing serum albumin levels in mice 6 hours after partial hepatectomy, following treatment with a 2% solution of VLVG alginate homogenized in saline, or saline control (*p<0.0001 relative to control);

FIG. 28 is a bar graph showing serum ALT activity in mice 6 and 24 hours after partial hepatectomy, following treatment with a 2% solution of VLVG alginate homogenized in saline, or saline control (*p<0.00002 relative to control);

FIG. 29 is a bar graph showing serum albumin levels in mice 24 hours after partial hepatectomy, following treatment with a 2% solution of VLVG alginate homogenized in saline, or saline control (*p<0.00003 relative to control);

FIG. 30 is a bar graph showing serum ALT activity in mice 24 and 48 hours after partial hepatectomy, following treatment with a 2% solution of VLVG alginate homogenized in saline, or saline control (*p<0.0001 relative to control);

FIG. 31 is a bar graph showing serum albumin levels in mice 48 hours after partial hepatectomy, following treatment with a 2% solution of VLVG alginate homogenized in saline, or saline control (*p<0.003 relative to control);

FIG. 32 is a bar graph showing serum ALT activity in mice 24 hours after administration of 4 mg paracetamol (APAP), with or without per os (PO) administration of 200 µl of a 2% solution of VLVG alginate homogenized in saline, 30 minutes prior to administration of paracetamol (p<0.0005 between the two groups);

FIGS. 33A and 33B present images (FIG. 33A; magnified ×40 and ×100) showing staining with IgG of necrotic cells in liver tissue from mice after administration of 4 mg paracetamol (APAP), with or without per os (PO) administration of a 2% solution of VLVG alginate homogenized in saline, 30 minutes prior to administration of paracetamol, as well as a bar graph (FIG. 33B) showing the amount of necrosis (scale to bars are 500 µm for ×40 magnification and 200 µm for ×100 magnification, *p<0.007);

FIG. 34 is a bar graph showing serum ALT activity in mice 24 hours after administration of 4 mg paracetamol (APAP), with or without per os (PO) administration of a 50, 100 or 200 µl of a 2% solution of VLVG alginate, 30 minutes prior to administration of paracetamol (*p<0.02, **p<0.000001 relative to APAP alone);

FIG. 35 presents images (magnified ×100) showing staining of nitrotyrosine in liver tissue from mice after administration of 4 mg paracetamol (APAP), with or without per os (PO) administration of 50 µl or 200 µl of a 2% solution of VLVG alginate, 30 minutes prior to administration of paracetamol;

FIG. 36 presents images (magnified ×100) showing staining of Ki-67 in liver tissue from mice after administration of 4 mg paracetamol (APAP), with or without per os (PO) administration of 50 µl or 200 µl of a 2% solution of VLVG alginate, 30 minutes prior to administration of paracetamol;

FIG. 37 is a bar graph showing serum paracetamol (APAP) levels in mice 1, 4 and 24 hours after administration of 4 mg paracetamol, with per os (PO) administration of a 100 µl or 200 µl of a 2% solution of VLVG alginate, 30 minutes prior to administration of paracetamol;

FIG. 38 is a bar graph showing serum ALT activity in mice 24 hours after administration of 4 mg paracetamol (APAP), with or without per os (PO) administration of 2% solutions of VLVG alginate, LVG54 alginate or LVG150 alginate homogenized in saline, or i.p. administration of a 2% solution of VLVG alginate, 30 minutes prior to administration of paracetamol (*p<0.05, p<0.01, *p<0.0002 relative to APAP alone; & p<0.04 relative to 2% VLVG i.p. treatment);

FIG. 39 is a bar graph showing serum ALT activity in mice 24 hours after administration of 8 mg paracetamol (APAP), with or without per os (PO) administration of a 2% solution of VLVG alginate homogenized in saline, 30 minutes prior to administration of paracetamol (*p=0.005 between the two groups);

FIG. 40 is a bar graph showing serum ALT activity in mice 24 hours after administration of vehicle or 8 mg paracetamol (APAP), with or without per os (PO) administration of a 2% solution of VLVG alginate homogenized in saline, 30 minutes prior to administration of paracetamol or vehicle (*p>0.004 relative to APAP alone);

FIG. 41 is a bar graph showing serum ALT activity in mice 24 hours after administration of 4 mg paracetamol (APAP), with or without per os (PO) administration of a 2% solution of VLVG alginate homogenized in saline, 30 or 60 minutes after administration of paracetamol (p<0.002 for difference between 30 and 60 minutes);

FIG. 42 is a bar graph showing serum ALT activity in mice 24 hours after administration of 4 mg paracetamol (APAP), with or without per os (PO) administration of a 2% solution of VLVG alginate homogenized in saline, 30 minutes after administration of paracetamol or concurrently (mix) with paracetamol (*p<0.01, **p<0.002 relative to APAP without VLVG);

FIG. 43 is a bar graph showing weight loss in mice subjected to TNBS (2,4,6-trinitrobenzenesulfonic acid)-induced colitis, following treatment with a 2% solution of VLVG alginate homogenized in saline or with saline;

FIG. 44 is a bar graph damage of the colon as determined by a histological activity index in mice subjected to TNBS-induced colitis, following treatment with a 2% solution of VLVG alginate homogenized in saline or with saline;

FIGS. 45A and 45B present images of colon tissue stained with hematoxylin & eosin (H&E) in mice subjected to TNBS-induced colitis, following treatment with a 2% solution of VLVG alginate homogenized in saline (FIG. 45B) or with saline (FIG. 45A);

FIG. 46 is a bar graph showing serum levels of TNF-α in mice subjected to TNBS-induced colitis, following treatment with a 2% solution of VLVG alginate homogenized in saline, or with saline.

DESCRIPTION OF SPECIFIC EMBODIMENTS OF THE INVENTION

The present invention, in some embodiments thereof, relates to biomaterials and, more particularly, but not exclusively, to novel alginate-based compositions, processes of preparing same and therapeutic uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While investigated the effects of alginate on liver damage, the present inventors to have sought methodologies for enhancing the ability of alginate to enter the body and be transported efficiently to a therapeutically relevant site within the body. While reducing the present invention to practice, the inventors have uncovered that homogenization of alginate in saline alters the physical properties of alginate considerably, in such a manner as to significantly enhance dissolution and diffusion of the alginate. The present inventors have further uncovered that compositions prepared by homogenization in saline exhibit considerable activity in protecting against liver damage, and that certain types of alginate and certain regiments are more effective than others at protecting against liver damage. The compositions further exhibit an ability to infiltrate into and localize within organs such as the liver following systemic administration. Thus, the composition does not need to be implanted in an organ (e.g., as an alginate scaffold), in contrast to previous methodologies, and a scaffold may be formed in vivo within a bodily organ or tissue or in situ, within a biological matrix.

Figure 1:
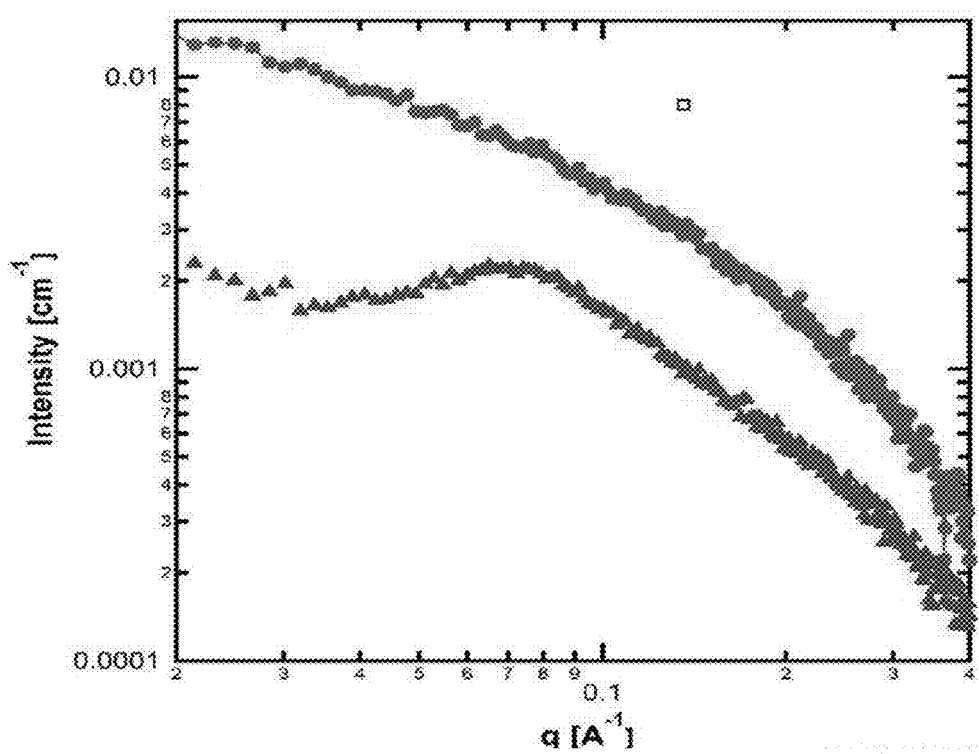
Figure 2:
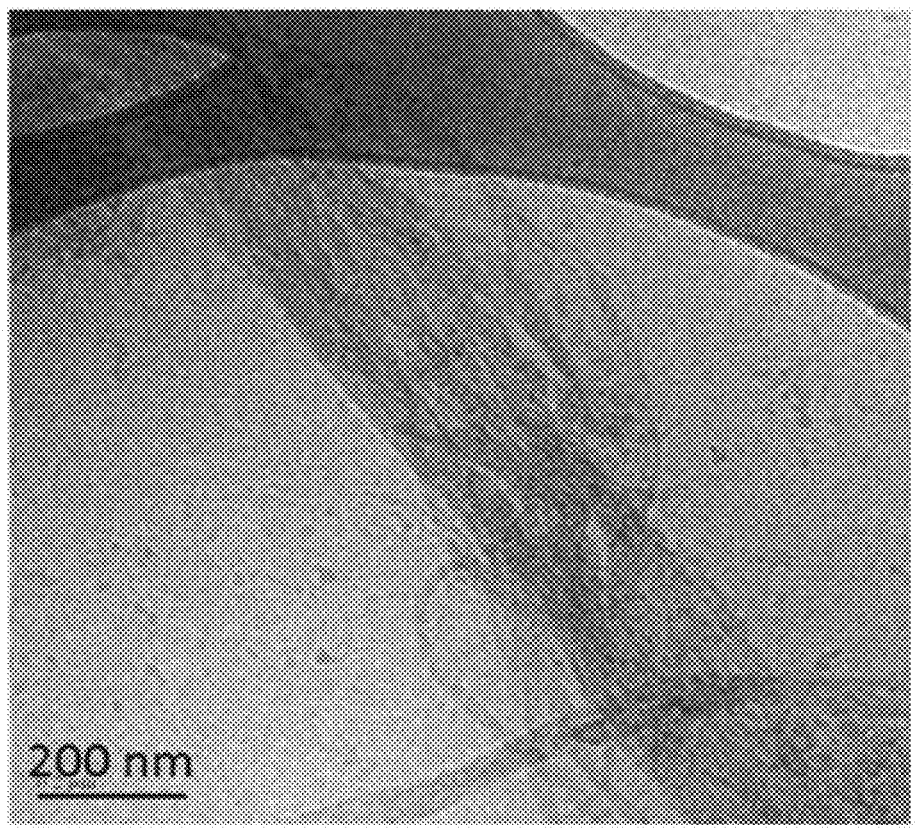

Referring now to the drawings and tables, FIG. 1 shows that an exemplary composition comprising alginate homogenized in saline exhibits a small angle X-ray scattering pattern markedly different from that of non-homogenized alginate in water. FIG. 2 shows multi-molecular structures which form from non-homogenized alginate in water, and which do not appear in exemplary compositions comprising alginate homogenized in saline. Table 2 shows that homogenization of alginate in saline results in considerably lower diameters, solution viscosities and zeta potentials, as well as in a very large (two orders of magnitude) increase in diffusion coefficients, as compare with non-homogenized alginate in water.

These results indicate that homogenization in saline results in alginate characterized by less intermolecular association between alginate molecules, a more globular and compact molecular shape, smaller size, and less negative surface charge, which together considerably enhance the dissolution and diffusion of the alginate molecules.

With respect to the biological activity of exemplary compositions comprising alginate homogenized in saline, FIGS. 3-4 and 15-17D and Table 3 show that a variety of exemplary alginate compositions reduce liver damage in a concanavalin A mouse model of liver damage, following intraperitoneal administration. FIGS. 5-6 and 13-14 show that alginate homogenized in saline can reduce levels of pro-inflammatory cytokines in a concanavalin a model. FIGS. 20-25 and Tables 7-8 show that alginate homogenized in saline also reduce liver damage and levels of pro-inflammatory cytokines in a concanavalin A mouse model when administered orally.

Figure 9:
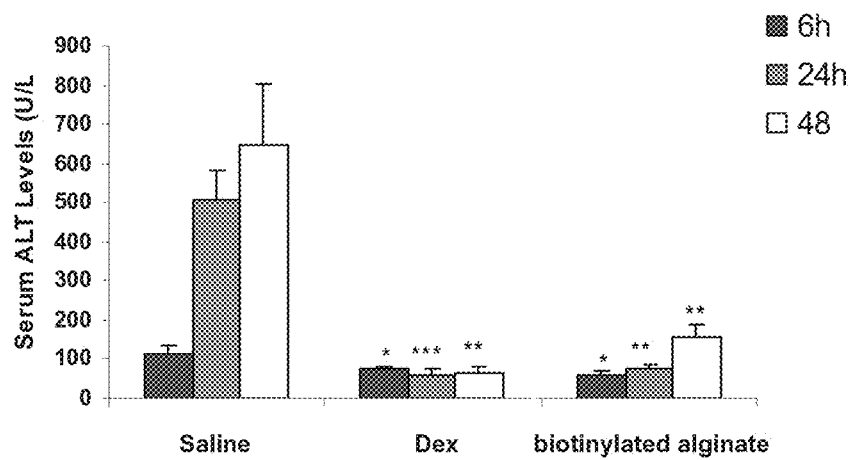
Figure 10:
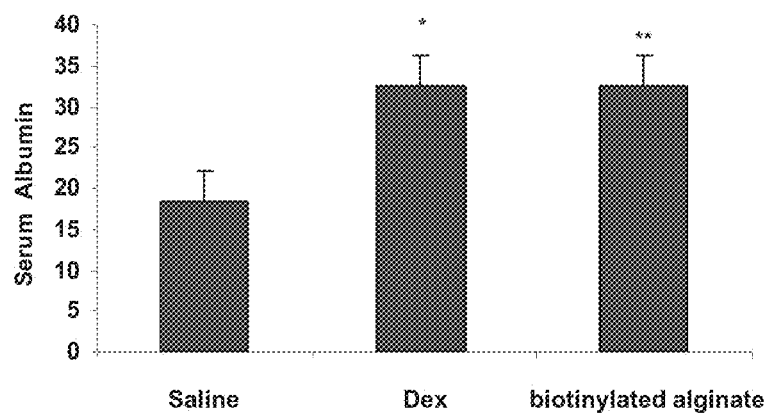

FIGS. 18-19B show that systemically administered biotin-labeled alginate localizes in the liver, further indicating that alginate can act on the liver following systemic administration. FIGS. 9-10 and Table 5 show that the biotin-labeled alginate exhibits the same protective effects as alginate.

These results indicate that systemically administered alginate homogenized in saline reduces liver damage and inflammation.

Figure 7:
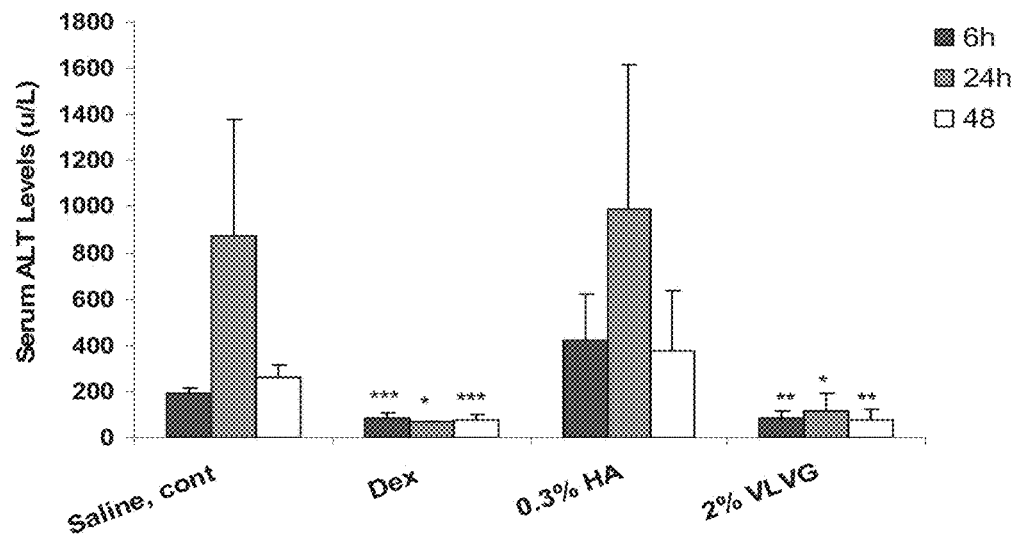
Figure 8:
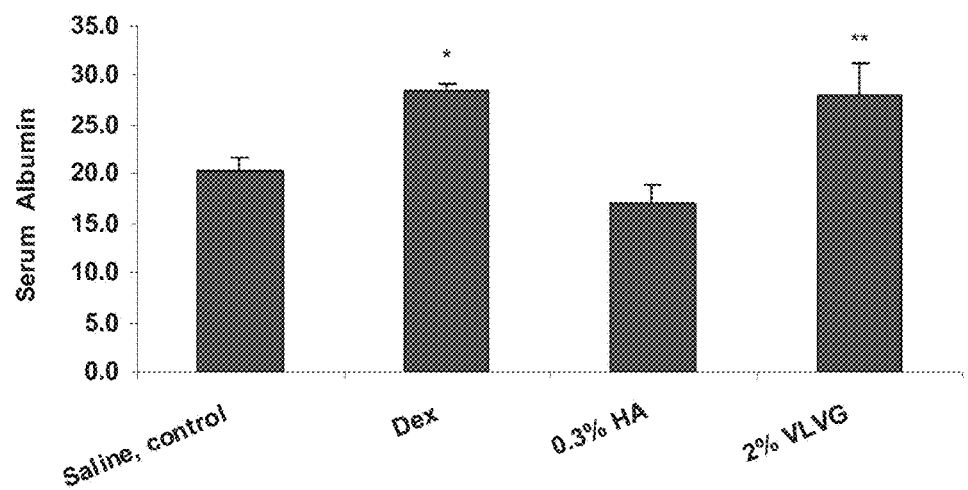
Figure 11:
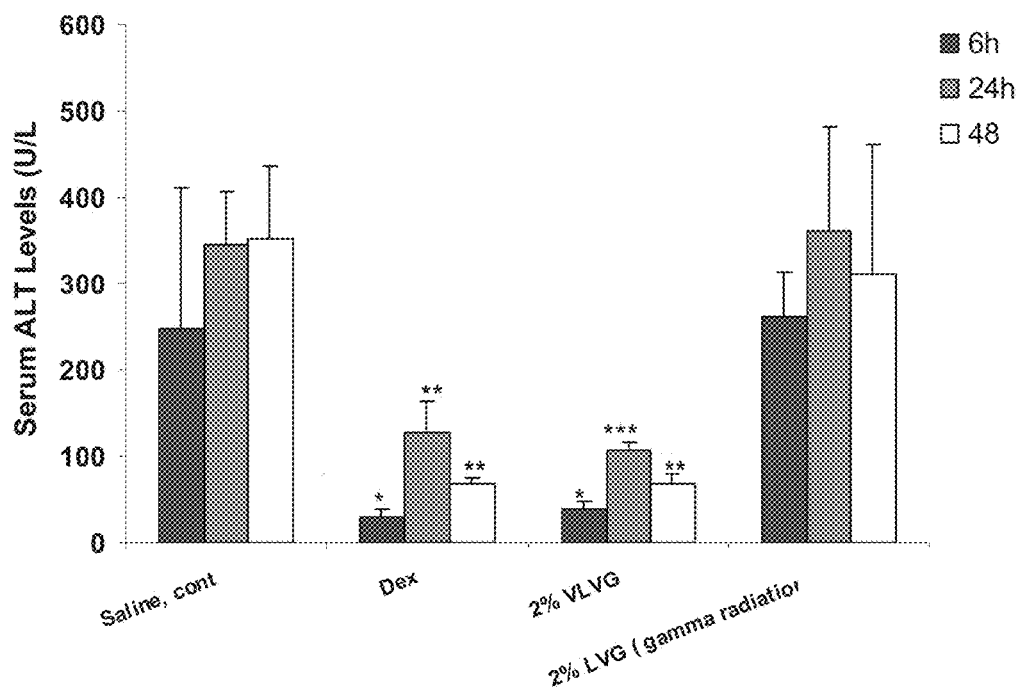

FIGS. 3-6, 14-17D and 23-25 and Tables 3 and 8 show that VLVG alginate, characterized by a molecular weight of 30-50 kDa, is more effective at reducing liver damage and levels of pro-inflammatory cytokines than are alginates characterized by a molecular weight of 100 kDa or more. FIGS. 11-12 and Table 6 show that the protective effect of exemplary alginate compositions is not exhibited by compositions comprising homogenized alginate with a molecular weight of approximately 3 kDa. FIGS. 7-8 and Table 4 show that the protective effect of exemplary alginate compositions is not exhibited by hyaluronan homogenized in saline.

These results indicate that the protective effects of alginate are associated with relatively low (but not too low) molecular weights, and are specific to alginate.

FIGS. 26-31 show that alginate homogenized in saline reduces liver damage in a partial hepatectomy mouse model. FIGS. 32-36 and 38-40 and Tables 9-12 show that alginate homogenized in saline reduces liver damage caused by paracetamol, when the alginate is administered prior to the paracetamol. FIGS. 34-36 show that a dose of 100 or 200 μl of a 2% solution of alginate in mice results in almost complete elimination of signs of hepatotoxicity caused by 4 mg paracetamol, whereas 50 μl is only partially effective. FIG. 37 shows that the reduction in liver damage is not due to any alteration of paracetamol absorption. FIG. 41 and Table 13 show that the alginate exhibits a superior protection against liver damage when administered 30 minutes after paracetamol (compared to alginate administered 60 minutes after paracetamol). FIG. 42 and Table 14 show that the alginate protects against liver damage when administered concomitantly with, or 30 minutes after paracetamol. FIG. 38 shows that VLVG alginate is more effective in a paracetamol intoxication model than are alginates characterized by higher solution viscosity, that oral administration and intraperitoneal administration of alginate are both effective, and that oral administration is particularly effective.

These results indicate that the alginate compositions described herein protect against liver damage caused by a broad variety of factors, including immune mediated reactions (as in a concanavalin A model), hepatectomy, and chemical hepatotoxicity (as in a paracetamol model). The results further show that for a variety of types of liver damage, protection can be obtained by systemic administration, including oral administration, and that the protective effects of the alginate are associated with relatively low molecular weights. The protection may be due to a local effect (e.g., a direct effect of alginate in contact with liver tissue) and/or due to a systemic effect, such as a systemic anti-inflammatory effect (e.g., by reducing levels of pro-inflammatory cytokines).

FIGS. 43-46 show that the alginate compositions also protects against colon damage in a model of inflammatory bowel disease (IBD).

Without being bound by any particular theory, it is believed that homogenization of alginate in saline and the relatively low molecular weights (as described hereinabove) of alginate both contribute to the therapeutic activity of alginate by reducing intermolecular associations and thereby enhancing dissolution, diffusion and in vivo transport of the alginate.

According to one aspect of embodiments of the invention, there is provided a composition (also referred to herein as an "alginate composition") comprising alginate, a source of sodium ions (e.g., sodium salt) and a carrier, as described herein. In some embodiments, the composition consists of alginate, a source of sodium ions (e.g., sodium salt) and a carrier.

Herein and in the art, the term "alginate" refers to a co-polymer comprising chains of (1-4)-linked β-D-mannuronic acid (M) and α-L-guluronic acid (G). The monomers can appear in homopolymeric blocks of consecutive G-residues (G-blocks), consecutive M-residues (M-blocks), or alternating M- and G-residues (MG-blocks).

The alginate may be characterized by any ratio of mannuronic acid residues (M) to guluronic acid residues (G).

In some embodiments, mannuronic acid represents at least 5% of the residues.

In some embodiments, mannuronic acid represents at least 10% of the residues. In some embodiments, mannuronic acid represents at least 20% of the residues. In some embodiments, mannuronic acid represents at least 30% of the residues. In some embodiments, mannuronic acid represents at least 45% of the residues. In some embodiments, mannuronic acid represents at least 50% of the residues. In some embodiments, mannuronic acid represents at least 60% of the residues. In some embodiments, mannuronic acid represents at least 70% of the residues. In some embodiments, mannuronic acid represents at least 80% of the residues. In some embodiments, mannuronic acid represents at least 90% of the residues. In some embodiments, mannuronic acid represents at least 95% of the residues.

In some embodiments, mannuronic acid represents from 25% to 65% of the residues, and guluronic acid represents from 35% to 75% of the residues.

In some of any of the embodiments described herein, the alginate is not silylated alginate.

In some embodiments, the alginate described herein is derived from brown algae. Suitable brown algae sources include, without limitation, *Laminaria hyperborea* and *Macrocystis pyrifera*.

Alternatively, the alginate may be chemically synthesized or derived from a biological source other than brown algae, such as from bacteria.

In some embodiments, the alginate in the composition is in a form of a sodium salt of alginate. In some embodiments, alginate in a form of a sodium salt is not considered to be a source of sodium ions, and an additional substance is present in the composition, serving as a source of sodium ions as described herein.

Herein, a "sodium salt" of alginate refers to alginate which comprises at least 0.2 sodium ions per carboxylate group (of the alginate) bound to the alginate (e.g., by ionic bonds). In some embodiments, the alginate comprises at least 0.3 sodium ions per carboxylate group. In some embodiments, the alginate comprises at least 0.4 sodium ions per carboxylate group. In some embodiments, the alginate comprises at least 0.5 sodium ions per carboxylate group. In some embodiments, the alginate comprises at least 0.6 sodium ions per carboxylate group. In some embodiments, the alginate comprises at least 0.7 sodium ions per carboxylate group. In some embodiments, the alginate comprises at least 0.8 sodium ions per carboxylate group. In some embodiments, the alginate comprises at least 0.9 sodium ions per carboxylate group. In some embodiments, the alginate comprises at least 0.95 sodium ions per carboxylate group. In some embodiments, the alginate comprises at least 0.99 sodium ions per carboxylate group.

According to some embodiments of the present invention, the composition comprises an alginate which is characterized by reduced association between the alginate chains.

Herein, "association" refers to a tendency for alginate chains to be in the proximity of one another, rather than being distributed relatively randomly. The tendency may be a result of attractive forces between the chains (e.g., electrostatic attraction) and/or steric factors (e.g., entanglement of chains), or as a result of cross-linking (which may be affected by, for example, di- or tri-valent ions). Similarly, "reduced association" refers herein to less proximity of chains to one another or reduced degree of cross-linking between the chains. Association between alginate chains affects various physical properties of the alginate in a composition, and is furthermore visible by transmission electron microscopy, as exemplified herein. Consequently, reduced association as described herein may be reflected by the properties described below.

In some embodiments, the alginate-containing composition is characterized by at least one of the following properties:

(i) A zeta potential weaker than −25 mV (i.e., closer to 0 mV), at a concentration of 0.5% (weight per volume) alginate in the abovementioned carrier;

(ii) A diffusion coefficient of at least $10^{-8}$ $cm^2$/second, at a concentration of 0.5% (weight per volume) alginate in the abovementioned carrier;

(iii) A molecular weight in a range of from 10 to 75 kDa;

(iv) A solution viscosity in a range of from 3 to 20 mPa*seconds, at a shear rate of 1 $second^{-1}$ and at a concentration of 2% weight/volume (20 grams per liter) in the carrier;

(v) A small angle X-ray scattering (SAXS) pattern characterized by an absence of a peak in scattering intensity in the interval $0.012<q<0.7 Å^{-1}$ and (vi) An absence of structures observable by transmission electron microscopy (e.g., cryogenic transmission electron microscopy) which are more than 5 nm in width.

Techniques for determining a diffusion coefficient, zeta potential, molecular weight, SAXS pattern, transmission electron microscopy image and/or a solution viscosity of alginate are exemplified herein. Additional techniques will be known by the skilled person. Values of diffusion coefficients, zeta potentials and solution viscosities herein refer to values at a temperature of 25° C.

In order to determine a presence or absence of structures by transmission electron microscopy, specimens are preferably vitrified (e.g., by rapid plunging into liquid ethane pre-cooled with liquid nitrogen) in a controlled-environment vitrification system, and examined using low-dose imaging, as exemplified herein, so as to prevent microstructural changes by ice crystallization and/or radiation damage. In addition, microscopy is preferably performed without heavy metal staining, so as to avoid structural changes due to interactions between alginate and heavy metal.

In some embodiments, the alginate in the composition is characterized by at least two of the aforementioned properties. In some embodiments, the alginate in the composition is characterized by at least 3 of the aforementioned properties. In some embodiments, the alginate in the composition is characterized by at least 4 of the aforementioned properties. In some embodiments, the alginate in the composition is characterized by at least 5 of the aforementioned properties. In some embodiments, the alginate in the composition is characterized by all of the aforementioned properties.

In some embodiments, the composition is characterized by a diffusion coefficient of at least $10^{-8}$ cm$^2$/second at a concentration of 0.5%, as described herein. In some embodiments, the diffusion coefficient is at least $2\times10^{-8}$ cm$^2$/second. in some embodiments, the diffusion coefficient is at least $3\times10^{-8}$ cm$^2$/second. In some embodiments, the diffusion coefficient is at least $4\times10^{-8}$ cm$^2$/second. In some embodiments, the diffusion coefficient is at least $5\times10^{-8}$ cm$^2$/second. In some embodiments, the diffusion coefficient is at least $6\times10^{-8}$ cm$^2$/second. In some embodiments, the diffusion coefficient is at least $7\times10^{-8}$ cm$^2$/second. In some embodiments, the diffusion coefficient is at least $8\times10^{-8}$ cm$^2$/second. In some embodiments, the diffusion coefficient is at least $9\times10^{-8}$ cm$^2$/second. In some embodiments, the diffusion coefficient is at least $10^{-7}$ cm$^2$/second. In some embodiments, the diffusion coefficient is at least $2\times10^{-7}$ cm$^2$/second. In some embodiments, the diffusion coefficient is at least $3\times10^{-7}$ cm$^2$/second.

It is to be understood that the phrase "at a concentration of 0.5%", recited herein with respect to diffusion coefficients and zeta potentials, does not indicate that the concentration of alginate in the composition described herein is necessarily 0.5%. Similarly, the phrase "at a concentration of 2%", recited herein with respect to solution viscosities, does not indicate that the concentration of alginate in the composition described herein is necessarily 2%. Rather, the phrases mean that a diffusion coefficient, zeta potential and solution viscosity are determined for a composition consisting of the alginate (at a concentration of 2% or 0.5%) and the carrier (and a source of sodium ions), that is, the composition for which diffusion coefficient, zeta potential or solution viscosity is determined may differ from the composition of embodiments of the invention in the amount of the carrier relative to the alginate. Thus, for example, a diffusion coefficient and/or zeta potential may be characterized by measuring a composition as described herein after the composition has been diluted with carrier (with a source of sodium ions) to result in an alginate concentration of 0.5%, as exemplified herein.

Diffusion coefficients may be determined using dynamic light scattering measurement, by recording the real time fluctuations in the intensity of the scattered light. Equations for calculating a diffusion coefficient based on measurement of the intensity time correlation function as a function of the decay time, are described in the Examples section herein.

In some embodiments, the alginate composition is characterized by at least one of a zeta potential described herein and a diffusion coefficient described herein.

In some embodiments, the alginate composition is characterized by a zeta potential described herein.

In some embodiments, the composition is characterized by both a diffusion coefficient as described herein, and a zeta potential as described herein.

Herein and in the art, the phrase "zeta potential" refers to electric potential difference between a dispersion medium (e.g., a liquid medium of the composition described herein) and a stationary layer of fluid attached to a dispersed particle (e.g., alginate). As alginate is negatively charged (due to the presence of carboxylate groups), the zeta potential of alginate in the carrier is negative. Thus, a "weaker" zeta potential refers to a value closer to 0 mV (i.e., less negative).

In some embodiments, the zeta potential is weaker than $-23$ mV, under the abovementioned measurement conditions. In some embodiments, the zeta potential is weaker than $-21$ mV. In some embodiments, the zeta potential is weaker than $-20$ mV. In some embodiments, the zeta potential is weaker than $-19$ mV.

Without being bound by any particular theory, it is believed that a weak zeta potential (e.g., weaker than $-25$ mV) indicates a high degree of masking by sodium ions of the negative charge of alginate carboxylate groups, which in turn weakens intermolecular forces between alginate molecules.

In some embodiments, the zeta potential is at least $-10$ mV (i.e., $-10$ mV or a more negative value). In some embodiments, the zeta potential is at least $-12.5$ mV. In some embodiments, the zeta potential is at least $-15$ mV.

In exemplary embodiments, the zeta potential is in a range of from about $-17.8$ mV to about $-21.2$ mV. In some embodiments, the zeta potential is about $-17.8$ mV.

Without being bound by any particular theory, it is believed that a very weak zeta potential (e.g., weaker than $-10$ mV) indicates a high degree of instability, as there is little electrostatic forces to repel alginate molecules from one another.

Zeta potentials may be determined by analyzing experimentally measured electrophoretic mobility distributions using a standard theoretical model. Devices for performing the measurements and analysis include, for example, a Zeta Plus™ zeta potential analyzer (Brookhaven Instruments Corp., NY).

As exemplified herein, alginates characterized by a molecular weight in a range of from 10 to 75 kDa exhibit stronger protective effects than do alginates characterized to by higher or lower molecular weights. In some embodiments, the alginate in the composition is characterized by a molecular weight in a range of from 20 to 60 kDa. In some embodiments, the alginate is characterized by a molecular weight in a range of from 30 to 50 kDa.

Molecular weight may be characterized by any of a variety of techniques known in the art for determining molecular weights of polymers. An exemplary technique is gel permeation chromatography-multiangle laser light scattering (GPC-MALLS), as exemplified herein. This technique provides the retention time of polymer samples, which can be converted to molecular weights using polymeric standards with known molecular weights.

In some embodiments, the composition comprising alginate as described herein is characterized by a solution viscosity in a range of from 5 to 20 mPa*seconds, under the measurement conditions described herein. In some embodiment, the solution viscosity is in a range of from 10 to 20 mPa*seconds. In exemplary embodiments, the solution viscosity is about 15.5 mPa*seconds.

Solution viscosity can be determined using commercially available stress-control rheometers (e.g., AR 2000 stress-control rheometer, TA Instruments). In exemplary embodiments, the rheometer is operated in the coneplate mode with a cone angle of 1° and a 60 mm diameter, as exemplified herein.

The solution viscosities described herein are relatively low for alginate solutions, and thus indicate alginate with a relatively low degree of intermolecular associations.

In some embodiments, the alginate is characterized by at least one of a molecular weight described herein and a solution viscosity described herein.

In some embodiments, the alginate is characterized by both a molecular weight described herein and by a solution viscosity described herein.

For many polymers such as alginate, solution viscosity is correlated strongly with molecular weight. As shown in the Examples herein, exemplary compositions according to embodiments of the invention exhibit unusually low solution viscosities as compared to other compositions comprising an alginate of the same molecular weight.

Hence, in some embodiments, the composition is characterized by a solution to viscosity which is low for the molecular weight of the alginate in the composition.

Thus, in some embodiments, the molecular weight is at least 30 kDa (e.g., from 30 to 50 kDa) and the solution viscosity is no more than 20 mPa*seconds (under the measurement conditions described herein). In some embodiments, the solution viscosity is in a range of from 10 to 20 mPa*seconds.

In some embodiments, the molecular weight is at least 100 kDa and the solution viscosity is no more than 270 mPa*seconds (under the measurement conditions described herein.

In some embodiments, the molecular weight is at least 155 kDa and the solution viscosity is no more than 890 mPa*seconds (under the measurement conditions described herein).

The phrase "absence of a peak in scattering intensity in the interval $0.012 < q < 0.7$ Å$^{-1}$" means that for the aforementioned range of values for the variable q, where q is defined as:

$$q = \frac{4\pi}{\lambda} \sin\theta$$

where $2\theta$ is the scattering angle, and $\lambda$ is the radiation wavelength (e.g., about 1.542 Å), there is no value of q for which the scattering intensity obtained by small angle X-ray scattering is greater than for slightly lower and higher values of q. Typically, in such a situation, the scattering intensity is simply correlated to the values of q, such that the highest scattering intensities are obtained for the highest values of q measured, as exemplified herein.

Small angle X-ray scattering measurements (e.g., utilizing Cu K$\alpha$ radiation) may be performed at ambient temperature (e.g., 25° C.) using commercially available devices (e.g., SAXSLAB GANESHA 300-XL system). The 2D SAXS images are azimuthally averaged to produce one-dimensional profiles of intensity, I vs. q, using commercially available data analysis programs, as exemplified herein. The scattering spectra of the capillary and control composition (i.e., composition lacking alginate) are collected and subtracted from the corresponding composition data, to produce the above-described scattering intensity as a function of q.

In some embodiments, the alginate composition is characterized by a diffusion coefficient described herein and by a molecular weight described herein.

In some embodiments, the alginate composition is characterized by a zeta potential described herein and by a molecular weight described herein.

In some embodiments, the composition is characterized by a diffusion coefficient as described herein, a zeta potential as described herein, and by a molecular weight described herein.

In some embodiments, the alginate composition is characterized by a diffusion coefficient described herein and by a solution viscosity described herein.

In some embodiments, the alginate composition is characterized by a zeta potential described herein and by a solution viscosity described herein.

In some embodiments, the composition is characterized by a diffusion coefficient as described herein, a zeta potential as described herein, and by a solution viscosity described herein.

In some embodiments, the alginate composition is characterized by a diffusion coefficient described herein and by a solution viscosity and molecular weight described herein.

In some embodiments, the alginate composition is characterized by a zeta potential described herein and by a solution viscosity and molecular weight described herein.

In some embodiments, the composition is characterized by a diffusion coefficient as described herein, a zeta potential as described herein, and by a solution viscosity and molecular weight described herein.

In some embodiments, the alginate composition is characterized by a diffusion coefficient described herein and by a scattering pattern described herein.

In some embodiments, the alginate composition is characterized by a zeta potential described herein and by a scattering pattern described herein.

In some embodiments, the composition is characterized by a diffusion coefficient as described herein, a zeta potential as described herein, and by a scattering pattern described herein.

In some embodiments, the alginate composition is characterized by a diffusion coefficient described herein and by an absence of observable structures more than 5 nm to in width, as described herein.

In some embodiments, the alginate composition is characterized by a zeta potential described herein and by an absence of observable structures more than 5 nm in width, as described herein.

In some embodiments, the composition is characterized by a diffusion coefficient as described herein, a zeta potential as described herein, and by an absence of observable structures more than 5 nm in width, as described herein.

The carrier of the composition is a liquid carrier. The carrier may be a pure substance (e.g., a solvent) or may comprise additional ingredients (e.g., a solution consisting of a solvent and solutes). In exemplary embodiments, the carrier is an aqueous carrier, such that the composition comprises an aqueous solution of the alginate and the source of sodium ions. The aqueous carrier may be, for example, water, having the alginate and source of sodium ions dissolved therein, or an aqueous solution.

The source of sodium ions can be a sodium salt. Preferably, the sodium salt is a pharmaceutically acceptable salt.

Sodium chloride is an exemplary source of sodium ions.

In some embodiments, the carrier is a pharmaceutically acceptable carrier.

Herein, the term "pharmaceutically acceptable carrier" refers to a carrier or a diluent that does not cause significant irritation to an organism and does not abrogate the biological activity and properties of the administered compound. Examples, without limitations, of pharmaceutically acceptable carriers are: propylene glycol, saline, emulsions and mixtures of organic solvents with water.

In some embodiments, the presence of sodium ions in the composition (e.g., from the sodium salt) helps to maintain the alginate in the composition in the form of a sodium salt.

In some embodiments, the composition contains sodium ions in a range of from 0.03 to 0.75 M. In some embodiments, the concentration is in a range of from 0.05 to 0.45 M. In some embodiments, the concentration is in a range of from 0.075 to 0.3 M. In some embodiments, the concentration is in a range of from 0.1 to 0.2 M. In exemplary embodiments, the concentration is about 0.15 M.

In some embodiments, the composition comprises alginate in the carrier at a concentration in a range of from 0.4% to 10% (w/v). In some embodiments, the concentration is in a range of from 1% to 4% (w/v). In exemplary embodiments, the concentration is about 2% (w/v).

According to another aspect of embodiments of the invention, there is provided a process for preparing a composition comprising alginate (e.g., the alginate composition described herein). The process comprises contacting an alginate (e.g., an alginate described herein) and a carrier (as described herein) which comprises a source of sodium ions, to thereby obtain a solution of the alginate and sodium ions in the carrier, and homogenizing the obtained solution.

In some embodiments, the carrier is a pharmaceutically acceptable carrier (as described herein), such that the alginate composition obtained by the process is a pharmaceutical composition.

As used herein, the terms "homogenize", "homogenization" and variants thereof refer to vigorous mixing. Various commercially available apparatuses, referred to in the art as "homogenizers" are suitable for performing such mixing. Such vigorous mixing is used in the art to form homogeneous suspensions or emulsions from different insoluble phases. The terms as used herein should not be construed as meaning that a suspension or emulsion is necessarily formed from different insoluble phases. However, it is to be appreciated that the disruption of multi-molecular structures by vigorous mixing, as exemplified herein, does suggest that a more homogeneous substance is formed thereby.

In some embodiments, the vigorous mixing is characterized by a mixing frequency (e.g., a frequency at which the mixture is stirred and/or vibrated) of at least 10,000 cycles per minute. In some embodiments, the frequency is at least 15,000 per minute. In some embodiments, the frequency is at least 20,000 per minute. In some embodiments, the frequency is at least 25,000 per minute. In exemplary embodiments, the frequency is at about 28,000 per minute.

Homogenization may be performed for any amount of time sufficient to dissolve the alginate in the carrier and result in characteristics of a composition described herein, for example, a diffusion coefficient, solution viscosity, zeta potential, scattering peak, and/or absence of multi-molecular structures, as described herein.

In some embodiments, homogenization is performed for at least 20 seconds. In some embodiments, homogenization is performed for at least 40 seconds. In some embodiments, homogenization is performed for at least 60 seconds. In some embodiments, homogenization is performed for at least 90 seconds. In some embodiments, homogenization is performed for at least two minutes. In exemplary embodiments, homogenization is performed for at least three minutes.

As exemplified herein, the process described herein alters various physical characteristics of the alginate in the carrier, in a manner which is believed to be advantageous. However, the process described herein is not expected to alter the molecular weight or starting concentration of alginate.

Hence, in some embodiments, the molecular weight of the alginate contacted with the carrier is a molecular weight as described herein (e.g., from 10 to 75 kDa). However, alginates characterized by lower or higher MW are also contemplated within embodiments of this aspect of the present invention. In some embodiments, the alginate homogenized with the carrier is at a concentration as described herein (e.g., from 0.4% to 10% (w/v). Lower or higher concentrations are also contemplated.

It is to be understood that all compositions formed by the process described herein are within the scope of embodiments of the invention.

In some embodiments, the process is for preparing a composition characterized by properties as described herein.

As shown in the Examples Section that follows, compositions such as described herein are highly effective at protecting against liver damage in a variety of animal models.

Hence, according some embodiments, the composition is for use in protecting a subject from liver damage.

Herein, the phrase "protecting a subject from liver damage" refers to treating damage that has already been caused by reducing or eliminating the damage, and/or to preventing or reducing future liver damage (namely, protecting the liver from damage).

As used herein, the terms "treat", "treating" and "treatment" encompass abrogating, substantially inhibiting, slowing or reversing the progression of a condition, substantially ameliorating clinical or aesthetical symptoms of a condition or substantially preventing or reduce the appearance of clinical or aesthetical symptoms of a condition.

A method, use or treatment according to any aspect of embodiments of the invention described herein may be used in association with an alginate composition according to any one of the embodiments described herein regarding an alginate composition, unless otherwise indicated.

According to another aspect of embodiments of the invention, there is provided a method of protecting a subject in need thereof from liver damage. The method comprises administering to the subject a therapeutically effective amount, as defined herein, of a composition described herein.

According to another aspect of embodiments of the invention, there is provided a use of a composition described herein in the manufacture of a medicament, for example, a medicament for protecting a subject from liver damage.

Herein, the "subject" encompasses any subject who is afflicted by a hepatic disease or disorder and/or is exposed or is about to be exposed to a hepatotoxic agent, as further detailed herein below. The subject may be already diagnosed as being previously exposed to the hepatotoxic agent and/or diagnosed with a hepatic disease or disorder; subjects having a medical condition which is to be treated with a hepatotoxic agent and/or has already begun treatment with a hepatotoxic agent; and any subject at risk for liver injury associated with a hepatotoxic agent (e.g., an alcoholic).

The subject may be any human or non-human animal. In some embodiments, the subject is a mammal. In exemplary embodiments, the subject is a human.

As used herein, the phrase "therapeutically effective amount" generally describes an amount of the compound or composition being administered which will relieve to some extent one or more of the symptoms of the condition being treated. The relief may be of an existing symptom and/or of a future symptom (e.g., a symptom of a condition which is to be prevented or reduced, or protected from).

In the context of protecting a subject from liver damage, a therapeutically effective amount is sufficient to result in a reduction in liver damage by at least 25%, and preferably at least 50%, as compared to liver damage in individuals who are in a similar condition but are not administered the alginate composition as described herein. Liver damage may be quantified according to serum levels of any biomolecule which is used in the art as a marker for liver damage (e.g., as exemplified herein), where liver to damage is represented by the difference between measured serum levels of the biomolecule and the normal range for serum levels of the biomolecule (as recognized in the art). For example, when liver damage is indicated by serum levels of alanine transaminase (ALT) above the upper limit of normal (ULN), a reduction by 50% of the difference between serum levels of ALT and the ULN (in comparison with individuals not administered alginate) indicates a reduction of 50% in liver damage. In addition, to ALT, aspartate transaminase (AST), albumin, and alkaline phosphatase (ALP) are examples of markers used in the art for determining liver damage.

In the context of using a hepatotoxic agent (e.g., a hepatotoxic drug) to treat a medical condition treatable by the hepatotoxic agent, as described herein, a therapeutically effective amount is an amount which will relieve to some extent one or more of the symptoms of the condition treatable by the hepatotoxic agent, and which is an amount sufficient to cause liver damage in at least some subjects.

In some of any one of the embodiments described herein, the method, composition and/or medicament described herein is for treating a hepatic disease or disorder.

In some of any one of the embodiments described herein, the hepatic disease or disorder is an acute disorder.

In some of any one of the embodiments described herein, the hepatic disease or disorder is a chronic disorder.

Examples of hepatic disease or disorders treatable according to embodiments of the invention include, without limitation, non-alcoholic steatohepatitis (NASH), non-alcoholic fatty liver disease (NAFLD), alcoholic liver disease, a hepatectomy-related disease or disorder, liver damage induced by a hepatotoxic agent, a viral hepatitis, an immune-mediated liver disease, a graft-versus-host disease (GVHD) of the liver (e.g., following a liver transplantation), a metabolic liver disease, a liver cancer (including primary and secondary liver cancer), and an acute hepatic failure.

Examples of viral hepatitis treatable according to embodiments of the invention include, without limitation, hepatitis A, hepatitis B, hepatitis C, hepatitis D and hepatitis E. These forms of hepatitis are associated with hepatitis A virus (HAV), hepatitis B virus (HBV), hepatitis C virus (HCV), hepatitis D virus (HDV) and hepatitis E virus (HEV), respectively.

Examples of immune-mediated liver disease treatable according to embodiments of the invention include, without limitation, autoimmune hepatitis, primary sclerosing cholangitis (PSC) and primary biliary cirrhosis (PBC).

Herein, the phrase "metabolic liver disease" refers to any disease caused by a disruption of a normal metabolic pathway because of a genetic defect (referred to in the art as a "metabolic disease") which manifests, at least in part, as a disease or disorder of the liver. Examples of metabolic liver disease treatable according to embodiments of the invention include, without limitation, Wilson's disease and hemochromatosis.

As used herein, the phrase "acute hepatic failure" (also referred to in the art as "acute liver failure") refers to a condition characterized by appearance of severe complications within 28 days of the first signs of liver damage (e.g., jaundice). In some embodiments, the appearance of severe complications is within 14 days of the first signs of liver damage. In some embodiments, acute liver failure is characterized by the appearance of severe complications within 7 days of the first signs of liver damage (such a condition is referred to by some in the art as "hyperacute"). In some embodiments, the appearance of severe complications is within 6 days of the first signs. In some embodiments, the appearance of severe complications is within 5 days of the first signs. In some embodiments, the appearance of severe complications is within 4 days of the first signs. In some embodiments, the appearance of severe complications is within 3 days of the first signs. In some embodiments, the appearance of severe complications is within 2 days of the first signs. In some embodiments, the appearance of severe complications is within 24 hours of the first signs of liver damage.

In some of any one of the embodiments described herein, the hepatic disease or disorder comprises liver damage induced by a hepatotoxic agent. In some embodiments, the liver damage induced by a hepatotoxic agent is a drug-induced liver injury (DILI), as this term is defined in the art, the hepatotoxic agent being a drug.

In some of any one of the embodiments described herein, the liver damage (e.g., DILI) is characterized by relatively predictable reactions, for example, hepatotoxicity is dose-related, has a high incidence, occurs with a short latency (within a few days), results from direct toxicity of the hepatotoxic agent (e.g., a hepatotoxic drug) or its metabolite and/or is reproducible in animal models. Paracetamol is an exemplary agent which induces DILI characterized by a predictable reaction.

In some of any one of the embodiments described herein, the liver damage (e.g., DILI) is characterized by idiosyncratic reactions, for example, occurs with variable latency (at least 1 week), has a low incidence, hepatotoxicity may not be dose-related, levels of ALT are more than 3 times the upper limit of normal (ULN) and/or alkaline phosphatase (ALP) levels are more than twice the ULN. Most hepatotoxic drugs are associated with DILI characterized by idiosyncratic reactions.

In some of any one of the embodiments described herein, the liver damage (e.g., DILI) is mediated by an immune reaction.

In some of any one of the embodiments described herein, the liver damage (e.g., DILI) is not mediated by an immune reaction.

In some of any one of the embodiments of the invention described herein, the liver damage induced by a hepatotoxic agent may comprise treatment of existing liver damage and/or reducing or preventing liver damage which would be or may be caused by a hepatotoxic agent.

In some of any one of the embodiments described herein, the method, composition and/or medicament described herein is for reducing or preventing a liver damage caused by a hepatotoxic agent.

In some of any one of the embodiments described herein, the method reduces by at least 25%, and preferably by at least 50%, the amount liver damage caused by the hepatotoxic agent subsequently to the time at which the alginate composition is administered. Liver damage caused by the hepatotoxic agent subsequently to administration of the alginate composition is determined according to changes in levels of a marker (e.g., as described herein) for liver damage after the time of alginate administration.

In some of any one of the embodiments described herein, the method, composition and/or medicament described herein is for treating a medical condition treatable by a hepatotoxic agent (e.g., a hepatotoxic drug). In such embodiments, the method comprises co-administering a therapeutically effective amount of the hepatotoxic agent (so as to treat the medical condition) and the composition described herein (so as to reduce or prevent liver damage by the hepatotoxic agent). The therapeutically effective amount of the hepatotoxic agent is sufficient to be capable of to causing liver damage, as described herein. The administered composition should comprise a therapeutically effective amount of the alginate in the composition.

The co-administration of a therapeutically effective amount of a hepatotoxic agent with an alginate composition is superior to current methodologies and regimens for administration of therapeutically effective amounts of hepatotoxic agents, in view of the hepatoprotection provided by the alginate. The co-administration described herein may therefore be effected without required monitoring of liver function, or with less frequent monitoring, in a subject being co-administered the hepatotoxic agent and alginate composition, in contrast to current methodologies.

In some of any one of the embodiments described herein, administration of the composition is performed in accordance with any of the methods and/or treatments described in co-filed International Patent Application, which claims priority from U.S. Provisional Patent Application No. 61/747,325, the contents of which are incorporated herein by reference in their entirety.

The hepatotoxic agent described herein throughout may be any therapeutically active agent known in the art of medicine which can cause liver damage (examples of which are described in detail below), as well as any other substance which is hepatotoxic when consumed. Examples of such substances include, without limitation, alcohol (e.g., ethanol) and beverages which contain alcohol (e.g., beer, wine, liquors), as well as chemicals found in industry and in household products (e.g., methanol, carbon tetrachloride, vinyl chloride and other volatiles, and arsenic).

Exposure to alcohol by self-administration (e.g., drinking alcoholic beverages) is very common, and is a leading cause of liver damage. In some embodiments, the alginate composition is included in an alcoholic beverage (e.g., beer, wine, liquor) or in any other alcoholic composition which may be drunk (e.g., rubbing alcohol), so as to prevent or reduce liver damage caused by the alcohol.

In some of any one of the embodiments described herein, the hepatotoxic agent is a therapeutically active agent (e.g., a conventional drug), namely, an agent administered in order to treat a medical condition. Examples of hepatotoxic drugs and medical conditions treatable by the drugs are presented, without limitation, in Table 1.

TABLE 1

| Hepatotoxic drug | Medical condition(s) treatable by drug |
|---|---|
| Paracetamol (acetaminophen, APAP) | Fever; pain |
| Acarbose | Diabetes |
| Amiodarone | Cardiac arrhythmia |
| Bosentan | Hypertension |
| Bromfenac | Inflammation; pain |
| Dantrolene | Malignant hyperthermia; neuroleptic malignant syndrome; muscle spasticity; Ecstasy intoxication; serotonin syndrome; 2,4-dinitrophenol poisoning |
| Diclofenac | Pain; inflammation; dysmenorrhea |
| Dihydralazine | Hypertension |
| Disulfiram | Alcohol dependence; cocaine dependence; scabies; protozoal infections |
| Felbamate | Epilepsy |
| Fluoxetine | Depression; obsessive-compulsive disorder; eating disorders; panic disorder; body dysmorphic disorder; premenstrual dysphoric disorder; trichotillomania; cataplexy; alcohol dependence |

TABLE 1-continued

| Hepatotoxic drug | Medical condition(s) treatable by drug |
|---|---|
| Halothane | Surgery |
| Isoniazid | Bacterial infections |
| Kava | Anxiety disorder |
| Ketoconazole | Fungal infections; alopecia |
| Labetalol | Hypertension |
| Leflunomide | Rheumatoid arthritis; psoriatic arthritis |
| Methotrexate | Cancer; rheumatoid arthritis; psoriasis; psoriatic arthritis; lupus; inflammatory bowel disease; pregnancy; ectopic pregnancy |
| Methyldopa | Hypertension; pre-eclampsia |
| Nefazodone | Depression; migraine |
| Nicotinic acid | Pellagra; atherosclerosis |
| Paroxetine | Depression; obsessive-compulsive disorder; post-traumatic stress disorder; panic disorder; anxiety disorder; premenstrual dysphoric disorder; premature ejaculation |
| Pemoline | Narcolepsy; attention-deficit hyperactivity disorder |
| Propylthiouracil | Hyperthyroidism |
| Pyrazinamide | Bacterial infections |
| Rifampin | Bacterial infections; cholestatic pruritis; vaccinia virus infection |
| Ritonavir | Retroviral infections |
| Sertraline | Depression; obsessive-compulsive disorder; post-traumatic stress disorder; panic disorder; body dysmorphic disorder; anxiety disorder; eating disorders; premenstrual dysphoric disorder; syncope |
| Statins | Cardiovascular disease |
| Tacrine | Alzheimer's disease |
| Tetracycline antibiotics | Bacterial infections; malaria; balantidiasis |
| Tolcapone | Parkinson's disease |
| Troglitazone | Diabetes |
| Trovafloxacin | Bacterial infections |
| Valproic acid | Epilepsy; bipolar disorder; depression; migraine; schizophrenia; colorectal polyps; basal cell carcinoma; acne; Alzheimer's disease |
| Ximelagatran | Deep venous thrombosis; venous thromboembolism; atrial fibrillation |
| Zafirlukast | Asthma |
| Zileuton | Asthma |
| Anabolic steroids | Hypoplastic anemia; growth failure; cancer; AIDS; delayed puberty; bone loss; gender identity disorder |
| Azathioprine | Graft-versus-host reaction; rheumatoid arthritis; pemphigus; lupus; Behcet's disease; autoimmune hepatitis; atopic dermatitis; myasthenia gravis; neuromyelitis optica; restrictive lung disease; inflammatory bowel disease; multiple sclerosis |
| Azithromycin | Bacterial infections; toxoplasmosis; malaria |
| Captopril | Hypertension; congestive heart failure; diabetic nephropathy |
| Cimetidine | Heartburn; peptic ulcer; herpes zoster; calcific tendinitis; interstitial cystitis; cancer |
| Ciprofloxacin | Bacterial infections |
| Clopidogrel | Atherosclerosis; coronary artery disease; peripheral vascular disease; cerebrovascular disease; coronary stent implantation |
| Dicloxacillin | Bacterial infections |
| Erythromycin | Bacterial infections |
| Estrogens | Pregnancy |
| Flucloxacillin | Bacterial infections |
| Naproxen | Fever; pain; inflammation; dysmenorrhea |
| Phenobarbital | Epilepsy; benzodiazepine dependence; Gilbert's syndrome; cyclic vomiting syndrome |
| Phenothiazine antipsychotics | Schizophrenia; acute psychosis; bipolar disorder; hallucination; delusion |

TABLE 1-continued

| Hepatotoxic drug | Medical condition(s) treatable by drug |
|---|---|
| | disorder; congestive heart failure; porphyria; tetanus; amoebic meningoencephalitis; insomnia; pruritus; migraine; opioid addiction |
| Phenytoin | Epilepsy |
| Sulindac | Pain; inflammation; colorectal polyps; preterm labor; Alzheimer's disease |
| Terbinafine | Fungal infections |
| Tricyclic antidepressants | Depression; anxiety disorder; obsessive-compulsive disorder; panic disorder; post-traumatic stress disorder; body dysmorphic disorder; personality disorder; attention-deficit hyperactivity disorder; eating disorders; bipolar disorder; pain; neuralgia; fibromyalgia; migraine; smoking addiction; Tourette syndrome; trichotillomania; irritable bowel syndrome; interstitial cystitis; nocturnal enuresis; narcolepsy; insomnia; pathological crying and/or laughing; chronic hiccups; ciguatera poisoning; schizophrenia; biliary dyskinesia |
| Amoxicillin-clavulanic acid | Bacterial infections |
| Carbamazepine | Epilepsy; bipolar disorder; neuropathic pain; attention-deficit hyperactivity disorder; schizophrenia; phantom limb syndrome; complex regional pain syndrome; paroxysmal extreme pain disorder; neuromyotonia; intermittent explosive disorder; personality disorder; myotonia congenita; post-traumatic stress disorder |
| Cyclosporine | Graft-versus-host reaction; psoriasis; atopic dermatitis; pyoderma gangrenosum; autoimmune urticaria; rheumatoid arthritis; dry eye |
| Enalapril | Hypertension; chronic heart failure |
| Flutamide | Prostate cancer |
| Methimazole | Hyperthyroidism |
| Nitrofurantoin | Bacterial infections |
| Sulfonamides | Bacterial infections; retroviral infections; diabetes; heart failure; liver cirrhosis; hypertension; glaucoma; epilepsy; altitude sickness; cystinuria; dural ectasia; periodic paralysis; osteoarthritis; rheumatoid arthritis; pain; colorectal polyps; burns; gout; hyperuricemia; cardiac arrhythmia; inflammatory bowel disease; migraine |
| Trazodone | Depression; bipolar disorder; anxiety disorder; insomnia; fibromyalgia; panic disorder; diabetic neuropathy; eating disorders; obsessive-compulsive disorder; alcohol dependence; schizophrenia; complex regional pain syndrome |
| Trimethoprim | Bacterial infections |
| Verapamil | Hypertension; angina pectoris; cardiac arrhythmia; cluster headache; migraine; malaria |
| Allopurinol | Hyperuricemia; gout; tumor lysis syndrome; ischemic reperfusion injury; uric acid nephrolithiasis; protozoal infections; epilepsy; hypertension |
| Aspirin | Pain; migraine; fever; cardiovascular disease; percutaneous coronary intervention; cancer; rheumatic fever; Kawasaki disease |
| Betahistine | Meniere's disease; balance disorder |
| Busulfan | Cancer |
| Cephalosporins | Bacterial infections |
| Chlorpheniramine | Allergy |
| Clarithromycin | Bacterial infections |
| Codeine | Pain; cough; diarrhea; irritable bowel syndrome |
| Corticosteroids | Adrenal insufficiency; congenital adrenal hyperplasia; pain; inflammation; arthritis; temporal arteritis; dermatitis; allergy; |

TABLE 1-continued

| Hepatotoxic drug | Medical condition(s) treatable by drug |
|---|---|
| | asthma; hepatitis; lupus; inflammatory bowel disease; sarcoidosis; Addison's disease; brain tumor |
| Cyclophosphamide | Cancer; lupus; rheumatoid arthritis; Wegener's granulomatosis; multiple sclerosis |
| Cytarabine | Cancer; herpesvirus infection |
| Danazol | Endometriosis; menorrhagia; fibrocystic breast disease; immune thrombocytopenic purpura; mastodynia; hereditary angioedema |
| Dihydrocodeine | Pain; cough; dyspnea; irritable bowel syndrome; opioid addiction |
| Fluconazole | Fungal infections |
| Hydralazine | Hypertension |
| Indinavir | Retroviral infections |
| Ma-huang | Excess weight |
| Mebeverine | Irritable bowel syndrome |
| Metoclopramide | Nausea; vomiting; gastroparesis; migraine |
| Oxycodone | Pain; diarrhea; irritable bowel syndrome |
| Penicillamine | Rheumatoid arthritis; Wilson's disease; cystinuria; scleroderma; arsenic poisoning |
| Phenylbutazone | Fever; pain |
| Procainamide | Cardiac arrhythmia |
| Quinidine | Cardiac arrhythmia; malaria |
| Retinol | Acne; acute promyelocytic leukemia; vitamin A deficiency |
| Reverse transcriptase inhibitors | Retroviral infections |
| Sulpiride | Schizophrenia; depression |
| Tamoxifen | Cancer; McCune-Albright syndrome; anovulatory disorder; retroperitoneal fibrosis; gynecomastia; bipolar disorder; Riedel's thyroiditis |
| Telithromycin | Bacterial infections |

Thus, in some of any one of the embodiments described herein, the method is for treating a medical condition selected from the group consisting of the medical conditions listed in Table 1 (right column), the method comprising co-administering to the subject a therapeutically effective amount of a hepatotoxic agent selected from the group consisting of the hepatotoxic drugs listed in Table 1 (left column) and a therapeutically effective amount of an alginate composition, the hepatotoxic drug being respective to the condition treatable by the drug (as listed in Table 1).

Examples of hepatotoxic anabolic steroids include, without limitation, 4-androstenedione, androstenone, boldenone, fluoxymesterone, methandienone, methandrostenolone, methyltestosterone, nandrolone decanoate, nortestosterone, oxandrolone, oxymetholone, testosterone and trenbolone.

Examples of hepatotoxic cephalosporins include, without limitation, cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxome, cefoperazone, ceftazidime, cefclidine, cefepime, cefluprenam, cefoselis, cefozopran, cefpirome, cefquinome, ceftobiprole and ceftaroline.

Examples of hepatotoxic corticosteroids include, without limitation, aclometasone dipropionate, amcinonide, betamethasone, betamethasone dipropionate, betamethasone sodium phosphate, betamethasone valerate, budesonide, clobetasone-17-butyrate, clobetasol-17-propionate, cortisone acetate, desonide, dexamethasone, dexamethasone sodium phosphate, fludrocortisone, fluocinonide, fluocinonide acetonide, fluocortolone, fluocortolone caproate, fluocortolone pivalate, fluprednidene acetate, halcinonide, hydrocortisone, hydrocortisone-17-aceponate, hydrocortisone acetate, hydrocortisone-17-buteprate, hydrocortisone-17-butyrate, hydrocortisone-17-valerate, methylprednisolone, mometasone, prednicarbate, prednisolone, prednisone, tixocortol pivalate, triamcinolone acetonide, and triamcinolone alcohol.

Examples of hepatotoxic estrogens include, without limitation, oral contraceptive ingredients such as ethinyl estradiol, estradiol valerate and mestranol. The estrogen may be formulated alone or in a form of a combined oral contraceptive, as is common in the art.

Examples of hepatotoxic phenothiazine antipsychotics include, without limitation, promethazine, chlorpromazine, promazine, triflupromazine, methotrimeprazine, mesoridazine, thioridazine, fluphenazine, perphenazine, prochlorperazine and trifluoperazine. In some embodiments, the phenothiazine antipsychotic is chlorpromazine. Conditions treatable by chlorpromazine include, without limitation, schizophrenia; acute psychosis; bipolar disorder; *porphyria*; tetanus; amoebic meningoencephalitis; insomnia; pruritus; migraine; and opioid addiction.

Examples of hepatotoxic reverse transcriptase inhibitors include, without limitation, nevirapine and nucleoside analog reverse transcriptase inhibitors (NRTIs) to such as abacavir, apricitabine, didanosine, emtricitabine, entecavir, lamivudine, nevirapine, stavudine, zalcitabine and zidovudine.

Examples of hepatotoxic statins include, without limitation, atorvastatin, cerivastatin, fluvastatin, lovastatin, mevastatin, pitavastatin, rosuvastatin and simvastatin.

Examples of hepatotoxic sulfonamides include, without limitation, anti-bacterial drugs such as sulfamethoxazole, sulfisomidine, sulfacetamide, sulfadoxine and dichlorphenamide; anti-diabetic agents such as carbutamide, acetohexamide, chlorpropamide, tolbutamide, tolazamide, glipizide, gliclazide, glibenclamide, glibornuride, gliquidone, glisoxepide, glyclopyramide and glimepiride; diuretics such as acetazolamide, ethoxzolamide, sultiame and zonisamide; protease inhibitors such as darunavir, amprenavir, fosamprenavir and tipranavir; mafenide; celecoxib; probenecid; sotalol; sulfasalazine; and sumatriptan.

Examples of hepatotoxic tetracycline antibiotics include, without limitation, tetracycline, chlortetracycline, oxytetracycline, demeclocycline, doxycycline, lymecycline, meclocycline, methacycline, minocycline, PTK 0796, rolitetracycline and tigecyc line.

Examples of hepatotoxic tricyclic antidepressants include, without limitation, amitriptyline, amitriptylinoxide, butriptyline, clomipramine, demexiptiline, desipramine, dibenzepin, dimetacrine, dosulepin, imipramine, imipraminoxide, lofepramine, melitracen, metapramine, nitroxezapine, nortriptyline, noxiptiline, pipofezine, propizepine, protriptyline, quinupramine, amineptine, iprindole, opipramol, tianeptine and trimipramine. In some embodiments, the tricyclic antidepressant is amitriptyline. Conditions treatable by amitriptyline include, without limitation, depression; anxiety disorder; attention-deficit hyperactivity disorder; migraine; eating disorders; bipolar disorder; neuralgia; insomnia; nocturnal enuresis; pain; and biliary dyskinesia.

Eating disorders treatable by the hepatotoxic drugs described herein (see, Table 1) include, without limitation, bulimia nervosa, anorexia nervosa, night eating syndrome, obesity, and binge eating disorder.

Examples of anxiety disorder treatable by hepatotoxic drugs described herein (see, Table 1) include, without limitation, generalized anxiety disorder and social to anxiety disorder.

Borderline personality disorder is a non-limiting example of a personality disorder treatable by hepatotoxic drugs described herein.

In some of any one of the embodiments described herein, the liver damage is characterized by hepatocellular injury and/or hepatitis. Examples of hepatotoxic agents which can cause such liver damage include, without limitation, ethanol, paracetamol, acarbose, amiodarone, bosentan, bromfenac, dantrolene, diclofenac, dihydralazine, disulfiram, felbamate, fluoxetine, halothane, isoniazid, kava, ketoconazole, labetalol, leflunomide, methotrexate, methyldopa, nefazodone, nicotinic acid, paroxetine, pemoline, propylthiouracil, pyrazinamide, rifampin, ritonavir, sertraline, statins, tacrine, tetracycline antibiotics, tolcapone, troglitazone, trovafloxacin, valproic acid, ximelagatran, zafirlukast, and zileuton. Paracetamol is an exemplary hepatotoxic agent.

In some of any one of the embodiments described herein, the liver damage is characterized by cholestasis. Examples of hepatotoxic agents which can cause such liver damage include, without limitation, anabolic steroids, azathioprine, azithromycin, captopril, chlorpromazine, cimetidine, ciprofloxacin, clopidogrel, dicloxacillin, erythromycin, estrogens, flucloxacillin, naproxen, phenobarbital, phenothiazine antipsychotics, phenytoin, sulindac, terbinafine, and tricyclic antidepressants.

In some of any one of the embodiments described herein, the liver damage is characterized by a combination of hepatitis and cholestasis. Examples of hepatotoxic agents which can cause such liver damage include, without limitation, amitriptyline, amoxicillin-clavulanic acid, carbamazepine, cyclosporine, enalapril, flutamide, methimazole, nitrofurantoin, sulfonamides, trazodone, trimethoprim, and verapamil.

In some of any one of the embodiments described herein, the liver damage is characterized by fibrosis and/or cirrhosis. Methotrexate is an exemplary hepatotoxic agent which can cause such liver damage.

In some of any one of the embodiments described herein, the liver damage is characterized by granulomas. Examples of hepatotoxic agents which can cause such liver damage include, without limitation, allopurinol, amoxicillin-clavulanic acid, carbamazepine, hydralazine, methyldopa, penicillamine, phenylbutazone, phenytoin, procainamide, quinidine and sulfonamides.

In some of any one of the embodiments described herein, the liver damage is to characterized by microvesicular steatosis. Examples of hepatotoxic agents which can cause such liver damage include, without limitation, nucleoside analog reverse transcriptase inhibitors (e.g., such as described herein) and valproate.

In some of any one of the embodiments described herein, the liver damage is characterized by neoplasms. Examples of hepatotoxic agents which can cause such liver damage include, without limitation, anabolic steroids and estrogens.

In some of any one of the embodiments described herein, the liver damage is characterized by non-alcoholic steatohepatitis. Examples of hepatotoxic agents which can cause such liver damage include, without limitation, amiodarone and tamoxifen.

In some of any one of the embodiments described herein, the liver damage is characterized by vascular lesions. Examples of hepatotoxic agents which can cause such liver damage include, without limitation, anabolic steroids, estrogens, azathioprine, retinol, methotrexate, busulfan and cyclophosphamide.

In any aspect of embodiments of the invention described herein, an alginate composition according to any of the embodiments described herein regarding an alginate composition may be used in association with a hepatotoxic agent according to any of the embodiments described herein regarding a hepatotoxic agent, unless otherwise indicated.

In any of the methods or treatments described herein the composition described herein may be used alone for protecting a subject from liver damage, as described herein, or in combination with another medication for protection against liver damage.

In some of any one of the embodiments of any of the aspects described herein, a treatment described herein for protecting a subject from liver damage associated with exposure to a hepatotoxic agent (e.g., treating liver damage induced by a hepatotoxic agent, preventing or reducing liver damage caused by a hepatotoxic agent, treating a medical condition treatable by a hepatotoxic agent, as described herein) is effected by administration of the composition described herein to a subject exposed to the hepatotoxic agent prior to, concomitant with, or shortly after exposure to the hepatotoxic agent.

In any aspect of embodiments of the invention described herein, a treatment regimen according to any of the embodiments described herein (e.g., with respect to a time and/or route of administration, and/or a condition being treated) may be used in to association with an alginate composition according to any one of the embodiments described herein regarding an alginate composition, and/or with a hepatotoxic agent according to any of the embodiments described herein regarding a hepatotoxic agent, unless otherwise indicated.

Herein, "shortly after exposure" means up to 24 hours after exposure (i.e., not later than 24 hours after exposure). In some of any one of the embodiments described herein, administration is effected up to 12 hours after exposure. In some embodiments, administration is effected up to 6 hours after exposure. In some embodiments, administration is effected up to 4 hours after exposure. In some embodiments, administration is effected up to 3 hours after exposure. In some embodiments, administration is effected up to 2 hours after exposure.

In preferred embodiments, administration is effected less than 1 hour after exposure. In some embodiments, administration is effected up to 50 minutes after exposure. In some embodiments, administration is effected up to 40 minutes after exposure. In some embodiments, administration is effected up to 30 minutes after exposure. In some embodiments, administration is effected up to 20 minutes after exposure. In some embodiments, administration is effected up to 10 minutes after exposure.

As used herein, the terms "concomitant" and "concomitantly" refer to an event (e.g., administration of a composition described herein) being performed as closely in time as is practically possible to another event (e.g., exposure to a hepatotoxic agent). In some embodiments, "concomitant" and "concomitantly" refer to events separated by no more than 1 hour. In some embodiments, "concomitant" and "concomitantly" refer to events separated by no more than 45 minutes. In some embodiments, "concomitant" and "concomitantly" refer to events separated by no more than 30 minutes. In some embodiments, "concomitant" and "concomitantly" refer to events separated by no more than 20 minutes. In some embodiments, "concomitant" and "concomitantly" refer to events separated by no more than 10 minutes.

In some of any one of the embodiments described herein, the composition described herein is administered no more than 24 hours prior to exposure to the hepatotoxic agent. In some embodiments, the composition is administered no more than 12 hours prior to exposure to the hepatotoxic agent. In some embodiments, the to composition is administered no more than 6 hours prior to exposure to the hepatotoxic agent. In some embodiments, the composition is administered no more than 3 hours prior to exposure to the hepatotoxic agent.

Exposure to the hepatotoxic agent may be effected, for example, by co-administration of a therapeutically effective amount of the hepatotoxic agent (e.g., a hepatotoxic drug) and the composition, as described herein.

In some of any one of the embodiments described herein, co-administration is such that the composition described herein is administered during a time period ranging from 100 minutes prior to exposure to the hepatotoxic agent to 50 minutes subsequent to exposure to the hepatotoxic agent. In some embodiments, the composition is administered no more than 75 minutes prior to exposure to the hepatotoxic agent. In some embodiments, the composition is administered no more than 50 minutes prior to exposure to the hepatotoxic agent. In some embodiments, the composition is administered no more than 40 minutes prior to exposure to the hepatotoxic agent. In some embodiments, the composition is administered no more than 30 minutes prior to exposure to the hepatotoxic agent. In some embodiments, the composition is administered no more than 20 minutes prior to exposure to the hepatotoxic agent. In some embodiments, the composition is administered no more than 10 minutes prior to exposure to the hepatotoxic agent.

In some of any one of the embodiments described herein, the composition described herein is administered no more than 40 minutes subsequent to exposure to the hepatotoxic agent. In some embodiments, the composition is administered no more than 30 minutes subsequent to exposure to the hepatotoxic agent. In some embodiments, the composition is administered no more than 20 minutes subsequent to exposure to the hepatotoxic agent. In some embodiments, the composition is administered no more than 10 minutes subsequent to exposure to the hepatotoxic agent.

In some of any one of the embodiments described herein, the composition described herein is administered during a time period ranging from 75 minutes prior to exposure to the hepatotoxic agent to 50 minutes subsequent to exposure to the hepatotoxic agent. In some embodiments, the composition is administered during a time period ranging from 50 minutes prior to exposure to the hepatotoxic agent to 40 minutes subsequent to exposure to the hepatotoxic agent. In some embodiments, the composition is administered during a time period ranging from 40 minutes prior to exposure to the hepatotoxic agent to 40 minutes subsequent to exposure to the hepatotoxic agent. In some embodiments, the composition is administered during a time period ranging from 30 minutes prior to exposure to the hepatotoxic agent to 30 minutes subsequent to exposure to the hepatotoxic agent. In some embodiments, the composition is administered during a time period ranging from 20 minutes prior to exposure to the hepatotoxic agent to 20 minutes subsequent to exposure to the hepatotoxic agent. In some embodiments, the composition is administered during a time period ranging from 10 minutes prior to exposure to the hepatotoxic agent to 10 minutes subsequent to exposure to the hepatotoxic agent.

In some of any one of the embodiments described herein wherein the composition described herein is administered subsequent to exposure to the hepatotoxic agent, the composition is administered during a time period ranging from 10 to 50 minutes subsequent to exposure to the hepatotoxic agent. In some embodiments, the composition is administered during a time period ranging from 20 to 40 minutes subsequent to exposure to the hepatotoxic agent. In exemplary embodiments, the composition is administered about 30 minutes subsequent to exposure to the hepatotoxic agent.

Without being bound by any particular theory, it is believed that the composition described herein is particularly effective for some indications described herein when the time during which alginate is present in the liver of the subject overlaps considerably with the time during which the liver is exposed to dangerous levels of a hepatotoxic agent described herein, or a hepatotoxic metabolite of the agent. For example, paracetamol hepatotoxicity is mediated by accumulation of hepatotoxic metabolites (e.g., N-acetyl-p-benzoquinone imine) in the liver following glutathione depletion, and such accumulation begins somewhat later (e.g., 15 minutes later) than the actual ingestion of the paracetamol.

In some of any one of the embodiments described herein, the composition described herein further comprises a therapeutically effective amount of a hepatotoxic agent, thereby facilitating co-administration of the alginate and a therapeutically effective amount of the hepatotoxic agent, as described herein.

Thus, the hepatotoxic agent (e.g., a hepatotoxic drug) may be formulated as a to part of an alginate-containing composition described herein. The hepatotoxic agent may be formulated as part of an alginate-containing composition described herein using processes well known in the art, e.g., by means of conventional mixing, dissolving, emulsifying, or encapsulating processes, or by homogenizing the hepatotoxic agent with the alginate and carrier as described herein.

Such co-formulations of a therapeutically effective amount of a hepatotoxic agent with an alginate composition are considerably superior to current formulations of therapeutically effective amounts of hepatotoxic agents, in view of the hepatoprotection provided by the alginate. Such co-formulations may therefore be used without required warnings against the risk of liver damage (or with less stringent warnings) and/or without required monitoring of liver function (or with less frequent monitoring) in a subject being administered the co-formulation, in contrast to current formulations of hepatotoxic agents.

In of any one of the embodiments described herein s, wherein a therapeutically effective amount of the hepatotoxic agent (e.g., hepatotoxic drug) is formulated separately from the alginate-containing composition described herein, the hepatotoxic agent may be formulated, dosed and administered in accordance with common practice in the art regarding the agent.

Techniques for formulation and administration of drugs may be found in "Remington's Pharmaceutical Sciences" Mack Publishing Co., Easton, Pa., latest edition, which is incorporated herein by reference.

As further shown in the Examples Section that follows, compositions such as described herein are highly effective at protecting against inflammatory bowel disease (IBD). This finding is surprising, as effective diffusion into the body is not necessarily a desirable property for treating IBD, in which the target for treatment is in the gastrointestinal tract.

Hence, according to another aspect of embodiments of the invention, the composition according to any one of the embodiments described herein is for use in treating IBD.

According to another aspect of embodiments of the invention, there is provided a method of treating an inflammatory bowel disease in a subject in need thereof from liver damage. The method comprises administering to the subject a therapeutically to effective amount, as defined herein, of a composition according to any one of the embodiments described herein.

According to another aspect of embodiments of the invention, there is provided a use of a composition according to any one of the embodiments described herein in the manufacture of a medicament for treating an inflammatory bowel disease.

As used herein, the phrase "inflammatory bowel disease (IBD)" refers to a disorder or disease characterized by inflammatory activity in the GI tract. Examples of inflammatory bowel diseases include, without limitation, Crohn's disease, ulcerative colitis, microscopic colitis, idiopathic inflammation of the small and/or proximal intestine, irritable bowel syndrome, collagenous colitis, lymphocytic colitis, ischaemic colitis, diversion colitis, Behcet's disease and indeterminate colitis.

In some of any one of the embodiments described herein, the inflammatory bowel disease is selected from the group consisting of Crohn's disease, ulcerative colitis, collagenous colitis, lymphocytic colitis, ischaemic colitis, diversion colitis, Behcet's disease and indeterminate colitis.

In some of any one of the embodiments described herein, the inflammatory bowel disease is Crohn's disease and/or ulcerative colitis.

In some embodiments, the IBD is manifested in the small intestine. By "manifested in the small intestine" it is meant that at least a portion of the inflamed tissues in the diseased subject are found in the small intestine.

IBDs that can be manifested in the small intestine include, but are not limited to, Crohn's disease and ulcerative colitis.

In some embodiments, the IBD is Crohn's disease. It is to be noted that while IBDs such as, for example, colitis, typically involve inflammation in the large intestine (colon) and/or the ileum, Crohn's disease often involves inflammation in certain regions of the small intestine.

In some of any one of the embodiments described herein, treatment of IBD is effected by co-administering a hepatotoxic agent suitable for treating IBD, as described herein.

In the context of embodiments described herein for treatment of IBD, the term "treating" refers to treatment of a subject afflicted with an IBD as defined herein and/or to of a subject prone to, or suspected as, being afflicted with an IBD, for example, by abrogating, substantially inhibiting, slowing or reversing the progression of IBD, substantially ameliorating inflammation associated with IBD, or substantially preventing or reducing the appearance of clinical or aesthetical symptoms (such as inflammatory symptoms) associated with IBD.

Compositions described herein may be formulated using a pharmaceutically acceptable carrier comprising excipients and auxiliaries, which facilitate processing of the alginate and/or hepatotoxic agent into preparations which can be used pharmaceutically. Proper formulation is dependent upon the route of administration chosen.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

In some embodiments, the alginate composition and/or hepatotoxic agent described herein are formulated for systemic administration.

In some embodiments, the alginate composition and/or hepatotoxic agent described herein are formulated for intraperitoneal administration (e.g., intraperitoneal injection), for example, intravenous administration.

For injection (e.g., intravenous injection), the carrier of the composition described herein may comprise a physiologically compatible buffer such as Hank's solution, Ringer's solution, or physiological saline buffer with or without organic solvents such as propylene glycol, polyethylene glycol. For transmucosal administration, penetrants are used in the formulation. Such penetrants are generally known in the art.

It is to be appreciated that some of the physiologically acceptable carriers described herein (e.g., saline) comprise sodium, and hence comprise a carrier and a source of sodium as described herein.

In some embodiments, the alginate composition and/or hepatotoxic agent described herein is formulated for rectal administration. As exemplified herein, rectal administration is a particularly effective route for administering the composition to described herein for treating inflammatory bowel disease.

The compositions of the present invention may be formulated in rectal compositions such as suppositories or retention enemas, using, e.g., conventional suppository bases such as cocoa butter or other glycerides.

As exemplified herein, oral administration is a particularly effective and convenient route for administering the composition described herein (e.g., for protecting against liver damage).

For oral administration, the suitable carriers enable the composition described herein to be formulated as liquids, syrups, slurries, suspensions, and the like, suitable for oral ingestion by a patient.

Pharmaceutical compositions, which can be used orally, include soft, sealed capsules made of gelatin and a plasticizer, such as glycerol or sorbitol. In soft capsules, the alginate may be dissolved in a suitable liquid carrier, as described herein. In addition, stabilizers may be added.

All formulations for oral administration should be in dosages suitable for the chosen route of administration.

For administration by inhalation, the composition described herein may be conveniently delivered in the form of an aerosol spray presentation from a pressurized pack or a nebulizer, with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount.

The composition described herein may be formulated for parenteral administration, e.g., by bolus injection or continuous infusion. Formulations for injection may be presented in unit dosage form, e.g., in ampoules or in multidose containers with optionally, an added preservative.

The phrase "unit dosage form", as used herein, describes physically discrete units, each unit containing a predetermined quantity of active ingredients (e.g., an alginate and/or hepatotoxic agent as described herein) calculated to produce the desired effect, in association with the pharmaceutically acceptable carrier and source of sodium described herein.

Compositions comprising alginate and a hepatotoxic agent, as described herein, formulated for oral or parenteral administration, may comprise aqueous solutions of the alginate and hepatotoxic agent (e.g., in an aqueous carrier described herein). Additionally, the composition may be prepared as a suspension or emulsion (e.g., appropriate oily injection suspensions and emulsions), for example, water-in-oil, oil-in-water or water-in-oil in oil emulsions. In some embodiments, the alginate is in an aqueous phase of a suspension or emulsion (e.g., a phase comprising an aqueous solution described herein), whereas the hepatotoxic agent (e.g., a lipophilic agent) is in a non-aqueous phase (e.g., in an oil phase). Suitable lipophilic solvents or vehicles include fatty oils such as sesame oil, or synthetic fatty acids esters such as ethyl oleate, triglycerides or liposomes.

Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the alginate and/or hepatotoxic agent described herein to allow for the preparation of highly concentrated solutions.

Compositions suitable for use in the context of embodiments of the present invention include compositions wherein the active ingredients are contained in an amount effective to achieve the intended purpose. More specifically, a therapeutically effective amount of alginate composition and/or hepatotoxic agent described herein is an amount effective to prevent, alleviate or ameliorate symptoms of liver damage and/or IBD and/or disease treatable by hepatotoxic agent, and/or prolong the survival of the subject being treated.

Determination of a therapeutically effective amount of alginate composition and/or hepatotoxic agent described herein is well within the capability of those skilled in the art, especially in light of the detailed disclosure provided herein, as well as knowledge in the art regarding dosage of hepatotoxic agents.

For any alginate composition and/or hepatotoxic agent described herein, the therapeutically effective amount or dose can be estimated initially from activity assays in animals (e.g., as exemplified herein). For example, a dose can be formulated in animal models to achieve a circulating concentration range that includes the $IC_{50}$ as determined by activity assays (e.g., the concentration of the alginate, which achieves a to half-maximal reduction of liver damage, as quantified according to assays known in the art (e.g., assays exemplified herein). Such information can be used to more accurately determine useful doses in humans.

A therapeutically effective amount for the alginate in a composition may range from about 8 mg/kg body weight to about 3,200 mg/kg body weight. In some embodiments, the therapeutically effective amount for the alginate is from about 16 mg/kg body weight to about 3,200 mg/kg body weight. In some embodiments, the therapeutically effective amount for the alginate is more than 40 mg/kg body weight. In some embodiments, the therapeutically effective amount for the alginate is at least about 80 mg/kg body weight. As is demonstrated in the Examples section that follows, an amount of an alginate of 100 mg/kg or higher was shown to exhibit a more potent protective effect in mice than 50 mg/kg.

Toxicity and therapeutic efficacy of the alginate composition and/or hepatotoxicity described herein can be determined based on prior knowledge in the art regarding such agents and/or by standard pharmaceutical procedures in experimental animals, e.g., by determining the $EC_{50}$, the $IC_{50}$ and the $LD_{50}$ (lethal dose causing death in 50% of the tested animals). The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each agent, but can be estimated from in vitro data. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release or delayed release formulation of a composition described herein, with course of treatment lasting from several hours to several weeks or until cure is effected or diminution of the disease state is achieved.

In some embodiments of any of the aspects described herein, administration is effected using a composition formulated as a slow release or delayed release composition, designed to achieve maximal overlap between exposure of the liver to the effects of the alginate and exposure of the liver to the hepatotoxic agent. In order to maximize such overlap, either the alginate composition, the hepatotoxic agent, or both, may be formulated for slow release and/or delayed release, depending on the relative pharmacokinetics of the alginate and hepatotoxic agent.

For example, in some embodiments wherein the alginate composition described herein is for co-administration with a hepatotoxic drug, the hepatotoxic drug is formulated for slow release and/or delayed release (e.g., a standard commercially available formulation of the drug), and the alginate composition described herein is formulated for a slow release and/or delayed release with similar release kinetics.

Techniques for preparing slow release formulations are known in the art, including suitable capsules which release liquid compositions (as described herein) after a pre-determined period of time.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the alginate composition and/or hepatotoxic agent described herein. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of to approval by the agency of the form of the compositions for human or veterinary administration. Such notice, for example, may be of labeling approved by the U.S. Food and Drug Administration for prescription drugs or of an approved product insert. Compositions comprising an alginate composition and/or hepatotoxic agent described herein formulated in a compatible pharmaceutical carrier may also be prepared, placed in an appropriate container, and labeled for treatment of an indicated condition or diagnosis, as is detailed hereinabove (e.g., treating liver damage, reducing or preventing a liver damage caused by at least one identified hepatotoxic agent, treating a condition treatable by the hepatotoxic agent, treating inflammatory bowel disease).

Thus, according to some embodiments of any aspect described herein, the composition described herein is packaged in a packaging material and identified in print, in or on the packaging material, for use in the treatment of a condition described herein (e.g., protecting against liver damage, treating liver damage, reducing or preventing a liver damage caused by at least one identified hepatotoxic agent, treating a condition treatable by a hepatotoxic agent in the composition, treating inflammatory bowel disease).

It is expected that during the life of a patent maturing from this application many relevant hepatotoxic agents will be developed and/or newly identified and the scope of the term "hepatotoxic agent" is intended to include all such new agents a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be to presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Alginates (VLVG and LVG) were obtained from NovaMatrix. VLVG refers to Very Low Viscosity (high) G alginate, as designated by the manufacturer. LVG refers to Low Viscosity (high) G alginate, as designated by the manufacturer. LVG alginate with different molecular weights are referred to herein as LVG54 and LVG150, wherein the numbers are those reported by the manufacturer for solution viscosity of the product for 1% (w/v) solutions.

Hyaluronan (sodium salt; ~400 kDa; from *Streptococcus equinus*) was obtained from Sigma.

Concanavalin A (Con A) was obtained from MP Biomedicals.

Paracetamol (APAP) syrup (Tiptipot® syrup) and the vehicle (paracetamol-free) for the syrup were obtained from CTS (Israel).

TNBS (2,4,6-trinitrobenzenesulfonic acid; picrylsulfonic acid) as a 5% w/v solution was obtained from Sigma. 1 ml TNBS (1%) ready-for-use solutions were prepared by mixing 200 µl of the 5 TNBS solution with 300 µl PBS (phosphate buffer saline; pH 7.2) and 500 µl ethanol.

Animals:

Male C57BL/6 (B6) mice (11-12 weeks old) and male Balb/c mice (6-7 weeks old) were obtained from Harlan Laboratories (Jerusalem, Israel). All mice were maintained in specific pathogen-free conditions. Mice were maintained in the Animal Core of the Hadassah-Hebrew University Medical School. All mice were administered standard laboratory chow and water ad libitum and kept in a 12-hour light/dark cycle.

Rheological Characterization of the Polysaccharide Solutions:

The viscosity of the polysaccharide solutions was tested on an AR 2000 stress-control rheometer (TA Instruments), operated in the coneplate mode with a cone angle of 1° and a 60 mm diameter. The apparent viscosities (mPa*seconds) of the solutions were tested at a shear rate of 1 seconds$^{-1}$. The measuring device was equipped with a temperature control unit (Peltier plate, ±0.05° C.) operated at 25° C.

Characterization of Size and Diffusion Coefficient by Dynamic Light Scattering (DLS):

Dynamic light scattering measurements of various alginate solutions were performed employing a Zetasizer® S apparatus (Malvern Instruments, UK). Measurements of molecular size were made at 25° C. using a diluted sample solution (1:50) in 10 mM HEPES buffer. Sample preparation was performed under sterile conditions using sterile glass test tubes. All glasses were prewashed (×3) with triple-filtrated (0.22 µm, membrane) DDW to reduce impurities, and then left to dry under sterile conditions. The samples were placed into the cleaned glass test tubes and diluted with the pre-filtrated 10 mM HEPES buffer. The scattering light was detected at a 90° angle. For data analysis, the viscosity (0.88 mPa·s) and the refractive index (1.33) of distilled water at 25° C. were used. The calculation of size distribution from light scattering measurements was based on the assumption that the molecules are spherical. As the alginate chains are not ideal spheres, the calculations of size give relative size values rather than an absolute size values.

The diffusion coefficient was measured by dynamic light scattering by recording the real time fluctuations in the intensity of the scattered light. The dynamic of polymer solutions can be investigated by measuring the intensity time correlation function as a function of the decay time, t. The time autocorrelation function, $g^{(2)}(q,t)$ (where q is the scattering vector, defined as:

$$q = \frac{4\pi}{\lambda} n \sin\theta$$

and t the delay time) of the intensity fluctuations I(q,t) is defined as:

$$g^{(2)}(q,t) = \lim_{T\to\infty} \frac{1}{T}\left[\int_0^T I(q,t')I(q,t'+t)dt'\right],$$

$g^{(2)}(q,t)$ can be related to the normalized electric field autocorrelation function, $g^{(1)}(q,t)$ using the following expression:

$$g^{(2)}(q,t) = A(1+\beta|g^{(1)}(t,q)|^2).$$

where A is a measured baseline determined for the largest t when no correlation exists and β is an optical constant for the system depending on the coherence of the detection ["Dynamic Light Scattering: Applications of Photon Correlation Spectroscopy", edited to by R. Pecora (Plenum, New York, 1985)]. In turn, $g^{(1)}(q,t)$ is related to the line-width distribution by:

$$g^{(1)}(q,t) = \int_0^\infty G(\Gamma) e^{-\Gamma t} d\Gamma,$$

where G(Γ) is a fraction of light scattered by particles characterized by a decay rate Γ. For a monodisperse particles undergoing Brownian motion in dilute suspensions the decay curve is that of a single exponential $$g^{(1)}(q,t) = \exp(-\Gamma t) = \exp(-q^2 D t)$$

where D is the translational diffusion coefficient.

In case of polydispersed particles, $g^{(1)}(q,t)$ is a sum of exponentials each corresponding to a particular particle, weighted by the intensity scattered by the particle.

Zeta Potential Measurements:

The zeta potential was determined using a Zeta Plus™ zeta potential analyzer (Brookhaven Instruments Corp., NY). The alginate solutions were diluted with 10 mM HEPES (pH 7.0) at a ratio of 1:30 in a quartz cuvette. Each batch was analyzed in triplicate. Results represent the average of 3 measurement cycles after subtraction of the diluent baseline from the averaged data.

Determination of Polysaccharide Molecular Weight:

Polysaccharide molecular weights were determined by gel permeation chromatography-multiangle laser light scattering (GPC-MALLS). Samples were separated on a chromatographic system comprising a Waters 606 pump followed by two PSS Suprema gel permeation columns connected in a series (column description: dimensions 300×8 mm², particle size 10 mm, porosity of 3000 and 10,000 angstrom). The flow rate was 0.5 ml/minute. The columns were kept at a constant temperature of 25° C. inside a Techlab K-4 controlled oven. The chromatographic system was attached to a Dawn DSP (Wyatt Technology) multiangle laser light scattering (MALLS) photometer equipped with a He/Ne laser working at 632.8 nm, a K5 refraction cell and 18 detectors at angles of 14-163°.

Concentration was monitored by a calibrated interferometric refractometer to Optilab DSP (Wyatt Technology). Data processing and molar mass calculation were performed with Wyatt ASTRA software version 4.7. Each sample was injected three times to ensure reproducibility. The dn/dc of the alginate, measured with the Optilab DSP, controlled by Wyatt dn/dc software, was found to be 0.155 ml/gram (aqueous buffer).

Aqueous buffer solutions were prepared from ultrapure water (0.055 µs/cm, USF Seral Purelab RO75, followed by USF Seral Purelab UV) supplemented with 0.1 M $NaNO_3$, 0.02% (w/v) $NaN_3$ and 10 mM imidazole. The buffer was titrated with $NaNO_3$ to a pH of 7.0 and filtered through a 0.1 µm VacuCap® 60 filter (Gelman Sciences).

Small Angle X-Ray Scattering (SAXS) Measurements:

Small angle scattering measurements were performed using the SAXSLAB GANESHA 300-XL system with Cu Kα radiation generated by a sealed microfocused tube (Genix 3D Cu-source with integrated monochromator) powered at 50 kV and 0.6 mA and three pinholes collimation. The scattering patterns were recorded by the Pilatus 300K detector. The scattering intensity I(q) was recorded in the interval $0.012 < q < 0.7$ Å$^{-1}$, where q is defined as:

$$q = \frac{4\pi}{\lambda}\sin\theta$$

where 2θ is the scattering angle, and is the radiation wavelength (1.542 Å). The solution under study was sealed in a thin-walled capillary (glass) of about 1.5 mm diameter and 0.01 mm wall thickness; measurements were performed under vacuum at ambient temperature. The 2D SAXS images were azimuthally averaged to produce one-dimensional profiles of intensity, I vs. q, using the two-dimensional data reduction program SAXSGUI. The scattering spectra of the capillary and solvent (double distilled water, 0.15M NaCl+homogenization) were also collected and subtracted from the corresponding solution data. Data was not converted to an absolute scale.

Cryogenic Transmission Electron Microscopy (Cryo-TEM):

Thin (~0.25 µm) specimens of the liquid alginate solution were deposited, under controlled humidity and temperature, on perforated carbon films supported on copper grids, which were hydrophilized by glow discharge. 3.5 µl of dispersion from the alginate sample were deposited on a TEM grid. The excess liquid was blotted with filter paper, and the specimen was vitrified by rapid plunging into liquid ethane pre-cooled with liquid nitrogen in a controlled-environment vitrification system. Such rapid cooling causes water to vitrify, and thus prevents microstructural changes by ice crystallization. The samples were examined at −178° C. using a FEI Tecnai™ 12 G² TWIN transmission electron microscope (Gatan model 794 CCD, bottom mounted) equipped with a Gatan 626 cryo-holder. Specimens were studied in a low-dose imaging mode to minimize beam exposure and electron beam radiation damage. Images were recorded digitally using the Digital Micrograph 3.6 software (Gatan).

Concanavalin a Mouse Model:

Injection of the T-cell mitogenic plant lectin concanavalin A (Con A) to non-sensitized mice results in hepatic apoptosis that precedes necrosis. The concanvalin A (Con A) model is a widely utilized mouse model, which mimics many aspects of human autoimmune hepatitis. It induces a massive liver necrosis in mice, simultaneously with lymphocyte infiltration into the liver, high levels of apoptotic hepatocytes and elevated serum alanine aminotransferase (ALT) and aspartate aminotransferase (AST). The liver injury is mediated by natural killer T (NKT) cells. Several apoptosis-related effector molecules, IFN-γ and TNF-α take part in the NKT cell-mediated liver injury. The immune-mediated liver injury which develops in the Con A model is very rapid, taking less than 48 hours. The peak for liver enzymes and pro-inflammtory cytokines is after less than 15 hours, making the model particularly useful for screening anti-inflammatory agents.

Tested solutions were administered intraperitoneally by injection of a volume of 200 µl per mouse or by administration per os of 250 µl per mouse, 1 hour before concanavalin A (Con A) administration. Saline (0.15 M NaCl) served as a negative control test solution. Dexamethasone was administered per os as a positive control, at a dose of 0.35 mg (17.5 µl) per mouse, 2 days before Con A administration.

Con A was dissolved at a concentration of 16 mg/kg in 200 µl of 50 mM Tris (pH 7), with 150 mM NaCl, and 4 mM $CaCl_2$, and injected (at a dose of 0.4 mg/mouse) intravenously into the tail vein of mice. Sera from individual mice were obtained 6, 24 and 48 hours (14 hours in some experiments) after Con A injection. All mice were sacrificed after 48 hours (14 hours in some experiments).

Partial Hepatectomy Mouse Model:

Male C57BL/6 (B6) mice (11-12 weeks old) were subjected to 87% partial hepatectomy. The mice were first sedated and then subjected to mid-ventral laparotomy, exposing the left and median hepatic lobes, followed by sequential ligation and resection of the median and left lobes, and closure of the peritoneal and skin wounds. 100 µl of 2% VLVG alginate or saline (in control mice) were then injected to the liver remnant. Small blood volumes were taken from the tail vein after 3, 6 and 24 hours respective to time period of the experiment. All animals were sacrificed 6, 24 or 48 hours after partial hepatectomy, and sera were then collected.

Colitis Mouse Model:

Delayed-type hypersensitivity colitis was induced in Balb/c mice by topical administration (skin-painting) of TNBS in order to sensitize the mice to TNBS, followed 7 days later by intracolonic installation of 120 µl of 1 TNBS. Sensitization with TNBS results in modification of autologous molecules in the mucosa, leading to priming of antigen-specific T cells. This model is accepted in the art as a model for IBD, including Crohn's disease.

TNBS-induced colitis is characterized by weight loss, which was calculated for each mouse by subtracting the weight on day 3 after TNBS installation from the weight on day 0 for every mouse.

Mice were sacrificed 3 days after the intracolonic installation of TNBS, and blood samples were collected by cardiac puncture, and were left to clot and then centrifuged to obtain serum for determination of serum cytokine (TNF-α) levels.

Colons (the proximal ends) were excised and then fixed in 10% formaldehyde, embedded in paraffin, sectioned and stained with H&E (hematoxylin & eosin). H&E-stained tissues were examined and scored by light microscopy for morphological and histo-pathological changes by a blinded pathologist. The pathologist used 2 scores for colon's evaluation:

the Dieleman score in which Extent, Inflammation, Damage (necrosis) and Regeneration are scored between 0 and 4—the activity score ranges between 0 to 12, representing the sum of scores from 0 to 3 each for severity of extent (E), damage (D), Inflammation(I) and regeneration (R); and the HAI (histological activity index) score, in which Inflammation and Epithelial Damage (ED) are scored between 0 and 4, and the total score is the sum of to the inflammation and epithelial damage scores.

Liver Enzyme Assays:

Serum activities of alanine aminotransferase (ALT) and aspartate aminotransferase (AST) were carried out after 1:5 dilutions (1:20 dilutions in samples taken 14 hours after Con A administration; 1:10 dilutions in paracetamol intoxication experiments), using a Reflovet® Plus clinical chemistry analyzer (Roche Diagnostics). Serum albumin levels after 48 hours were measured by an automatic analyzer.

Cytokine Assays:

Serum levels of IL-6, TNF-α and IFNγ were determined by "sandwich" ELISA, using a Quantikine® assay kit (R&D Systems), according to the manufacturer's instructions. Sera from mice were frozen until ELISA analysis.

Paracetamol Intoxication Mouse Model:

Male C57BL/6 (B6) mice (11-12 weeks old) were orally administered Tiptipot® paracetamol (acetaminophen, N-acetyl-p-aminophenol, APAP) syrup, after an overnight fast. The paracetamol dosages were 160 mg/kg (approximately 4 mg) or 320 mg/kg (approximately 8 mg) in other examples. The syrup was always diluted with saline to yield a total volume of 350 µl per mouse. Paracetamol was administered in the morning and food was put back to the cages 2 hours later. Mice were sacrificed 24 hours after paracetamol administration.

In the preventive model, alginate solutions (50, 100 or 200 µl per mouse) were administered per os or i.p. prior to administration of 160 mg/kg (approximately 4 mg) or 320 mg/kg (approximately 8 mg) paracetamol. In the therapeutic model, alginate solutions were administered with 160 mg/kg (4 mg) paracetamol (by being mixed with the paracetamol) or shortly thereafter.

Control mice were administered only with paracetamol syrup diluted with saline, as described hereinabove. In some experiments control mice were orally administered with the vehicle for the Tiptipot® paracetamol syrup, which was identical to the paracetamol syrup except for being paracetamol-free.

In some experiments paracetamol levels in the blood were determined 30 or 60 min after paracetamol administration, by taking 20 µl of blood from the tail vein of all mice. Paracetamol levels were measured by using a clinical kit based on fluorescence to polarization immunoassay (FPIA, AxSYM acetaminophen assay (Abbott), obtained from Ilex Medical Ltd., Israel). Serum activities of ALT and cytokines were determined as described herein.

After mice were sacrificed, a portion of each excised liver was fixed in 10% formalin and was then embedded in paraffin, sectioned (specimens of 5 µm) and stained with hematoxylin & eosin (H&E) or with IgG staining for detection of necrosis, nitrotyrosine and/or Ki-67. Briefly, necrosis staining was as follows: sections were first de-paraffinized and then were incubated with rabbit polyclonal IgG. Sections were then incubated with secondary antibody using the MACH 3 Rabbit HRP Polymer Detection and then dehydrated, cleared and mounted in synthetic resin. For color detection, DAB (3,3'-diaminobenzidine) was applied, followed by counterstaining. Quantification of necrosis was carried out by the Ariol SL-50 system (Applied Imaging) on microscope slides. Nitrotyrosine and Ki-67 immunostaining staining was performed similarly, using a rabbit polyclonal anti-nitrotyrosine antibody (Abcam) or an anti-Ki-67 antibody (DAKO).

Weight changes were monitored by weighing all the mice on the fasting day, the following morning, just before paracetamol administration (Day 1) and on the following day before sacrifice (Day 2).

Example 1

Alginate Homogenized in Saline

In order to obtain a more free-flowing form of alginate with enhanced diffusivity in biological milieu, alginate was dissolved in saline (0.15 M NaCl in water) rather than in pure water, and mixed intensively with a homogenizer (28,000 rotations per minute, for 3 minutes). Homogenization in saline was performed for alginate of various molecular weights, referred to as VLVG, LVG54 and LVG150, as described in the Materials and Methods section.

The properties of alginate homogenized in saline were evaluated and compared to those of alginate dissolved in double-distilled water (without homogenization).

All of the samples included alginate at a concentration of 2% (w/v), and were sterilized by filtration through a 0.2 µm nylon membrane. The solutions were maintained at a temperature of 4° C. until use, and appeared clear by eye.

The properties of the solutions were evaluated using viscosity measurement, characterization of size and diffusion coefficient by dynamic light scattering (DLS), and zeta potential measurement, as described in the Materials and Methods section hereinabove. The results are presented in Table 2 below.

As shown in Table 2, homogenization of alginate in saline resulted in a considerable decrease in diameter and a considerable increase of diffusion coefficient, as compared with alginate dissolved in DDW. As further shown therein, homogenization of alginate in saline also resulted in a less negative zeta potential, as well as in a lower viscosity and pH of alginate solutions. The reduction in viscosity was especially pronounced for VLVG alginate.

TABLE 2

| 2% (w/v) Solution* | pH | Viscosity (mPa · second at shear rate of 1 second$^{-1}$) | Zeta potential (mV) | Diameter (nm) | Diffusion Coefficient (cm$^2$/sec) |
|---|---|---|---|---|---|
| VLVG in saline (homogenized) | 6.1 | 15.5 | −17.8 | 8.3 | $2.64 \cdot 10^{-7}$ |
| VLVG in DDW (not homogenized) | 6.5 | 24.3 | −33.1 | 1728 | $1.26 \cdot 10^{-9}$ |
| LVG54 in saline (homogenized) | 6.8 | 269 | −18.7 | 13.2 | $1.65 \cdot 10^{-7}$ |
| LVG54 in DDW (not homogenized) | 7.2 | 273 | −39.0 | 1192 | $1.83 \cdot 10^{-9}$ |
| LVG150 in saline (homogenized) | 5.8 | 879 | −21.2 | 20.1 | N.D. |
| LVG150 in DDW (not homogenized) | 6.3 | 908 | −40.2 | 1200 | N.D. |

N.D. = not determined
*zeta potential, diffusion coefficient and diameter were determined using a solution concentration of 0.5% (w/v).

In addition, small angle X-ray scattering (SAXS) measurements were used (as described in the Materials and Methods section) to compare VLVG alginate homogenized in saline to VLVG dissolved in DDW without homogenization.

As shown in FIG. 1, the scattering pattern of 2% VLVG alginate in DDW exhibits a broad peak with a maximum at approximately 0.074 Å$^{-1}$ ($q_{max}$), whereas the scattering pattern of 2% VLVG alginate homogenized in saline does not exhibit a peak.

This scattering peak of alginate in DDW is characteristic of highly charged polyelectrolytes in aqueous solutions without added salt, and is attributed to electrostatic interference between the chains. A maximum in the scattering vector at 0.074 Å$^{-1}$ corresponds to an interchain distance (0 of about 85 Å, based on the equation $\zeta \approx 2\pi/q_{max}$. In contrast, a scattering pattern with no peak, as exhibited for alginate homogenized in saline, is similar to scattering patterns obtained from neutral polymers.

These SAXS results indicate that homogenization of the alginate in saline resulted in screening of the electrostatic interactions of the alginate. This may result in the alginate assuming a more globular shape, as compared to the extended conformation of alginate in DDW.

In addition, the VLVG alginate solutions were observed by cryogenic transmission electron microscopy, using procedures described in the Materials and Methods section.

As shown in FIG. 2, the non-homogenized VLVG alginate solution in DDW contained structures of approximately 10 nm or more in width. Such structures are clearly larger than individual alginate molecules.

In contrast, no structures were visible in samples of homogenized VLVG to alginate in saline (images not shown).

These results indicate that alginate typically forms structures via intermolecular associations between alginate molecules, and that homogenization in saline disrupts such associations, resulting in a more thoroughly dissolved form of alginate.

It is to be appreciated that the TEM results are consistent with the considerable reduction in diameter and increase in diffusion coefficient upon homogenization in saline, as shown in Table 2.

Taken together, the above results indicate that homogenization of alginate in saline resulted in alginate characterized by less intermolecular association between alginate molecules, a more globular and compact molecular shape, smaller size, and less negative surface charge, resulting in a very large (two orders of magnitude) increase in diffusion coefficients. Thus, homogenization in saline considerably enhances the efficiency of transport of the alginate molecules in biological milieu, as compared to alginate dissolved in water with no homogenization.

Without being bound by any particular theory, it is believed that homogenization facilitates better dissolution of alginate by promoting a homogenous distribution of the sodium ions in the alginate sample which disrupts intermolecular associations between alginate molecules, thereby resulting in dissolution of multi-molecular alginate structures, in a more compact conformation, and in more rapid and efficient transport in vivo.

Alginate homogenized in saline as described hereinabove was therefore used in all following experiments with alginate samples.

Example 2

Effects of Different Types of Alginate on Liver Damage in a Concanavalin a Model VLVG Alginate Compared to LVG54 and LVG150 Alginate Aqueous solutions of 2% alginate (w/v) were prepared by homogenization in saline, as described in Example 1, from the following types of alginate:

VLVG (molecular weight 30-50 kDa);

LVG54 (molecular weight 100 kDa); and

LVG150 (molecular weight 156 kDa).

Molecular weights were characterized as described hereinabove.

The solutions were administered intraperitoneally to adult male C57BL mice at a dose of 200 µl per mouse. One hour later, the mice were challenged with an intravenous injection of concanavalin A (Con A), as described hereinabove. Dexamethasone was administered as a positive control, and 200 µl saline served as a negative control. Each treatment group contained 4-5 mice. Serum levels of ALT, albumin, and the pro-inflammatory cytokines IL-6 and interferon-γ (IFNγ) were determined as described hereinabove.

As shown in Table 3 below and in FIG. 3, VLVG alginate reduced serum ALT levels in Con A-challenged mice at all tested time intervals, and LVG54 and LVG150 alginate reduced serum ALT levels only 48 hours after Con A administration.

TABLE 3

Serum levels of ALT (units/liter) in Con A model

| Treatment | Time after Con A administration | | |
|---|---|---|---|
| | 6 hours | 24 hours | 48 hours |
| Saline (control) | 272 ± 96 | 1219 ± 1359 | 1158 ± 135 |
| Dexamethasone | 146 ± 50 | 162 ± 50 | 69 ± 19 |
| VLVG alginate (2%) | 117 ± 56 | 200 ± 24 | 85 ± 35 |
| LVG150 alginate (2%) | 551 ± 275 | 2624 ± 1307 | 417 ± 113 |
| LVG54 alginate (2%) | 410 ± 50 | 763 ± 292 | 455 ± 204 |

Figure 4:
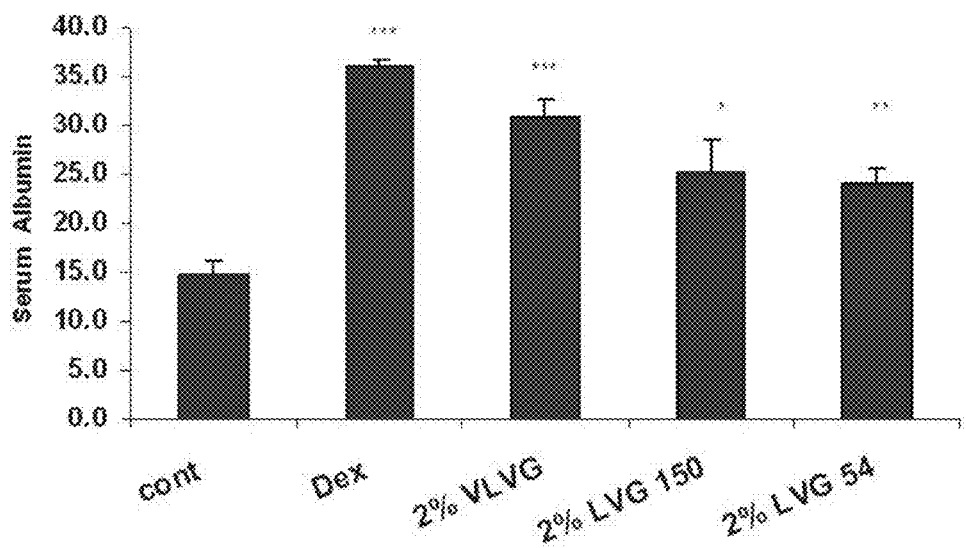

As shown in FIG. 4, each of the tested alginates increased albumin levels in Con A-challenged mice. The serum albumin levels 48 hours after Con A administration were 30.8±1.9 following administration of VLVG alginate (2%), 25.3±3.3 following administration of LVG150 alginate (2%), and 24.1±1.6 following administration of LVG54 alginate (2%), as compared to 14.8±1.4 following administration of saline and 36.2±0.6 following administration of dexamethasone.

Figure 3:
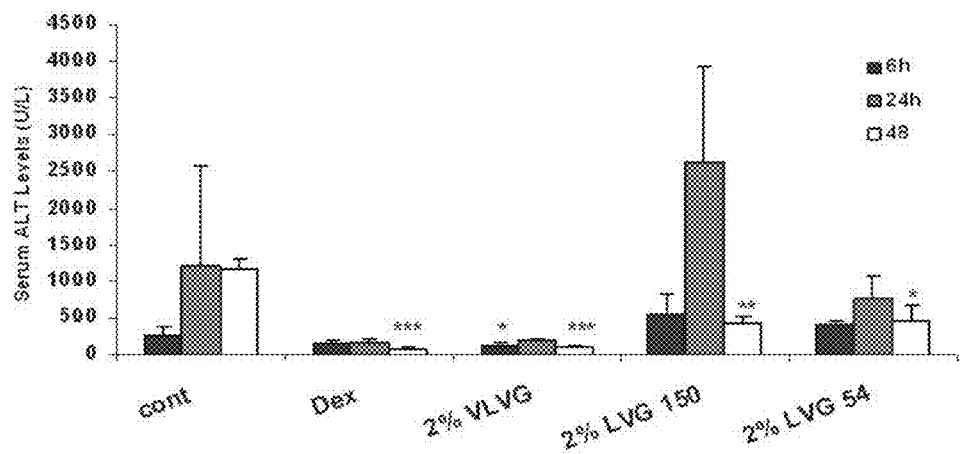

As further shown in FIGS. 3 and 4, the effects of VLVG alginate were comparable to those of dexamethasone, whereas the effects of LVG54 and LVG150 alginate were weaker.

Figure 5:
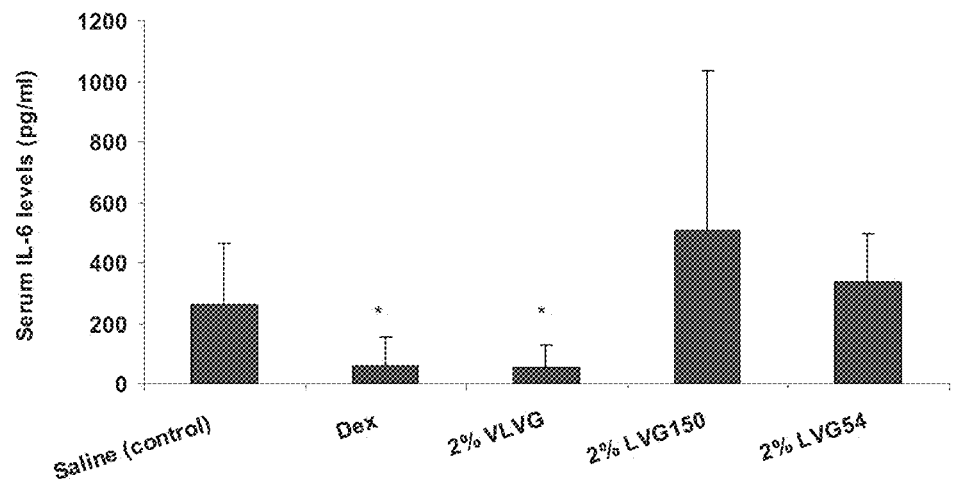
Figure 6:
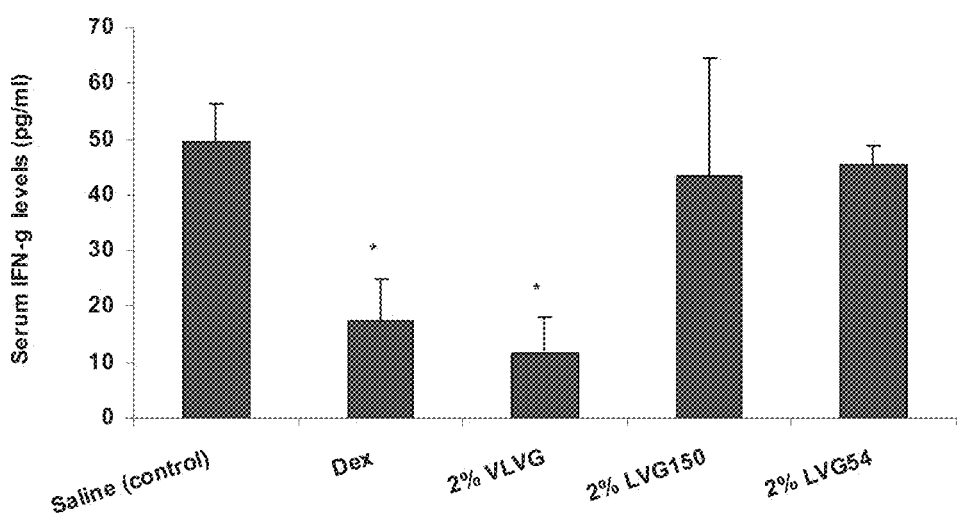

As shown in FIGS. 5 and 6, VLVG alginate reduced serum levels of the cytokines IL-6 (FIG. 5) and IFNγ (FIG. 6), whereas LVG54 and LVG150 alginate did not have any statistically significant effect on serum levels of these cytokines.

These results indicate that i.p. administration of the alginates protects against liver damage and reduces hepatic inflammatory responses, and that VLVG alginate provides stronger protection than do LVG54 and LVG150 alginate, which are characterized by higher molecular weights and higher solution viscosities than VLVG alginate.

Without being bound by any particular theory, it is assumed that the lower molecular weight and lower solution viscosity of VLVG alginate, as compared with LVG54 and LVG150 alginate, allow for better dissolution of the alginate and transport of the alginate from the injection site to the liver. It is further believed that by facilitating dissolution, a lower molecular weight and/or solution viscosity of alginate complements the disruption of intermolecular associations described in Example 1.

VLVG Alginate Compared to Hyaluronan and LVG150 Alginate (Assessment of Effects of Molecular Weight and Viscosity):

In order to ascertain to what extent chemical composition, molecular weight and viscosity are significant factors affecting the protection afforded by alginates, the protective effect of VLVG was compared with that of hyaluronan (HA) having a solution viscosity similar to that of LVG150. Hyaluronan is different than, but slightly similar to alginate, being composed of uronic acid residues (glucuronic acid) and acetylglucosamine residues. As a result of the differences in chemical composition, hyaluronan does not undergo ion-induced gelation characteristic of alginate.

An aqueous solution of 0.3% (w/v) hyaluronan (molecular weight 400 kDa) was prepared by homogenization in saline, using procedures described in Example 1. The solution viscosity was 700 mPa*seconds.

A 2% homogenized solution of VLVG in saline was prepared, as described hereinabove.

The hyaluronan and VLVG solutions were administered to mice prior to Con A injection, and the effects of the compounds was determined, as described hereinabove.

As shown in Table 4 below and in FIG. 7, the homogenized solution of VLVG alginate in saline reduced serum ALT levels in Con A-challenged mice as in the to experiment described hereinabove, whereas the hyaluronan did not reduce serum ALT levels.

TABLE 4

Serum levels of ALT (units/liter) in Con A model

| Treatment | Time after Con A administration | | |
|---|---|---|---|
| | 6 hours | 24 hours | 48 hours |
| Saline (control) | 189 ± 27 | 872 ± 507 | 262 ± 54 |
| Dexamethasone | 83 ± 21 | 68 ± 4 | 76 ± 23 |
| Hyaluronan (0.3%) | 421 ± 196 | 988 ± 630 | 378 ± 259 |
| VLVG alginate (2%) | 82 ± 32 | 117 ± 77 | 74 ± 49 |

Similarly, as shown in FIG. 8, the homogenized solution of VLVG alginate in saline increased albumin levels in Con A-challenged mice as in the experiment described hereinabove, whereas the hyaluronan did not increase albumin levels. The serum albumin levels 48 hours after Con A administration were 28.0±2 following administration of VLVG alginate (2%), and 17.0±2 following administration of hyaluronan (0.3%), as compared to 20.3±1 following administration of saline and 28.5±4 following administration of dexamethasone.

These results confirm that VLVG alginate protects against liver damage, and further indicates that polysaccharides characterized by different uronic acid composition, and by higher molecular weights and solution viscosities than those of VLVG alginate are less effective than VLVG alginate at protecting against liver damage.

Biotinylated VLVG Alginate Compared to VLVG Alginate (Assessment of Effects of Biotinylation):

The protective effects of solutions of biotinylated VLVG alginate (2%) were evaluated in order to determine the effects of introducing a biotin moiety.

Biotinylated alginate is of interest because it can be utilized in a variety of experiments, for example, to trace the path of alginate in the body after administration. VLVG alginate was labeled with biotin via carbodiimide chemistry, according to procedures described in Freeman et al. [*Biomaterials* 2008, 29:3260-3268]. No more than 3% of uronic acid residues were modified, so the biotin-labeled alginate was quite similar to the non-labeled alginate.

The biotinylated VLVG alginate was homogenized in saline, using procedures described in Example 1. The solution was administered to mice prior to Con A injection, and the effects of the compounds was determined, as described hereinabove.

As shown in Table 5 below and in FIG. 9, biotinylated VLVG alginate reduced serum ALT levels in Con A-challenged mice (similarly to VLVG alginate in experiments described hereinabove).

TABLE 5

Serum levels of ALT (units/liter) in Con A model

| Treatment | Time after Con A administration | | |
|---|---|---|---|
| | 6 hours | 24 hours | 48 hours |
| Saline (control) | 113 ± 23 | 508 ± 73 | 644 ± 159 |
| Dexamethasone | 74 ± 5 | 62 ± 14 | 65 ± 16 |
| Biotinylated VLVG alginate | 60 ± 7 | 76 ± 11 | 156 ± 33 |

Similarly, as shown in FIG. 10, biotinylated VLVG alginate increased albumin levels in Con A-challenged mice (similarly to VLVG alginate in experiments described hereinabove). The serum albumin levels 48 hours after Con A administration were 33±4 following administration of biotinylated VLVG alginate, as compared to 19±4 following administration of saline and 33±4 following administration of dexamethasone.

These results indicate that biotinylation of alginate (at a level of 3% or less of uronic acid residues) does not affect the protective effects of alginate against liver damage.

VLVG Alginate Compared to Very Low Molecular Weight (γ-Irradiated) Alginate Hyaluronan and LVG150 Alginate:

In order to determine whether any small alginate molecule exhibits liver protection, or whether liver protection is associated with a particular range of molecular to weights, alginate was γ-irradiated to reduce its molecular weight.

A 100 ml solution of alginate (LVG150, 2% (w/v)) was irradiated by γ-rays from a $^{60}$Co source at a cumulative dose of 28 kGy. The irradiated alginate had a solution viscosity of 1 mPa*second, and a molecular weight of approximately 3 kDa. At this molecular weight, the alginate was no longer capable of forming a persistent hydrogel in the presence of calcium ions.

As shown in Table 6 below and in FIG. 11, the γ-irradiated alginate did not reduce serum ALT levels, whereas VLVG alginate reduced serum ALT levels.

TABLE 6

Serum levels of ALT (units/liter) in Con A model

| Treatment | Time after Con A administration | | |
|---|---|---|---|
| | 6 hours | 24 hours | 48 hours |
| Saline (control) | 249 ± 162 | 346 ± 60 | 352 ± 85 |
| Dexamethasone | 28 ± 10 | 126 ± 37 | 68 ± 7 |
| VLVG alginate | 39 ± 8 | 106 ± 9 | 68 ± 11 |
| γ-Irradiated VLVG alginate | 261 ± 54 | 361 ± 121 | 310 ± 151 |

Similarly, as shown in FIG. 12, VLVG alginate increased albumin levels in Con A-challenged mice, whereas the γ-irradiated alginate did not increase albumin levels. The serum albumin levels 48 hours after Con A administration were 39±1 following administration of VLVG alginate, and 17±1 following administration of γ-irradiated alginate, as compared to 14±3 following administration of saline and 39±1 following administration of dexamethasone.

These results indicate that the protective effect of alginate is associated with a particular range of molecular weights.

Collectively, the above results indicate that alginate provides maximal liver protection when characterized by a molecular weight that is low (e.g., lower than 100 kDa) but higher than 3 kDa, and by a solution viscosity that is low (e.g., lower than about 200 mPa*seconds) but higher than 1 mPa*second. However, other changes in molecular structure caused by irradiation may be important.

Example 3

Effect of Alginate on Hepatic Inflammatory Responses

As discussed in Example 2, exemplary alginate solutions decreased levels of the pro-inflammatory cytokines interleukin-6 (IL-6) and interferon-γ (IFN-γ) 48 hours after administration of Con A. In order to further assess the therapeutic effect of anti-inflammatory effects of exemplary alginate solutions, levels of the pro-inflammatory cytokines interleukin-6 (IL-6) and interferon-γ (IF-γ) were measured in serum of mice challenged with Con A 14 hours after administration of Con A, which is around the time of peak inflammation and ensuing cytokine storm in the Con A model. Thus, alginate was administered to Con A-challenged mice as described in Example 2, except that mice were sacrificed and serum collected after 14 hours.

As shown in FIG. 13, VLVG alginate, LVG150 alginate and LVG54 alginate each considerably reduced serum levels of IL-6, 14 hours after Con A administration.

Similarly, as shown in FIG. 14, VLVG alginate, LVG150 alginate and LVG54 alginate each considerably reduced serum levels of IFN-γ 14 hours after Con A administration. The VLVG alginate was more effective at reducing IFN-γ levels than were LVG54 and LVG150 alginate, and was about as effective as dexamethasone.

These results indicate that alginate homogenized in saline is especially effective at reducing peak inflammatory responses, with VLVG alginate being especially effective.

In order to assess the protective effects of the reduction of pro-inflammatory cytokine levels, ALT and albumin serum levels were determined 14 hours after administration of Con A.

As shown in FIG. 15, VLVG alginate, LVG150 alginate and LVG54 alginate each considerably reduced serum ALT levels after 14 hours. The VLVG alginate was more effective at reducing ALT levels than were LVG54 and LVG150 alginate, and was at least as effective as dexamethasone. The serum ALT levels 14 hours after Con A administration were 92±23 units/liter following administration of VLVG alginate, 368±25 units/liter following administration of LVG150 alginate and 718±57 units/liter following administration of LVG54 alginate, as compared to 11,763±2,311 units/liter following administration of saline and 203±14 units/liter following administration of dexamethasone.

Similarly, as shown in FIG. 16, VLVG alginate, LVG150 alginate and LVG54 alginate each considerably increased albumin levels in Con A-challenged mice after 14 hours. The VLVG alginate was more effective at increasing albumin levels than were LVG54 and LVG150 alginate, and was at about as effective as dexamethasone. The serum albumin levels 14 hours after Con A administration were 33±0.4 following administration of VLVG alginate, 30±1.3 following administration of LVG150 alginate and 28±0.4 following administration of LVG54 alginate, as compared to 9±4 following administration of saline and 37±17 following administration of dexamethasone.

These results indicate that the reduction of pro-inflammatory cytokine levels during the peak inflammatory response plays a significant role in protection of the liver from damage.

In addition, these results confirm that VLVG alginate is more effective than alginate characterized by a higher molecular weight and solution viscosity.

Example 4

Effect of Alginate on Hepatic Architecture

The protective effects of alginate formulations were further examined using liver histology to examine the effects on hepatic architecture in a Con A model.

Intravenous administration of Con A to mice has been developed as a model for T-cell-mediated acute inflammatory liver injury in which hepatocytes are targeted by natural killer T (NKT) cells, leading to hepatocyte apoptosis and necrosis, with elevated serum ALT and AST.

Con A-challenged were administered VLVG alginate and LVG54 alginate, as described hereinabove. After mice were sacrificed, liver tissues were fixed in 10% formalin and were then embedded in paraffin, sectioned (specimens of 5 μm) and stained with hematoxylin and eosin (H&E) for morphological and histological examination.

As shown in FIGS. 17A-17D, VLVG alginate and dexamethasone both considerably reduced liver inflammation and necrosis caused by Con A, whereas LVG54 alginate had no apparent effect on liver tissue histology.

These results indicate that systemic administration of VLVG alginate homogenized in saline is particularly effective at reducing hepatic inflammatory responses.

Example 5

Biodistribution of Alginate

The biodistribution of alginate was determined using immunohistochemical staining for biotin-labeled alginate.

VLVG alginate was labeled with biotin via carbodiimide chemistry, using procedures as described in Freeman et al. [*Biomaterials* 29:3260-3268 (2008)]. No more than 3% of uronic acid residues were modified, so the biotin-labeled alginate was quite similar to the non-labeled alginate. A solution of 2% biotinylated VLVG alginate was administered intraperitoneally in a Con A mouse model, as described in Example 2, and the mice were sacrificed after 48 hours. The liver, spleen, colon or other tissue were then harvested and fixed in 10% formalin and were then embedded in paraffin and sectioned (specimens of 5 μm). For biotin detection, slides were first de-paraffinized, followed by addition of target retrieval solution and then blocking by peroxidase blocker (DAKO). After incubations and rinsings, Streptavidin-peroxidase (DAKO) was applied. For color detection, DAB (3,3'-diaminobenzidine) and chromogen substrate were applied. The procedure was ended by counterstaining and cover slip mounting.

As shown in FIG. 18, intraperitoneally administered VLVG alginate appeared in the liver parenchyma, as determined by immunohistochemical staining.

Biotinylated VLVG alginate was then administered intraperitoneally to healthy mice, and the presence of VLVG alginate in various tissues was examined.

As shown in FIGS. 19A and 19B, intraperitoneally administered VLVG alginate appeared in the liver and pancreas of mice (FIG. 19B), but not in the spleen or colon of mice (FIG. 19A).

These results indicate that therapeutically effective amounts of alginate can infiltrate organs such as liver and pancreas, following systemic administration.

Example 6

Effects of Orally Administered Alginate on Liver Damage in a Concanavalin a Model In order to test whether alginate has a protective effect against liver damage when administered orally, a 2% solution of VLVG alginate was prepared and administered to mice in a Con A model as described in Example 2, except that the alginate was administered per os, as described in the Materials and Methods section. to Serum levels of ALT, albumin and IL-6 were determined as described hereinabove.

As shown in Table 7 below and in FIG. 20, the orally administered VLVG alginate reduced serum ALT levels in Con A-challenged mice 24 and 48 hours after Con A administration, but not 6 hours after Con A administration.

TABLE 7

Serum levels of ALT (units/liter) in Con A model

| Treatment | Time after Con A administration | | |
|---|---|---|---|
| | 6 hours | 24 hours | 48 hours |
| Saline (control) | 157 ± 37 | 420 ± 82 | 745 ± 164 |
| Dexamethasone | 46 ± 6 | 65 ± 10 | 139 ± 26 |
| VLVG alginate (2%, per os) | 194 ± 25 | 315 ± 62 | 316 ± 54 |

Similarly, as shown in FIG. 21, the orally administered VLVG alginate increased albumin levels in Con A-challenged mice. The serum albumin levels 48 hours after Con A administration were 26.7±6.3 following oral administration of VLVG alginate, as compared to 9.2±3 following administration of saline and 42.5±2 following administration of dexamethasone.

In addition, as shown in FIG. 22, the orally administered VLVG alginate considerably reduced serum IL-6 levels in Con A-challenged mice 48 hours after Con A administration.

In view of the abovementioned positive results obtained with VLVG alginate, the experiment was repeated with oral administration of solutions of other types of alginate.

As shown in Table 8 below and in FIG. 23, the orally administered VLVG alginate, LVG64 alginate and LVG150 alginate each reduced serum ALT levels in Con A-challenged mice 48 hours after Con A administration, but not 6 or 24 hours after Con A administration. VLVG alginate was more effective than LVG54 and LVG150 alginate at reducing ALT levels after 48 hours.

TABLE 8

Serum levels of ALT (units/liter) in Con A model

| Treatment | Time after Con A administration | | |
|---|---|---|---|
| | 6 hours | 24 hours | 48 hours |
| Saline (control) | 64 ± 16 | 238 ± 115 | 322 ± 103 |
| Dexamethasone | 33 ± 12 | 37 ± 10 | 31 ± 5 |
| VLVG alginate (2%, per os) | 66 ± 27 | 251 ± 117 | 114 ± 40 |
| LVG150 alginate (2%, per os) | 72 ± 35 | 394 ± 263 | 205 ± 120 |
| LVG54 alginate (2%, per os) | 125 ± 16 | 443 ± 69 | 252 ± 63 |

As shown in FIG. 24, the orally administered VLVG alginate increased albumin levels in Con A-challenged mice, whereas the orally administered LVG54 and LVG150 alginates did not increase albumin levels. The serum albumin levels 48 hours after Con A administration were 37±5 following oral administration of VLVG alginate, 17±4 following oral administration of LVG150 alginate and 13±7 following oral administration of LVG54 alginate as compared to 15±5 following administration of saline and 41±4 following administration of dexamethasone.

In addition, as shown in FIG. 25, the orally administered VLVG alginate, LVG 150 alginate and LVG54 alginate each reduced serum IL-6 levels in Con A-challenged mice 48 hours after Con A administration.

The above results indicate that alginate exhibits protective effects against liver damage when administered orally, and that VLVG alginate is considerably more effective than other types of alginate, as is the case of intraperitoneal administration of alginate.

Example 7

Effects of Alginate on Liver Damage Following Partial Hepatectomy

In order to test whether alginate has a protective effect against a variety of types of liver damage, a 2% solution of VLVG alginate was prepared and administered to mice after a partial hepatectomy by injection to the liver remnant, performed as described in the Materials and Methods section. Serum levels of ALT and albumin to were determined at various time points, as described hereinabove.

As shown in FIG. 26, VLVG alginate reduced serum ALT levels 3 to 6 hours after partial hepatectomy.

As shown in FIG. 27, VLVG alginate increased albumin levels 6 hours after partial hepatectomy.

Similarly, as shown in FIGS. 28 and 29, VLVG alginate reduced serum ALT levels 6 to 24 hours after partial hepatectomy (FIG. 28), and increased serum albumin levels 24 hours after partial hepatectomy (FIG. 29).

Similarly, as shown in FIGS. 30 and 31, VLVG alginate reduced serum ALT levels 24 to 48 hours after partial hepatectomy (FIG. 30), and increased serum albumin levels 48 hours after partial hepatectomy (FIG. 31).

These results indicate that VLVG alginate effectively reduces liver damage and enhances viability of the liver during a broad time span after partial hepatectomy. These results further indicate that the protective effect of alginate described herein is effective against liver damage caused by a variety of causes.

Example 8

Effect of Alginate on Paracetamol Hepatotoxicity (Preventive Model)

The effect of alginate on paracetamol hepatotoxicity was investigated in a mouse model, as described in the Materials and Methods section.

To this end, 200 μl of a 2% solution of VLVG alginate was prepared as described hereinabove, and administered per os 30 minutes prior to intoxication with 4 mg paracetamol. Paracetamol intoxication was evaluated by measuring levels of ALT and IL-6, by measuring the weight loss typical of paracetamol intoxication, and by examining necrosis by IgG staining.

As shown in FIG. 32, the orally administered VLVG alginate dramatically reduced serum ALT levels in mice 24 hours after paracetamol administration, from 6,785±3,230 units per liter to 109±54 units per liter.

In addition, the orally administered VLVG alginate reduced serum IL-6 levels from 119.6±66.6 pg/ml to 45.6±33.3 pg/ml (p=0.05).

In addition, as shown in Table 9 below, the orally administered VLVG alginate reversed the weight loss caused by paracetamol intoxication between Day 1 (the day of to intoxication) and Day 2 (the following day).

TABLE 9

Effect of 4 mg paracetamol and VLVG alginate on body weight

| Group | Weight ratio (Day 2 vs. Day 1) | Change in weight from Day 1 to Day 2 (mg) |
|---|---|---|
| 4 mg paracetamol alone | 99% | −0.15 |
| 4 mg paracetamol + VLVG alginate (2% w/v, per os) | 105% | 1.17 |

$p < 0.0001$ for change in weight

In addition, as shown in FIGS. 33A and 33B, the orally administered VLVG alginate reduced the degree of necrosis in the liver of paracetamol intoxicated mice.

In order to assess the effect of alginate dosage on liver damage caused by paracetamol, the above experiment was repeated so as to compare the effects of 50, 100 and 200 μl of a 2% solution of VLVG alginate, which correspond to doses of 1 mg, 2 mg and 4 mg of VLVG alginate, respectively.

As shown in FIG. 34, 100 μl (2 mg alginate) and 200 μl (4 mg alginate) of the orally administered VLVG alginate solution dramatically reduced serum ALT levels in mice 24 hours after paracetamol administration, from 15133±1283 units per liter to 149±28 units per liter and 62±15 (200 μl) units per liter, respectively, whereas 50 μl (1 mg alginate) of the orally administered VLVG alginate only moderately reduced serum ALT levels, from 15133±1283 units per liter to 10813±2253 units per liter.

The effects of different dosages of alginate on liver damage caused by paracetamol were also assessed by staining for nitrotyrosine (a marker of oxidative stress associated with peroxynitrite formation due to increased nitric oxide production following liver injury) and Ki-67 (a marker of cell proliferation), according to procedures described in the Materials and Methods section. Paracetamol toxicity develops only after the onset of oxidative stress and mitochondrial dysfunction, and preventing these phenomena protects against paracetamol toxicity.

As shown in FIG. 35, treatment with 4 mg paracetamol resulted in extensive centrilobular nitrotyrosine staining, which was limited by 50 μl of 2% VLVG solution, and which was abolished by 200 μl of 2% VLVG solution.

As shown in FIG. 36, treatment with 4 mg paracetamol resulted in widespread cell proliferation in the liver, which was limited to certain areas by 50 μl of 2% VLVG solution, and which was abolished by 200 μl of 2% VLVG solution.

These results indicate that VLVG reduces oxidative stress and cell proliferation associated with paracetamol hepatotoxicity, and confirm that doses above 50 μl of 2% VLVG solution (1 mg alginate) can effectively prevent development of adverse effects associated with paracetamol hepatotoxicity.

Paracetamol is absorbed rapidly into the blood stream, reaching peak serum values in about 1-3 hours. In order to ascertain whether the protective effect is mediated by changes in paracetamol absorption, paracetamol levels in the blood were determined after administration of paracetamol.

As shown in FIG. 37, neither 100 μl nor 200 μl of the orally administered VLVG alginate solution exhibited any statistically significant effect on paracetamol levels in the blood 1, 4 or 24 hours after administration of paracetamol.

Similarly, when paracetamol levels in the blood were determined 30 minutes after administration of paracetamol, the paracetamol levels with and without administration of 200 μl of VLVG alginate solution were essentially identical: 67.72±40.55 μg/ml with VLVG alginate administration and 65.07±43.17 μg/ml without VLVG alginate.

These results indicate that the alginate does not affect paracetamol absorption, and that the protective effects of alginate are not mediated by changes in paracetamol absorption.

In order to further assess the effect of alginate on liver damage caused by paracetamol, the above experiment was repeated so as to compare the effect of orally administered VLVG alginate (200 μl of a 2% solution) with that of intraperitoneally administered VLVG alginate and with orally administered LVG54 and LVG150 alginate (200 μl of a 2% solution). Liver damage was evaluated by measuring ALT levels and body weight. Each treatment group included 4 mice.

As shown in FIG. 38, intraperitoneally administered VLVG alginate, orally administered VLVG alginate, LVG54 alginate and LVG150 alginate each reduced serum ALT levels in mice 24 hours after paracetamol administration. Furthermore, to VLVG alginate was more effective than LVG54 and LVG150 alginate at reducing ALT levels, and orally administered VLVG alginate was more effective than intraperitoneally administered VLVG alginate. ALT levels were 13,250±2,415 units/liter 24 hours after paracetamol administration alone, and were reduced to 1,987±1,316 units/liter following i.p. administration of VLVG alginate, to 202±159 units/liter following oral. Administration of VLVG alginate, to 3,525±3,938 units/liter following oral administration of LVG54 alginate, and to 6,504±4,277 units/liter following oral administration of LVG150 alginate.

In addition, as shown in Table 10 below, intraperitoneally administered VLVG alginate, orally administered VLVG alginate, LVG54 alginate and LVG150 alginate each reversed the weight loss caused by paracetamol intoxication between Day 1 (the day of intoxication) and Day 2 (the following day).

The abovementioned results indicate that oral administration of alginate is particularly effective for preventing liver damage caused by drug hepatotoxicity. The results further confirm that VLVG alginate is more effective against liver damage than alginates characterized by different molecular weights and viscosities.

TABLE 10

Effect of 4 mg paracetamol and alginate on body weight

| Group | Weight ratio (Day 2 vs. Day 1) | Change in weight from Day 1 to Day 2 (mg) |
| --- | --- | --- |
| 4 mg paracetamol alone | 96% | −1.05 |
| 4 mg paracetamol + VLVG alginate (2% w/v, i.p.) | 102% | 0.5 |
| 4 mg paracetamol + VLVG alginate (2% w/v, per os) | 101% | 2.1 |
| 4 mg paracetamol + LVG54 alginate (2% w/v, per os) | 108% | 2.08 |
| 4 mg paracetamol + LVG150 alginate (2% w/v, per os) | 103% | 0.8 |

In order to assess the ability of alginate to protect against liver damage caused by higher doses of paracetamol, the above experiments were repeated using doses of 8 mg paracetamol (a sub-lethal dose) instead of 4 mg. Paracetamol intoxication was evaluated by measuring levels of ALT and IL-6, and by measuring body weight. This experiment was performed twice, once with administration of a vehicle as a control (as described in the Materials and Methods section), and once without.

In one experiment, as shown in FIG. 39, VLVG alginate reduced serum ALT to levels in mice 24 hours after administration of 8 mg paracetamol, from 21,743±5,790 units/liter to 10,903±4,798 units per liter.

In addition, the orally administered VLVG alginate reduced serum IL-6 levels from 91.65±28.9 pg/ml to 43.17±15.42 pg/ml (p<0.005).

In addition, as shown in Table 11 below, the orally administered VLVG alginate reversed the weight loss caused by paracetamol intoxication between Day 1 (the day of intoxication) and Day 2 (the following day).

TABLE 11

Effect of 8 mg paracetamol and VLVG alginate on body weight

| Group | Weight ratio (Day 2 vs. Day 1) | Change in weight from Day 1 to Day 2 (mg) |
| --- | --- | --- |
| 8 mg paracetamol alone | 99% | −0.17 |
| 8 mg paracetamol + VLVG alginate (2% w/v, per os) | 110% | 2.42 |

In the second experiment, as shown in FIG. 40, VLVG alginate reduced serum ALT levels in mice 24 hours after administration of 8 mg paracetamol, from 25,520±3,068 units/liter to 11,845±7,025 units per liter, whereas only 28±1 units/liter ALT was detected in serum when the vehicle was administered instead of paracetamol.

In addition, the orally administered VLVG alginate reduced serum IL-6 levels from 247.0±234 pg/ml to 84.4±25 pg/ml, whereas only 18.1±1.5 pg/ml IL-6 was detected in serum when the vehicle was administered instead of paracetamol.

In addition, as shown in Table 12 below, the orally administered VLVG alginate reversed the weight loss caused by paracetamol intoxication between Day 1 (the day of intoxication) and Day 2 (the following day).

TABLE 12

Effect of 8 mg paracetamol and VLVG alginate on body weight

| Group | Weight ratio (Day 2 vs. Day 1) | Change in weight from Day 1 to Day 2 (mg) |
| --- | --- | --- |
| Syrup vehicle | 106% | 1.6 |
| 8 mg paracetamol alone | 99% | −0.3 |
| 8 mg paracetamol + VLVG alginate (2% w/v, per os) | 102% | 0.4 |

In addition, paracetamol levels in the blood were determined 30 minutes after administration of 8 mg paracetamol (or vehicle). The paracetamol levels with and without administration of VLVG alginate were essentially identical: 169.9±100.7 μg/ml with VLVG alginate administration and 153.4±99.8 μg/ml without VLVG alginate. In contrast, only 5.9±3.7 μg/ml paracetamol was detected when the vehicle was administered, which corresponds to the background signal for the assay kit.

These results indicate that alginate protects against relatively high doses of paracetamol, and confirm that the protective effects of alginate are not mediated by changes in paracetamol absorption.

Example 9

Effect of Alginate on Paracetamol Hepatotoxicity (Therapeutic Model)

In view of the results presented in Example 8, which show a strong protective effect of alginate when administered prior to administration of paracetamol (a preventive model), the effect of alginate on paracetamol hepatotoxicity was investigated in a therapeutic model, in which alginate was administered concurrently with, or subsequent to, administration of paracetamol, as described in the Materials and Methods section.

To this end, a 2% solution of VLVG alginate was prepared as described to hereinabove, and administered per os at a volume of 200 μl 30 or 60 minutes after intoxication with 4 mg paracetamol. Paracetamol intoxication was evaluated by measuring levels of ALT and IL-6, and by measuring body weight, as described hereinabove.

As shown in FIG. 41, VLVG alginate administered 30 minutes after paracetamol administration dramatically reduced serum ALT levels in mice 24 hours later, whereas VLVG alginate administered 60 minutes after paracetamol administration did not reduce serum ALT levels. Serum ALT levels were 1,025±1,310 units/liter when VLVG alginate was administered 30 minutes after paracetamol, 10,020±5,031 units/liter when VLVG alginate was administered 60 minutes after paracetamol, and 6,393±7,304 units/liter when paracetamol was administered without alginate.

In addition, VLVG alginate administered 30 minutes after paracetamol reduced serum IL-6 levels from 248.8±98.4 pg/ml to 63.4±42.5 pg/ml. In contrast, when VLVG alginate was administered 60 minutes after paracetamol, serum IL-6 levels were 131.1±52.4 pg/ml.

In addition, as shown in Table 13 below, VLVG alginate administered 30 minutes after paracetamol reversed the weight loss caused by paracetamol intoxication, whereas VLVG alginate administered 60 minutes after paracetamol did not.

TABLE 13

Effect of administration time of VLVG alginate on body weight

| Group | Weight ratio (Day 2 vs. Day 1) | Change in weight from Day 1 to Day 2 (mg) |
|---|---|---|
| 4 mg paracetamol alone | 94% | −1.5 |
| 4 mg paracetamol + VLVG alginate after 30 minutes | 104% | 1.03 |
| 4 mg paracetamol + VLVG alginate after 60 minutes | 98% | −0.43 |

The above experiment was repeated using VLVG alginate mixed with the paracetamol and co-administered.

As shown in FIG. 42, VLVG alginate dramatically reduced serum ALT levels in mice 24 hours later, whether administered 30 minutes after paracetamol or when administered mixed with paracetamol, although the protective effect of the VLVG alginate was somewhat stronger when administered after paracetamol. Serum ALT levels were 124±93 units/liter when VLVG alginate was administered 30 minutes after to paracetamol, 902±1,520 units/liter when VLVG alginate was mixed with paracetamol, and 6,734±3,783 units/liter when paracetamol was administered without alginate.

In addition, VLVG alginate reduced serum IL-6 levels in mice 24 hours later, whether administered 30 minutes after paracetamol or when administered mixed with paracetamol. VLVG alginate administered 30 minutes after paracetamol reduced serum IL-6 levels from 164.1±85.3 pg/ml to 58.9±31.8 pg/ml, while VLVG alginate mixed with paracetamol similarly reduced serum IL-6 levels to 58.9±38.7 pg/ml.

In addition, as shown in Table 14 below, VLVG alginate reversed the weight loss caused by paracetamol intoxication, whether administered 30 minutes after paracetamol or when administered mixed with paracetamol.

TABLE 14

Effect of administration time of VLVG alginate on body weight

| Group | Weight ratio (Day 2 vs. Day 1) | Change in weight from Day 1 to Day 2 (mg) |
|---|---|---|
| 4 mg paracetamol alone | 98% | −0.52 |
| 4 mg paracetamol + VLVG alginate after 30 minutes | 102% | 0.52 |
| 4 mg paracetamol mixed with VLVG alginate | 102% | 0.56 |

These results indicate that alginate exhibits a protective effect against drug hepatotoxicity, when administered prior to or concurrently with a hepatotoxic drug, or when administered less than 60 minutes after administration of the drug.

Example 10

Effect of Alginate on TNBS-Induced Colitis

Aqueous solutions of 2% VLVG alginate (w/v) were prepared by to homogenization in saline, as described hereinabove, and its effect on TNBS (2,4,6-trinitrobenzenesulfonic acid)-induced colitis in mice, a model for inflammatory bowel disease, was evaluated using procedures described in the Materials and Methods section herein.

Mice were treated three times via intrarectal administration with 110 μl of the 2% VLVG alginate or with 120 μl of saline (as a control), once 6 hours after TNBS installation, and on each of the following two days after installation.

As shown in FIG. 43, the VLVG alginate composition reduced weight loss considerably in mice with colitis relative to the saline-treated control ($p<0.001$).

As shown in FIG. 44, the VLVG alginate composition reduced colon damage (as determined by a histological activity index) in mice with colitis relative to the saline-treated control ($p<0.01$).

Representative images of stained colon tissue from saline-treated and VLVG alginate-treated mice are presented in FIGS. 45A and 45B, respectively.

As shown in FIG. 46, the VLVG alginate composition reduced serum TNF-α levels considerably in mice with colitis relative to the saline-treated control.

These results indicate that the VLVG alginate composition described herein is effective at treating IBD.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope to of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising:
   a) an alginate which is sodium alginate, said alginate having a molecular weight in a range of from 10 to 50 kDa,
   b) a source of sodium ions, wherein said source of sodium ions is not sodium alginate, and
   c) a carrier,
   said alginate in said composition being characterized by at least one of:
      (i) a zeta potential weaker than −25 mV, at a concentration of 0.5% (w/v) alginate in said carrier; and
      (ii) a diffusion coefficient of at least $10^{-8}$ cm$^2$/second, at a concentration of 0.5% (w/v) alginate in said carrier.

2. The composition of claim 1, wherein said molecular weight is in a range of from 30 to 50 kDa.

3. The composition of claim 1, being further characterized by a solution viscosity in a range of from 3 to 20 mPa*seconds, at a shear rate of 1 second$^{-1}$ and at a concentration of 2% (w/v) alginate in said carrier.

4. The composition of claim 3, wherein said solution viscosity is in a range of from 10 to 20 mPa*seconds.

5. The composition of claim 4, wherein said alginate has a molecular weight in a range of from 30 to 50 kDa.

6. The composition of claim 1, wherein said zeta potential is weaker than −20 mV, at a concentration of 0.5% (w/v) alginate in said carrier.

7. The composition of claim 1, wherein said diffusion coefficient is at least $10^{-7}$ cm$^2$/second, at a concentration of 0.5% (w/v) alginate in said carrier.

8. The composition of claim 1, wherein a concentration of said alginate in said carrier is in a range of from 0.4% to 10% (w/v).

9. The composition of claim 1, wherein said carrier is a pharmaceutically acceptable carrier.

10. A process for preparing the composition of claim 1, the process comprising contacting said alginate and a carrier comprising a source of sodium ions, and homogenizing the alginate and the carrier.

11. A process for preparing an alginate composition, the process comprising contacting:
    a) an alginate characterized by a molecular weight in a range of from 10 to 50 kDa and
    b) a carrier comprising a source of sodium ions, wherein said source of sodium ions is not sodium alginate,
    and homogenizing the alginate and the carrier using a mixing frequency of at least 10,000 per minute for at least 20 seconds.

12. The process of claim 11, wherein a concentration of said alginate is in a range of from 0.4% to 10% (w/v).

13. An alginate composition formed by the process of claim 11.

14. The composition of claim 13, being a pharmaceutical composition wherein said carrier is a pharmaceutically acceptable carrier.

* * * * *